United States Patent
Rothman et al.

(10) Patent No.: US 10,064,898 B2
(45) Date of Patent: *Sep. 4, 2018

(54) LISTERIA-BASED ADJUVANTS

(71) Applicants: ADVAXIS, INC., Princeton, NJ (US); THE TRUSTEES OF THE UNIVERSITY OF PENNSYLVANIA, Philadelphia, PA (US); UNIVERSITY OF GEORGIA RESEARCH FOUNDATION, INC., Athens, GA (US)

(72) Inventors: John Rothman, Lebanon, NJ (US); Anu Wallecha, Yardley, PA (US); Reshma Singh, Brookline, MA (US); Donald A. Harn, Jr., Athens, GA (US); Yvonne Paterson, Philadelphia, PA (US)

(73) Assignees: ADVAXIS, INC., Princeton, NJ (US); UNIVERSITY OF GEORGIA RESEARCH FOUNDATION, INC., Athens, GA (US); THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/220,641

(22) Filed: Jul. 27, 2016

(65) Prior Publication Data

US 2016/0324903 A1 Nov. 10, 2016

Related U.S. Application Data

(60) Division of application No. 14/004,455, filed as application No. PCT/US2012/028757 on Mar. 12, 2012, now Pat. No. 9,463,227, which is a continuation of application No. 13/210,696, filed on Aug. 16, 2011, now Pat. No. 9,017,660, and a continuation of application No. 13/290,783, filed on Nov. 7, 2011.

(60) Provisional application No. 61/451,651, filed on Mar. 11, 2011.

(51) Int. Cl.
| | |
|---|---|
| A01N 63/00 | (2006.01) |
| A61K 35/74 | (2015.01) |
| A61K 39/02 | (2006.01) |
| A61K 39/00 | (2006.01) |
| A61K 39/12 | (2006.01) |
| A61K 39/39 | (2006.01) |
| A61K 45/06 | (2006.01) |
| C12N 7/00 | (2006.01) |

(52) U.S. Cl.
CPC .......... *A61K 35/74* (2013.01); *A61K 39/0011* (2013.01); *A61K 39/0208* (2013.01); *A61K 39/12* (2013.01); *A61K 39/39* (2013.01); *A61K 45/06* (2013.01); *C12N 7/00* (2013.01); *A61K 2039/522* (2013.01); *A61K 2039/523* (2013.01); *A61K 2039/55594* (2013.01); *A61K 2039/585* (2013.01); *C12N 2710/20034* (2013.01)

(58) Field of Classification Search
CPC ..................................................... A61K 35/74
See application file for complete search history.

(56) References Cited

U.S. PATENT DOCUMENTS

| | | |
|---|---|---|
| 4,458,066 A | 7/1984 | Caruthers et al. |
| 4,521,382 A | 6/1985 | Kessick |
| 4,816,567 A | 3/1989 | Cabilly et al. |
| 5,204,253 A | 4/1993 | Sanford et al. |
| 5,262,177 A | 11/1993 | Brown et al. |
| 5,580,859 A | 12/1996 | Felgner et al. |
| 5,589,466 A | 12/1996 | Felgner et al. |
| 5,643,599 A | 7/1997 | Lee et al. |
| 5,679,647 A | 10/1997 | Carson et al. |
| 5,681,570 A | 10/1997 | Yang et al. |
| 5,736,524 A | 4/1998 | Content et al. |
| 5,739,118 A | 4/1998 | Carrano et al. |
| 5,804,566 A | 9/1998 | Carson et al. |
| 5,824,538 A | 10/1998 | Branstorm et al. |
| 5,830,702 A | 11/1998 | Portnoy et al. |
| 5,858,682 A | 1/1999 | Gruenwald et al. |
| 5,877,159 A | 3/1999 | Powell et al. |
| 5,922,583 A | 7/1999 | Morsey et al. |
| 5,922,687 A | 7/1999 | Mann et al. |
| 6,004,815 A | 12/1999 | Portnoy et al. |
| 6,015,567 A | 1/2000 | Hudziak et al. |
| 6,017,705 A | 1/2000 | Lurquin et al. |
| 6,051,237 A | 4/2000 | Paterson et al. |
| 6,099,848 A | 8/2000 | Frankel et al. |
| 6,287,556 B1 | 9/2001 | Portnoy et al. |
| 6,306,404 B1 | 10/2001 | LaPosta et al. |
| 6,329,511 B1 | 12/2001 | Vasquez et al. |
| 6,479,258 B1 | 11/2002 | Short |
| 6,500,432 B1 | 12/2002 | Dalemans et al. |

(Continued)

FOREIGN PATENT DOCUMENTS

| | | |
|---|---|---|
| CN | 1763093 A | 4/2006 |
| CN | 103687611 A | 3/2014 |

(Continued)

OTHER PUBLICATIONS

U.S. Appl. No. 13/290,783, filed May 31, 2012, Wallecha.

(Continued)

*Primary Examiner* — Albert M Navarro
(74) *Attorney, Agent, or Firm* — Alston & Bird LLP

(57) ABSTRACT

This invention provides methods and compositions for using *Listeria monocytogenes* as an adjuvant for enhancing immune responses in a subject.

14 Claims, 24 Drawing Sheets

Specification includes a Sequence Listing.

(56) References Cited

U.S. PATENT DOCUMENTS

| | | |
|---|---|---|
| 6,504,020 B1 | 1/2003 | Frankel et al. |
| 6,521,449 B1 | 2/2003 | Polack et al. |
| 6,565,852 B1 | 5/2003 | Paterson |
| 6,599,502 B2 | 7/2003 | Portnoy et al. |
| 6,635,749 B2 | 10/2003 | Frankel et al. |
| 6,641,814 B1 | 11/2003 | Andersen |
| 6,740,516 B2 | 5/2004 | Savitzky et al. |
| 6,767,542 B2 | 7/2004 | Paterson et al. |
| 6,773,900 B2 | 8/2004 | Short et al. |
| 6,855,320 B2 | 2/2005 | Paterson |
| 6,991,785 B2 | 1/2006 | Frey, II |
| 7,135,188 B2 | 11/2006 | Paterson |
| 7,375,091 B2 | 5/2008 | Cheever et al. |
| 7,425,449 B2 | 9/2008 | Portnoy et al. |
| 7,488,487 B2 | 2/2009 | Frankel et al. |
| 7,488,802 B2 | 2/2009 | Collins et al. |
| 7,521,051 B2 | 4/2009 | Collins et al. |
| 7,588,930 B2 | 9/2009 | Paterson et al. |
| 7,635,479 B2 | 12/2009 | Paterson et al. |
| 7,655,238 B2 | 2/2010 | Paterson et al. |
| 7,662,396 B2 | 2/2010 | Paterson et al. |
| 7,691,393 B2 | 4/2010 | Dubensky, Jr. et al. |
| 7,700,344 B2 | 4/2010 | Paterson et al. |
| 7,786,288 B2 | 8/2010 | Karp |
| 7,790,177 B2 | 9/2010 | Karp |
| 7,794,728 B2 | 9/2010 | Portnoy et al. |
| 7,794,729 B2 | 9/2010 | Paterson et al. |
| 7,820,180 B2 | 10/2010 | Paterson et al. |
| 7,842,289 B2 | 11/2010 | Dubensky et al. |
| 7,855,064 B2 | 12/2010 | Paterson et al. |
| 7,858,097 B2 | 12/2010 | Paterson et al. |
| 7,871,604 B1 | 1/2011 | Curtiss, III et al. |
| 7,887,822 B2 | 2/2011 | Ferrone et al. |
| 7,935,804 B2 | 5/2011 | Dubensky, Jr. et al. |
| 8,008,449 B2 | 8/2011 | Korman et al. |
| 8,114,414 B2 | 2/2012 | Paterson et al. |
| 8,168,757 B2 | 5/2012 | Finnefrock et al. |
| 8,241,636 B2 | 8/2012 | Paterson et al. |
| 8,268,326 B2 | 9/2012 | Paterson et al. |
| 8,287,883 B2 | 10/2012 | Dubensky et al. |
| 8,337,861 B2 | 12/2012 | Paterson et al. |
| 8,354,509 B2 | 1/2013 | Carven et al. |
| 8,383,796 B2 | 2/2013 | Korman et al. |
| 8,771,702 B2 | 7/2014 | Paterson et al. |
| 8,778,329 B2 | 7/2014 | Sewell |
| 8,791,237 B2 | 7/2014 | Paterson et al. |
| 8,906,664 B2 | 12/2014 | Paterson et al. |
| 8,956,621 B2 | 2/2015 | Paterson et al. |
| 9,012,141 B2 | 4/2015 | Paterson et al. |
| 9,017,660 B2 | 4/2015 | Shahabi et al. |
| 9,084,747 B2 | 7/2015 | Shahabi et al. |
| 9,226,958 B2 | 1/2016 | Harn et al. |
| 9,408,898 B2 | 8/2016 | Seavey et al. |
| 9,463,227 B2 | 10/2016 | Rothman et al. |
| 9,492,527 B2 | 11/2016 | Paterson et al. |
| 9,499,602 B2 | 11/2016 | Paterson et al. |
| 9,549,973 B2 | 1/2017 | Paterson et al. |
| 9,644,212 B2 | 5/2017 | Maciag et al. |
| 9,650,639 B2 | 5/2017 | Maciag et al. |
| 9,700,608 B2 | 7/2017 | Paterson et al. |
| 2002/0025323 A1 | 2/2002 | Paterson et al. |
| 2002/0028206 A1 | 3/2002 | Paterson |
| 2002/0136737 A1 | 9/2002 | Frankel et al. |
| 2002/0165172 A1 | 11/2002 | Sallberg et al. |
| 2003/0202985 A1 | 10/2003 | Paterson |
| 2003/0219802 A1 | 11/2003 | Dhaini et al. |
| 2003/0220239 A1 | 11/2003 | Simard et al. |
| 2004/0013685 A1 | 1/2004 | Andersen et al. |
| 2004/0013690 A1 | 1/2004 | Portnoy et al. |
| 2004/0031690 A1 | 2/2004 | Portnoy et al. |
| 2004/0058342 A1 | 3/2004 | Yousef |
| 2004/0228877 A1 | 11/2004 | Dubensky et al. |
| 2005/0048081 A1 | 3/2005 | Frankel et al. |
| 2005/0118184 A1 | 6/2005 | Paterson et al. |
| 2005/0129715 A1 | 6/2005 | Paterson et al. |
| 2005/0281783 A1 | 12/2005 | Kinch et al. |
| 2006/0051380 A1 | 3/2006 | Schulick et al. |
| 2006/0073170 A1 | 4/2006 | Papierok |
| 2006/0093582 A1 | 5/2006 | Paterson et al. |
| 2006/0104991 A1 | 5/2006 | Paterson et al. |
| 2006/0121053 A1 | 6/2006 | Sweeney et al. |
| 2006/0204516 A1 | 9/2006 | Paterson et al. |
| 2006/0205067 A1 | 9/2006 | Paterson et al. |
| 2006/0210540 A1 | 9/2006 | Paterson et al. |
| 2006/0223835 A1 | 10/2006 | Paterson et al. |
| 2006/0233835 A1 | 10/2006 | Paterson et al. |
| 2006/0269561 A1 | 11/2006 | Paterson et al. |
| 2007/0003567 A1 | 1/2007 | Paterson et al. |
| 2007/0154953 A1 | 7/2007 | Brunner et al. |
| 2007/0207170 A1 | 9/2007 | Dubensky et al. |
| 2007/0207171 A1 | 9/2007 | Dubensky et al. |
| 2007/0253976 A1 | 11/2007 | Paterson et al. |
| 2007/0264279 A1 | 11/2007 | Paterson et al. |
| 2008/0124354 A1 | 5/2008 | Paterson et al. |
| 2008/0131456 A1 | 6/2008 | Paterson et al. |
| 2008/0213295 A1 | 9/2008 | Cheever et al. |
| 2008/0241069 A1 | 10/2008 | Paterson |
| 2009/0081248 A1 | 3/2009 | Paterson et al. |
| 2009/0081250 A1 | 3/2009 | Paterson et al. |
| 2009/0186051 A1 | 7/2009 | Paterson et al. |
| 2009/0202587 A1 | 8/2009 | Paterson et al. |
| 2010/0069344 A1 | 3/2010 | Wang et al. |
| 2010/0189739 A1 | 7/2010 | Frankel et al. |
| 2010/0233212 A1 | 9/2010 | Dubensky |
| 2010/0291140 A1 | 11/2010 | Paterson et al. |
| 2011/0129499 A1 | 6/2011 | Maciag et al. |
| 2011/0142791 A1 | 6/2011 | Shahabi |
| 2011/0223107 A1 | 9/2011 | Tremblay et al. |
| 2011/0223187 A1 | 9/2011 | Shahabi et al. |
| 2011/0271358 A1 | 11/2011 | Freeman et al. |
| 2011/0305724 A1 | 12/2011 | Paterson et al. |
| 2012/0014984 A1 | 1/2012 | Shahabi |
| 2012/0114685 A1 | 5/2012 | Sewell |
| 2012/0135033 A1 | 5/2012 | Wallecha |
| 2012/0177678 A1 | 7/2012 | Paterson et al. |
| 2013/0259891 A1 | 10/2013 | Harn et al. |
| 2014/0186387 A1 | 7/2014 | Lauer et al. |
| 2014/0199258 A1 | 7/2014 | Rothman |
| 2014/0234370 A1 | 8/2014 | Shahabi |
| 2014/0248304 A1 | 9/2014 | Paterson et al. |
| 2014/0314708 A1 | 10/2014 | Maciag et al. |
| 2014/0335120 A1 | 11/2014 | Maciag et al. |
| 2015/0079034 A1 | 3/2015 | Seavey et al. |
| 2015/0098964 A1 | 4/2015 | Singh et al. |
| 2015/0125480 A1 | 5/2015 | Paterson et al. |
| 2015/0196628 A1 | 7/2015 | Mason et al. |
| 2015/0238584 A1 | 8/2015 | Shahabi et al. |
| 2015/0297702 A1 | 10/2015 | Shahabi |
| 2015/0335721 A1 | 11/2015 | Paterson et al. |
| 2015/0343047 A1 | 12/2015 | Paterson et al. |
| 2015/0366955 A9 | 12/2015 | Shahabi et al. |
| 2016/0022814 A1 | 1/2016 | Petit et al. |
| 2016/0024173 A1 | 1/2016 | Paterson et al. |
| 2016/0158331 A1 | 6/2016 | Paterson et al. |
| 2016/0206716 A1 | 7/2016 | Seavey et al. |
| 2016/0220652 A1 | 8/2016 | Petit et al. |
| 2016/0228530 A1 | 8/2016 | Paterson |
| 2016/0256538 A1 | 9/2016 | Harn et al. |
| 2016/0361401 A1 | 12/2016 | Shahabi et al. |
| 2016/0367650 A1 | 12/2016 | Paterson |
| 2017/0028045 A1 | 2/2017 | Paterson et al. |
| 2017/0042996 A1 | 2/2017 | Wallecha et al. |
| 2017/0049867 A1 | 2/2017 | Seavey et al. |
| 2017/0080064 A1 | 3/2017 | Petit et al. |
| 2017/0100469 A1 | 4/2017 | Paterson et al. |
| 2017/0106072 A1 | 4/2017 | Petit |
| 2017/0204361 A1 | 7/2017 | Eapen et al. |
| 2017/0246273 A1 | 8/2017 | Wallecha et al. |
| 2017/0281691 A1 | 10/2017 | Paterson et al. |

FOREIGN PATENT DOCUMENTS

| | | |
|---|---|---|
| EP | 0902086 | 3/1999 |
| EP | 1408048 | 4/2004 |

(56) References Cited

FOREIGN PATENT DOCUMENTS

| | | |
|---|---|---|
| JP | 2007-161700 A | 6/2007 |
| JP | 2008-509677 T | 4/2008 |
| JP | 2013-526837 | 6/2013 |
| RU | 2009122560 A | 12/2010 |
| WO | WO 1990/012594 | 11/1990 |
| WO | WO 1992/020356 | 11/1992 |
| WO | WO 1993/015212 | 8/1993 |
| WO | WO 1994/017192 | 8/1994 |
| WO | WO 1996/014087 A1 | 5/1996 |
| WO | WO 1996/034631 | 11/1996 |
| WO | WO 1996/039154 | 12/1996 |
| WO | WO 1997/003211 | 1/1997 |
| WO | WO 1998/004720 | 2/1998 |
| WO | WO 1998/048026 | 10/1998 |
| WO | WO 1999/007861 | 2/1999 |
| WO | WO 1999/025376 | 5/1999 |
| WO | WO 2001/072329 | 10/2001 |
| WO | WO 2001/079274 | 10/2001 |
| WO | WO 2001/079274 | 7/2002 |
| WO | WO 2003/045318 A2 | 6/2003 |
| WO | WO 2003/092600 | 11/2003 |
| WO | WO 2003/102168 | 12/2003 |
| WO | WO 2004/004771 | 1/2004 |
| WO | WO 2004/006837 | 1/2004 |
| WO | WO 2004/056875 | 7/2004 |
| WO | WO 2004/062597 A2 | 7/2004 |
| WO | WO 2004/072286 | 8/2004 |
| WO | WO 2004/084936 | 10/2004 |
| WO | WO 2004/110481 | 12/2004 |
| WO | WO 2005/009463 | 2/2005 |
| WO | WO 2005/037233 | 4/2005 |
| WO | WO 2005/061534 | 7/2005 |
| WO | WO 2005/071088 | 8/2005 |
| WO | WO 2006/017856 | 2/2006 |
| WO | WO 2006/036550 | 4/2006 |
| WO | WO 2007/061848 | 5/2007 |
| WO | WO 2007/103225 | 9/2007 |
| WO | WO 2007/106476 A2 | 9/2007 |
| WO | WO 2007/130455 A2 | 11/2007 |
| WO | WO 2007/137258 A2 | 11/2007 |
| WO | WO 2008/045148 A2 | 4/2008 |
| WO | WO 2008/079172 A2 | 7/2008 |
| WO | WO 2008/109155 | 9/2008 |
| WO | WO 2008/130551 | 10/2008 |
| WO | WO 2008/140812 A2 | 11/2008 |
| WO | WO 2009/110950 | 9/2009 |
| WO | 2009/143085 | 11/2009 |
| WO | WO 2009/0143085 | 11/2009 |
| WO | WO 2009/143167 | 11/2009 |
| WO | WO 2010/008782 A1 | 1/2010 |
| WO | WO 2010/011870 | 1/2010 |
| WO | WO 2010/027827 | 3/2010 |
| WO | WO 2010/040135 A1 | 4/2010 |
| WO | WO 2010/077634 | 7/2010 |
| WO | WO 2010/102140 A1 | 9/2010 |
| WO | WO 2011/060260 A2 | 5/2011 |
| WO | WO 2011/066342 | 6/2011 |
| WO | WO 2011/100754 A1 | 8/2011 |
| WO | WO 2012/125551 A1 | 9/2012 |
| WO | WO 2012/138377 A2 | 10/2012 |
| WO | WO 2013/019906 | 2/2013 |
| WO | WO 2013/025925 A1 | 2/2013 |
| WO | WO 2013/138337 A1 | 9/2013 |
| WO | WO 2014/100079 | 6/2014 |
| WO | WO 2015/126921 A1 | 8/2015 |
| WO | WO 2015/130810 A2 | 9/2015 |
| WO | WO 2015/134722 A2 | 9/2015 |
| WO | WO 2015/164121 A1 | 10/2015 |
| WO | WO 2015/167748 A1 | 11/2015 |
| WO | WO 2016/011320 | 1/2016 |
| WO | WO 2016/011353 A1 | 1/2016 |
| WO | WO 2016/011357 A1 | 1/2016 |
| WO | WO 2016/011362 A1 | 1/2016 |
| WO | WO 2016/061182 A1 | 4/2016 |
| WO | WO 2016/061277 A1 | 4/2016 |
| WO | WO 2016/100924 A1 | 6/2016 |
| WO | WO 2016/100929 A1 | 6/2016 |
| WO | WO 2016/126876 | 8/2016 |
| WO | WO 2016/126878 A2 | 8/2016 |
| WO | WO 2016/141121 A1 | 9/2016 |
| WO | WO 2016/154412 A2 | 9/2016 |
| WO | WO 2016/183361 A1 | 11/2016 |
| WO | WO 2016/191545 A1 | 12/2016 |
| WO | WO 2016/207859 A1 | 12/2016 |
| WO | WO 2017/048714 A1 | 3/2017 |
| WO | WO 2017/048850 A1 | 3/2017 |
| WO | WO 2017/049218 A2 | 3/2017 |
| WO | WO 2017/066706 A1 | 4/2017 |
| WO | WO 2017/085691 A1 | 5/2017 |
| WO | WO 2017/106754 A2 | 6/2017 |
| WO | WO 2017/132547 A1 | 8/2017 |

OTHER PUBLICATIONS

U.S. Appl. No. 60/490,089, filed Jul. 24, 2003, Dubensky.
Abachin et al. "Formation of D-alanyl-lipoteichoic acid is required for adhesion and virulence of Listeria monocytogenes" Molecular Microbiology 43(1), 1-14, (2002).
Adams et al., 1992, "Cre-lox recombination in *Escherichia coli* cells Mechanistic differences from the in vitro reaction", J. Mol. Biol. 226:661-673.
Ahmadzadeh et al. Tumor Antigen-Specific CD8 T Cells Infiltrating the Tumor Express High Levels of PD-1 and Are Functionally Impaired. Blood (2009) 114: 1537-1544.
Ahmed, Nabil, et al. "Immunotherapy for osteosarcoma: genetic modification of T cells overcomes low levels of tumor antigen expression." Molecular Therapy 17.10 (2009): 1779-1787.
Alexander et al. "Characterization of an Aromatic Amino Acid-Dependent Listeria monocytogenes Mutant: Attenuation, Persistence, and Ability to Induce Protective Immunity in Mice", Infection and Immunity, vol. 61, No. 5, p. 2245-2248. May 1993.
Al-Lazikani et al. JMB Standard Conformations for the Canonical Structures of Immunoglobulins., J. Mol. Biol. 273:927-948 (1997).
Allision et al., 1997, "Cloning and characterization of a Prevotella melaninogenica hemolysin", Infect. Immun. 65(7):2765-71.
Altschul "Amino Acid Substitution Matrices from an Information Theoretic Perspective", J. Mol. Biol. 219:555-565 (1991).
Altschul et al. Basic Local Alignment Search Tool Basic Local Alignment Search Tool; J. Mol. Biol. 215:403-410 (1990).
Altschul et al. "Gapped Blast and PSI-Blast: A New Generation of Protein Database Search Programs." (1997) Nucleic Acids Res. 25:3389-3402.
Altschul et al. A Protein Alignment Scoring System Sensitive at all Evolutionary Distances; J. Mol. Evol. 36:290-300 (1993).
Amersham. Introduction to Glutathione S-transferase (GST) Gene Fusion System, Pharmacia Biotech; BioDirectory, Piscataway, N.J., ( pp. 384-391) (2001).
An et al., 1996, "A recombinant minigene vaccine containing a nonameric cytotoxic-T-Lymphocyte epitope confers limited protection against Listeria monocytogenes infection", Infect. Immun., vol. 64, No. 5, p. 1685-1693.
Anderson, 1998, "Human gene therapy ", Nature, Apr. 30; 392 (6679 Suppl):25-30.
Angelakopoulos et al., "Safety and Shedding of an Attenuated Strain of Listeria Monocytogenes With a Delection of ACTA/PLCB in Adult Volunteers: A Dose Escalation Study of Oral Innoculation", Infection and Immunity 2002, 70(7): 3592-3601.
Anthony "Precursor Lesions for Liver Cancer in Humans" Cancer Res. (1976) 36:2579-2583.
Attwood et al., "The Babel of Bioinformatics", Science, vol. 290, No. 5491: 471-473, 2000.
Auchtung et al (Regulation of a Bacillus Subtilis Mobile Genetic Element by Intercellular Signaling and the Global DNA Damage Response. Proc Natl Acad Sci U S A. Aug. 30, 2005;102(35):12554-9).
Auerbuch, et al. "Development of a Competitive Index Assay to Evaluate the Virulence of Listeria Monocytogenes Acta Mutants During Primary and Secondary Infection of Mice" (2001) Infect. Immunity 69:5953-5957.

(56) References Cited

OTHER PUBLICATIONS

Awwad, 1989, "Cyclophosphamide-induced immunologically mediated regression of a cyclophosphamide-resistant murine tumor: a consequence of eliminating precursor L3T4+ suppresor T-cells", Cancer Res., 49(7):1649-1654.
Baca et al. "Protein Chemistry and Structure: Antibody Humanization Using Monovalent Phage Display", (1997) J. Biol. Chem. 272:10678-10684.
Baert et al. "Influence of Immunogenicity on the Long-Term Efficacy of Infliximab in Crohn's Disease" (2003) New Engl. J. Med. 348:601-608.
Baloglu et al. "Immune Responses of Mice to Vaccinia Virus Recombinants Expressing Either Listeria Monocytogenes Partial Listeriolysin or *Brucella abortus* Ribosomal L7/L12 Protein", Vet Microbiol 2005, 109(1-2): 11-7.
Barbas Synthetic Human Antibodies; Nature Medicine, 1:837-839 (1995).
Bargmann et al. "The neu oncogene encodes an epidermal growth factor receptor-related protein" Nature 319, 226-230, Jan. 16, 1986.
Bear, 1986, "Tumor-specific suppressor T-cells which inhibit the in vitro generation of cytolytic T-cells from immune and early tumor-bearing host spleens", Cancer Res., Apr. 46;(4 Pt 1):1805-12.
Beattie et al. "Cloning and charcterization of T-cell-reactive protein antogens from Listeria monocytogenes", infect. Immune. Sep. 1990, 58(9):2792-803.
Beatty et al. "IFN-gamma-dependent inhibition of tumor angiogenesis by tumor-infiltrating CD4+ T cells requires tumor responsiveness to IFN-gamma", J Immunol. Feb. 15, 2001;166(4):2276-82.
Beaucage et al., "Deoxynucelotide phosphoramidites—a new class of key intermediates for deoxypolynucleotide synthesis", 1981, Tetra. Lett., 22:1859-1862.
Becker at al., The changes in the T helper 1 (Th1) and T helper 2 (Th2) cytokine balance 3,4during HIV-1 infection are indicative of an allergic response to viral proteins that may bereversed by Th2 cytokine inhibitors and immune response modifiers—a review and hypothesis; Viruses Genes 28:5-18 (2004).
Belt et al (1991) "Efficient CDNA Cloning by Direct Phenotypic Correction of a Mutant Human Cell Line (HPRT2) Using an Epstein-Barr Virus-Derived CDNA Expression Vector", Nucleic Acids Res. 19, 4861-4866.
Beniaminovitz et al. "Prevention of Rejection in Cardiac Transplantation by Blockade of the Interleukin-2 Receptor With a Monoclonal Antibody" (2000) New Engl. J. Med. 342:613-619.
Benvegnu, et al. Space Occupying lesions of the liver detected by ultrasonography and their relation to hypatocellular Carcinoma in Cirrhosis; Liver 12:80-83 (1992).
Bernhard et al., 2002, "Vaccination against the HER-2/neu oncogenic protein", Endocrine-Related Cancer, 9:33-44.
Bielecki et al. "Bacillus subtilis expressing a haemolysin gene from Lesteria monocytogenes can grow in mammalian cells", Nature 1990, 354:175-176.
Billaut-Mulot, O. et al. Interleukin-18 modulates immune responses induced by HIV-1 Nef DNA prime/protein boost vaccine; Vaccine 19:95-102 (2000).
Billington et al., 1997, "The Arcanobacterium (Actinomyces) pyogenes hemolysin, pyolysin, is a novel member of the thiol-activated cytolysin family", J. Bacteriol. Oct; 179(19):6100-6.
Bird et al. "An autologous dendritic cell canine mammary tumor hybrid-cell fusion vaccine", Cancer Immunol Immunother. Jan. 2011;60(1):87-97.
Bishop et al. "Adoptive Transfer of Immunity to Listeria Monocytogenes the Influence of in Vitro Stimulationon Lymphocyte Subset Requirements", J. Immunol. 139: 2005-2009 (1987).
Bodmer et al., 1988, "Enhanced recognition of a modified peptide antigen by cytotoxic T cells specific for influenza nucleoprotein", Cell 52:253-258.
Boon et al., 2006, "Human T-cell responses against melanoma" Annu. Rev. Immunol. 24:175-208.

Bourquin et al., 2000, "Myelin oligodendrocyte glycoprotein-DNA vaccination induces antibody-mediated autoaggression in experimental autoimmune encephalomyelitis" Eur. J. Immunol. 30:3663-3671.
Bouwer et al. Acquired immunity to an intracellular pathogen: immunologic recognition of L. monocytogenes-infected cells, Immunol. Rev. Aug. 1997; 158:137-46.
Bouwer et al. Cytotoxic-T-lymphocyte responses to epitopes of listeriolysin O and p60 following infection with Listeria monocytogenes, Infect. Immune. Jul. 1996; 64(7):2515-22.
Boyer "DNA Prime Listeria Boost Induces a Cellular Immune Response to SIV Antigens in the Rhesus Macaque Model That Is Capable of Limited Suppression of SIV239 Viral Replication", Virology. 333: 88-101, 2005.
Brantl et al. "Molecular Analysis of the Replication Region of the Conjugative *Streptococcus agalactiae* Plasmid PIP501 in Bacillus subtilis. Comparison with Plasmids PAM Beta 1 and PSM19035", Nucleic Acid Res 18: 4783-4790, 1990.
Brett et al. "Comparison of Antigen Presentation of Influenza A Nucleoprotein Expressed in Attenuated AROA—*Salmonella typhimurium* With That of Live Virus", J Immunol. Apr. 1, 1993;150(7):2869-84.
Brockstedt et al. "Listeria-based cancer vaccines that segregate immunogenicity from toxicity", Proc Natl Acad Sci U S A. Sep. 21, 2004;101(38):13832-7.
Bron et al, "Use of the ALR Gene as a Food-Grade Selection Marker in Lactic Acid Bacteria" 2002, Appl Environ Microbiol, 68: 5663-70.
Bron et al., 2004, "Identification of Lactobacillus Plantarum Genes That Are Induced in the Gastrointestinal Tract of Mice", J. Bacteriol. Sep.; 186(17):5721-9.
Brown et al. "Chemical synthesis and cloning of a tyrosine tRNA gene" 1979, Meth. Enzymol. 68:109-151.
Brown et al., 1988, "Site-specific integration in Saccaropolyspora erthraea and multisite integration in Streptomyces lividans of actinomycete plasmid pSE101", J. Bacteriology 170:2287-2295.
Bruder et al. "Efficient induction of cytotoxic CD8+ T cells against exogenous proteins: establishment and characterization of a T cell line specific for the membrane protein ActA of Listeria monocytogenes", Eur. J. Immunol. Sep. 1998; 28(9):2630-9.
Bruhn et al., 2005, "Characterization of anti-self CD8 T-cell responses stimulated by recombinant Listeria monocytogenes expressing the melanoma antigen TRP-2", Vaccine, Jul. 21; 23(33):4263-72.
Brundage et al., 1993, "Expression and phosphorylation of the Listeria monocytogenes ActA protein in mammalian cells", Proc. Natl. Acad. Sci. USA 90:11890-11894.
Bubert et al., 1997, "The Listeria monocytogenes iap gene as an indicator gene for the study of PrfA-dependent regulation", Mol. Gen. Genet. Sep.; 256(1):54-62.
Calendar et al., Poster presented at the ISOPOL Meeting 2001, http://64.233.169.104/search?q=cache:mA_uJpQsCrcJ:www.ma.uni-heidelberg.de/inst/imh/download/isopol.doc+Portnoy+Isopol+2001&hl=en&ct=clnk&cd=3&gl=us.
Camilli et al. "Insertional Mutagenesis of Listeria Monocytogenes With a Novel TN917 Derivative That Allows Direct Cloning of DNA Flanking Transposon Insertions", J Bacteriol, Jul. 1990;172(7):3738-44.
Camilli et al. "Listeria Monocytogenes Mutants Lacking Phosphatidylinositol-Specific Phospholipase C Area Virulent" J Exp Med 173:751-754, (1991).
Camilli et al., 1993, "Daul roles of plcA in Listeria monocytogenes pathogenesis", Mol. Microbiol. 8:143-157.
Carbone, 1989, "Induction of ovalbumin-specific cytotoxic T cells by in vivo peptide immunization" J. Exp. Med. 169:603-612.
Carbone, 1990, "Class I-restricted processing and presentation of exogenous cell-associated antigen in vivo", J. Exp. Med. 171:377-387.
Carpenter et al. Non-Fc Receptor-Binding Humanized Anti-CD3 Antibodies Induce Apoptosis of Activated Human T Cells; J. Immunol. 165:6205-6213 (2000).

(56) References Cited

OTHER PUBLICATIONS

Catic et al. "Introduction of protein or DNA delivered via recombinant *Salmonella typhimurium* into the major histocompatibility complex class I presentation pathway of macrophages", Microbes Infect., Feb. 1999, 1(2):113-21.
Cenatiempo, "Prokaryotic gene expression in vitro: transcription-translation coupled systems." 1986, Biochimie 68:505-516.
Chen et al. "Episomal Expression of Truncated Listeriolysin O in LmddA-LLO—E7 Vaccine Enhances Antitumor Efficacy by Preferentially Inducing Expansions of CD4FoxP3_ andCD8 T Cells", Cancer Immunol Res; 2(9) Sep. 2014, pp. 911-922.
Chen et al., "PD-L1 Expression Is Characteristic of a Subset of Aggressive B-Cell Lymphomas and Virus-Associated Malignancies" Clin Cancer Res 19: 3462-3473 (2013).
Chothia et al. Canonical Structures for the Hypervariable Regions of Immunoglobulins; J Mol. Biol. 196:901-917 (1987).
Chothia et al. Confirmations of immunoglobulin hypervariable Regions; Nature 342:878-883 (1989).
Ciesielski et al. "Therapeutic Effect of a T Helper Cell Supported CTL Response Induced by a Survivin Peptide Vaccine against Murine Cerebral Glioma"; Cancer Immunol Immunother; 57(12): 1827-1835 (2008).
Clackson et al. Making Antibody Fragments Using Phage Display Libraries; Nature 352: 624-628 (1991).
Clark et al., "Clinical use of streptolysin-O to facilitate antisense oligodeoxyribonucleotide delivery for purging autografts in chronic myeloid leukaemia", Bone Marrow Transplantation, vol. 23, No. 12, 1999, pp. 1303/1308.
Clifton et al., "Overcoming Cancer Immune Tolerance and Escape", Clinical Cancer Research: An Official Journal of the American Association for Cancer Research 2009, vol. 15, No. 3, pp. 749-751.
Collins et al. "Directional cloning of DNA fragments at a large distance from an initial probe: a circularization method", Proc Natl Acad Sci USA. Nov. 1984;81(21):6812-6.
Courvalin et al. 1995, "Gene transfer from bacteria to mammalian cells", C R Acad Sci III, Dec; 318(12):1207-12.
Coynault et al. "Virulence and vaccine potential of *Salmonella typhimurium* mutants deficient in the expression of the RpoS (sigma S) regulon", Mol Microbiol. Oct. 1996;22(1):149-60.
Cunto-Amesty et al. 2003, "Strategies in cancer vaccines development", Int. J. Parasitol. 33(5-6):597-613.
Da'Dara et al. Elimination of helminth infection restores HIV-1C vaccine-specific T cellresponses independent of helminth-induced IL-10; Vaccine; 3;28(5):1310-7 (2010).
Dakappagari et al., 2000, "Prevention of mammary tumors with a chimeric HER-2 B-cell epitope peptide vaccine", Cancer Res. Jul. 15; 60(14):3782-9.
Darji et al. "Antigen-specific T cell receptor antagonism by antigen-presenting cells treated with the hemolysin of Listeria monocytogenes: a noval type of immune escape", Eur. J. Immunol. Jul. 1997; 27(7):696-703.
Darji et al. T-cell anergy induced by antigen presenting cells treated with the hemolysin of Listeria monocytogenes, Immunol. Lett. Jun. 1, 1997, 57(1-3):33-7.
Darji et al. The role of the bacterial membrane protein ActA in immunity and protection against Listeria monocytogenes, J. Immunol. Sep. 1, 1998, 161(5):2414-20.
Darji et al., 1995, "Hyperexpression of listeriolysin in the nonpathogenic species Listeria innocua and high yield purification", J. Biotechnol. Dec. 15; 43(3):205-12.
Darji et al., 1995, "Listeriolysin generates a route for the presentation of exogenous antigens by major histocompatibility complex class I", Eur. J. Immunol. Oct.;25(10):2967-71.
Darji et al., 1997, "Oral somatic transgene vaccination using attenuated S. typhimurium" Cell 91:765-775.
Darji et al., 1997, "TAP-dependent major histocompatibility complex class I presentation of soluble proteins using listeriolysin", Eur. J. Immunol. Jun.; 27(6):1353-9.

Darji et al., 2003, "Induction of immune responses by attenuated isogenic mutant strains of Listeria monocytoge" Vaccine 1; 21 Suppl. 2:S102-9.
De Boer et al., "A division inhibitor and a topological specificity factor coded for by the minicell locus determine proper placement of the division septum in *E. coli*." 1989, Cell 56:641-649.
De Bruin et al. Selection of high-affinity phage antibodies from phage display libraries; Nature Biotechnol. 17:397-399 (1999).
De Las Mulas, J. Martin, et al. "Oncogene HER-2 in canine mammary gland carcinomas." Breast cancer research and treatment 80.3 (2003): 363-367.
De Maria, Raffaella, et al. "Spontaneous feline mammary carcinoma is a model of HER2 overexpressing poor prognosis human breast cancer." Cancer research 65.3 (2005): 907-912.
Decatur et al., "A PEST-Like Sequence in Listeriolysin O Essential for Listeria monocytogenes Pathogenicity", Science 2000, 290:992-995.
Dell'Erba et al., "Immunohistochemical Reactivity of Anti-Melanoma Monoclonal Antibody 225.28S in Human Breast Cancer Biopsies", Anticancer Res. 2001, vol. 21, No. 2A, pp. 925-930.
Dembo, A et al. Limit Distribution of Maximal Non-Aligned Two-Sequence Segmental Score Ann. Prob. 22:2022-2039; (1994).
Dermime et al. 2004, "Vaccine and antibody-directed T cell tumour immunotherapy" Biochim Biophys Acta. 1704(1):11-35.
Deshpande et al., 1997, "Isolation of a contact-dependent haemolysin from Mycobacterium tuberculosis", J. Med. Microbiol. Mar.; 46(3):233-8.
Dietrich et al., 1998, "Delivery of antigen-encoding plasmid DNA into the cytosol of macrophages by attenuated suicide Listeria monocytogenes" Nature Biotechnology 15:181-185.
Dietrich et al., 2001, "From evil to good: a cytolysin in vaccine development", Trends Microbiol. Jan.; 9(1):23-8.
Disis "Generation of immunity to the HER-2/neu oncogenic protein in patients with breast and ovarian cancer using a peptide-based vaccine", Clin Cancer Res. 5(6):1289-97, Jun. 1999.
Doling et al. Cytotoxic T-lymphocyte epitopes fused to anthrax toxin induce protective antiviral immunity, Infect. Immun. Jul. 1999; 67(7):3290-6.
Dominiecki et al. Tumor sensitivity to IFN-γ is required for successful antigen-specific immunotherapy of a transplantable mouse tumor model for HPV-transformed tumors; Cancer Immunol Immunother ;54(5):477-88 (2005).
Dons et al. "Cloning and characterization of a gene encoding flagellin of Listeria monocytogenes", Mol Microbiol. Oct. 1992;6(20):2919-29.
Dramsi et al., 1995, "Entry of Listeria monocytogenes into hepatocytes requires expression of inIB, a surface protein of the internalin multigene family", Mol. Microbiol. 16(2):251-61.
Dunn et al., 1991, "Selective radiation resistance of immunologically induced T cells as the basis for irradiation-induced T-cell-mediated regression of immunogenic tumor", J. Leukoc Biol. 49(4):388-396.
Dustoor, "Antitumor activity of listeria monocytogenes on a guinea pig fibrosarcoma", Infection and Immunity, 1979, vol. 23, No. 1, pp. 54-60.
Dzojic et al "Adenovirus-Mediated CD40 Ligand Therapy Induces Tumor Cell Apoptosis and Systemic Immunity in the Tramp-C2 Mouse Prostate Cancer Model" Prostate, Jun. 1, 2006;66(8):831-8).
Ebbeson et al. "Rhabdomyolysis, acute renal failure, and compartment syndrome in a child with parainfluenza type 1 infection", The Pediatric Infectious Disease Journal vol. 28, No. 9, Sep. 2009.
Ebert et al., 1990, "Selective immunosuppressive action of a factor produced by colon cancer cells", Cancer Res. 50(19):6158-6161.
Edman et al. A Protein Sequenator; Eur. J. Biochem . 80: 116-132, (1967).
Eisenhauer et al. New response evaluation criteria in solid tumours: Revised Recist guideline (version 1.1), Eur. J Cancer 45:228-247 (2009).
Emond et al. "A ribosomal DNA fragment of Listeria monocytogenes and its use as a genus-specific probe in an aqueous-phase hybridization assay", Appl Environ Microbiol. Aug. 1993;59(8):2690-7.

(56) References Cited

OTHER PUBLICATIONS

Ercolini et al., "Identification and characterization of the immunodominant rat HER-2/neu MHC class I epitope presented by spontaneous mammary tumors from Her-2/neu transgenic mice", Journal of Immunology, 2003, vol. 170, No. 8, pp. 4273-4280.
Everts et al. Selective Intracellular Delivery of Dexamethasone into Activated Endothelial Cells Using an E-Selectin-Directed Immunoconjugate; J. Immunol. 168:883-889 (2002).
Ezzel, 1995, "Cancer Vaccines: An Idea Whose Time Has Come?" J. NIH Res., 7:46-49.
Falk et al., 1991, "Identification of naturally processed viral nonapeptides allows their quantification in infected cells and suggests an allele-specific T cell epitope forecast" J. Exp. Med. 174(2):425-434.
Ferrari et al. "Isolation of an Alanine Racemase Gene from Bacillus subtilis and its Use for Plasmid Maintenance in B. subtilis", Nature Biotechnology 3, 1003-1007 (1985).
Finn et al., 2003, "Cancer vaccines: between the idea and the reality" Nature Reviews Immunology 3:630-641.
Flint et al. "Overexpression of the erbB-2 proto-oncogene in canine osteosarcoma cell lines and tumors", Vet. Pathol. 41: 291-296, 2004.
Foote et al. "Antibody Framework Residues Affecting the Conformation of the Hypervariable Loops", J. Mol. Biol. 224:487-499 (1992).
Fouts et al. "Construction and immunogenicity of *Salmonella typhimurium* vaccine vectors that express HIV-1 gp120", Vaccine. Dec. 1995;13(17):1697-705.
Frankel et al. "Induction of a cell-mediated immune responses to human immunodeficiency virus type 1 Gag protein by using Listeria monocytogenes as a live vaccine vector", J Immunol. Nov. 15, 1995;155(10):4775-82.
Frankel et al., "Induction of a Cell-Mediated Immune Response to HIV Gag Using Listeria Monocytogenes as a Live Vaccine Vector", J. Immunol. 155: 4766-4774. 1995.
Frey, 1993, "Rat adenocarcinoma 13762 expresses tumor rejection antigens but tumor-bearing animals exhibit tumor-specific immunosuppression", Clin. Immunol. Immunopathol. 69(2):223-233.
Friedman et al., 2000, "Induction of human immunodeficiency virus (HIV)-specific CD8 T-cell responses by Listeria monocytogenes and a hyperattenuated Listeria strain engineered to express HIV antigens" J. Virology 74 9987-9993.
Fu et al., 1990, "Expansion of Immunoregulatory macrophages by granulocyte-macrophage colony-stimulating factor derived from a murine mammary tumor", Cancer Res. 50(2):227-234.
Fuji, 1987, "Significance of suppressor macrophages for immunosurveillance of tumor-bearing mice" J. Natl. Cancer Inst. 78(3):509-517.
Furukawa, 1993, "Nude mouse metastatic models of human stomach cancer constructed using orthotopic implantation of histologically intact tissue" Cancer Res. 53(5):1204-1208.
Gadiot et al., "Overall Survival and PD-L1 Expression in Metastasized Malignant Melanoma" Cancer 117:2192-2201 (2011).
Galakatos et al. "Biosynthetic air alanine racemase from *Salmonella typhimurium*: DNA and protein sequence determination", Biochemistry. Jun. 3, 1986;25(11):3255-60.
Galen et al., 2001, "Can a 'flawless' live vector vaccine strain be engineered?", Trends Microbiol. 9(8):372-6.
Gao et al. Overexpression of PD-L1 Significantly Associates With Tumor Aggressiveness and Postoperative Recurrence in Human Hepatocellular Carcinoma. Clinical Cancer Research (2009) 15: 971-979.
Garay-Malpartida et al. "Caspredictor: A New Computer-Based Tool for Caspase Substrate Prediction", Bioinformatics. Jun. 2005;21 Suppl 1:I169-76.
GenBank Acc. No. NC_003210, Dec. 17, 2014.
Genbank Accession No. AF103807, Nov. 1, 1999.
GenBank Accession No. AY878649, Feb. 6, 2005.
GenBank Accession No. DQ054588, Aug. 21, 2006.
GenBank Accession No. DQ054589, Aug. 21, 2006.
GenBank Accession No. U25452, Jul. 16, 2001.

Gentschev et al. "*Salmonella* Strain Secreting Active Listeriolysin Changes Its Intracellular Localization", Infect. Immun., 1995, 63:4202-4205.
Gentschev et al. 1996, "Development of antigen-delivery systems, based on the *Escherichia coli* hemolysin secreatiohn pathway" Gene 179:133-140.
Ghebeh "FOXP3+ TREGS and B7-H1+/PD-1+ T Lymphocytes Co-Infiltrate the Tumor Tissues of High-Risk Breast Cancer Patients: Implication for Immunotherapy", BMC Cancer. Feb. 23, 2008;8:57.
Ghebeh et al. The B7-H1 (PD-L1) T Lymphocyte-Inhibitory Molecule Is Expressed in Breast Cancer Patients With Infiltrating Ductal Carcinoma: Correlation With Important High-Risk Propgnostic Factors. Neoplasia (2006) 8: 190-198.
Ghosh et al. "Natalizumab for Active Crohn's Disease" (2003) New Engl. J. Med. 348:24-32.
Giannini et al. Morphological Precursors of Hepatocellular Carcinoma: A Morphometrical Analysis; Hepatogastroenterol. 34:95-97 (1987).
Gibellini et al. Extracellular HIV-1 Tat Protein Induces the Rapid Ser 133 Phosphorylation and Activation of CREB Transcription Factor in Both Jurkat Lymphoblastoid T Cells and Primary Peripheral Blood Mononuclear Cells; J. Immunol. 160:3891-3898 (1998).
Gilbert et al. Enhanced CD8 T cell immunogenicity and protective efficacyin a mouse malaria model using a recombinant adenoviral vaccine in heterologous prime—boost immunization regimes; Vaccine 20:1039-45 (2002).
Gilman et al. "Isolation of sigma-28-specific promoters from Bacillus subtilis DNA" 1984, Gene 32:11-20.
Gilmore et al., 1989, "A Bacillus cereus cytolytic determinant, cereolysin AB, which comprises the phospholipase C and sphingomyelinase genes: nucleotide sequenc and genetic linkage", J. Bacteriol. Feb.; 171(2):744-53.
Gish, W et al. Identification of protein coding regions by database similarity search; Nature Genet. 3:266-272 (1993).
Glick, "Factors affecting the expression of foreign proteins in *Escherichia Coli*" 1987, J. Ind. Microbiol. 1:277-282.
Glomski et al., 2002, "The Listeria monocytogenes hemolysin has an acidic pH optimum to compartmentalize activity and pevent damage to infected host cells" J. Cell Biol. Mar. 18; 156(6):1029-38.
Goebel et al., 1993, "Listeria monocytogenes—a model system for studying the pathomechanisms of an intracellular microorganism", Zbl. Bakt. 278:334-347.
Gold et al., "Translational initiation in prokaryotes." 1981, Ann. Rev. Microbiol. 35:365-404.
Gonzalo et al. A heterologous prime—boost regime using DNA and recombinant vaccinia virus expressing the Leishmania infantum P36/LACK antigen protects BALB/c mice from cutaneous leishmaniasis; Vaccine 20:1226-31 (2002).
Goossens et al., 1992, "Induction of protective CD8+ T lymphocytes by an attenuated Listeria monocytogenes actA mutant" Int. Immunol. Dec.; 4(12):1413-8.
Goossens et al., 1995, "Attenuated Listeria monocytogenes as a live vector for induction of CD8+ T cells in vivo: a study with the nucleoprotein of the lymphocytic choriomeningitis virus", Int. Immunol. May; 7(5):797-805.
Gottesman, "Bacterial regulation: global regulatory networks.", 1984, Ann. Rev. Genet. 18:415-442.
Gouin et al. "The Listeria Monocytogenes LNLC Protein Interferes With Innate Immune Responses by Targeting the I B Kinase Subunit IKK", Proceedings of the National Academy of Sciences, vol. 107, No. 40, Sep. 20, 2010 (Sep. 20, 2010), pp. 17333-17338.
Graham et al. "Candidate AIDS vaccines", N Engl J Med. Nov. 16, 1995;333(20)1331-9.
Gregory et al., 1997, "Internalin B promotes the replication of Listeria monocytogenes in mouse hepatocytes" Infect. Immun. 65(12):5137-41.
Gunn et al. "Two Listeria Monocytogenes Vaccine Vectors That Express Different Molecular Forms of Human Papilloma Virus-16 E7 Induce Qualitatively Different T Cell Immunity That Correlated With Their Avility to Induce Regression of Established Tumors Immortalized by HPV-16", Journal of Immunology, vol. 167, No. 11, 2001, pp. 6471-6479.

(56) References Cited

OTHER PUBLICATIONS

Gunn et al., 2002, "Recombinant Intra-cellular Bacteria as Carriers for Tumor Antigens", In Vaccine Delivery Strategies, Chapter 14, Eds. Guido Dietrich and Werner Goebel, Horizon Scientific Press, UK.
Guzman et al. "Attenuated Listeria monocytogenes carrier strains can deliver an HIV-1 gp120 T helper epitope to MHC class II-restricted human CD4+ T cells", European Journal of Immunology, vol. 28, No. 6, Jun. 1998, pp. 1807-1814.
Hamanishi et al. Programmed Cell Death 1 Ligand 1 and Tumor-Infiltrating CD8+ T Lymphocytes Are Prognostic Factors of Human Ovarian Cancer. Proceeding of the National Academy of Sciences (2007): 104: 3360-3365.
Hancock et al. SIMPLE34: An Improved and Enhanced Implementation for VAX and Sun computers of the SIMPLE algorithm for analysis of clustered repetitive motifs in nucleotide sequences; Comput. Appl. Biosci. 10:67-70 (1994).
Harty et al. "CD8 T lymphocytes specific for the secreted p60 antigen protect against Listeria monocytogenes infection", J. Immunol. May 1, 1995; 154(9):4642-50.
Harty et al. "CD8+ T cells specific for a single nonamer epitope of Listeria monocytogenes are protective in vivo", J Exp Med. Jun. 1, 1992;175(6):1531-8.
Hassan et al., 2004, "Mesothelin: a new target for immunotherapy" Clin. Cancer Res. 10(12 Pt 1):3937-42.
Hauf et al., 1997, "Listeria monocytogenes infection of P388D1 macrophages results in a biphasic NF-kappaB (RelA/p50) activation induced by lipoteichoic acid and Bacterial phospholipases and mediated by IkappaBalpha and IkappaBbeta degradation", Proc. Natl. Acad. Sci. U.S.A. Aug. 19; 94(17):9394-9.
Haynes et al. "Scientific and social issues of human immunodeficiency virus vaccine development", Science. May 28, 1993;260(5112)1279-86.
Haynes et al. "Update on the issues of HIV vaccine development", Ann Med. Feb. 1996;28(1):39-41.
He et al. Humanization and Pharmacokinetics of a Monoclonal Antibody with Specificity for Both E—and P-Selectin; J. Immunol. 160:1029 (1998).
Heinrich jet al "Vaccination Against Prostate Cancer Using a Live Tissue Factor Deficient Cell Line in Lobund-Wistar Rats", Cancer Immunol Immunother 2007;56(5):725-30).
Henikoff et al. "Amino Acid Substitution Matrices From Protein Blocks" (1992) Proc. Natl. Acad. Sci. USA 89:10915-10919.
Herold et al. "Anti-CD3 Monoclonal Antibody in New-Onset Type 1 Diabetes Mellitus" (2002) New Engl. J. Med. 346:1692-1698.
Hess et al, "*Mycobacterium bovis* Bacille Calmette-Guerin strains secreting listeriolysin of Listeria monocytogenes", Proc. Natl. Acad. Sci. U.S.A. Apr. 28, 1998; 95(9):5299-304.
Hess et al. Abstract, "Live antigen carriers as tools for improved anti-tuberculosis vaccines", FEMS Immunol. Med. Microbiol. Feb. 1999; 23(2):165-73.
Hess et al., 1995, "Listeria monocytogenes p60 supports host cell invasion by and in vivo survival of attenuated *Salmonella typhimurium*" Infect. Immun. May; 63(5):2047-53.
Hess et al., 1996, "*Salmonella typhimurium* aroA—infection in gene-targeted immunodeficient mice: major role of CD4+ TCR-alpha beta cells and IFN-gamma in bacterial clearance independent of intracellular location" J. Immunol. May 1; 156(9):3321-6.
Hess et al., 1996, "Superior efficacy of secreted over somatic antigen display in recombinant *Salmonella* vaccine induced protection against listeriosis" Proc. Nat. Acad. Sci. 93:1458-1463.
Hess et al., 1997, "Protection against murine listeriosis by an attenuated recombinant *Salmonella typhimurium* vaccine strain that secretes the naturally somatic antigen superoxide dismutase", Infect. Immun. Apr.; 65(4):1286-92.
Higgins et al., 1998, "Bacterial delivery of DNA evolves" Nat. Biotechnol. Feb.; 16(2):138-9.
Higgins et al., Abstract, "Delivery of protein to the cytosol of macrophages using *Escherichia coli* K-12", Mol. Microbiol. Mar. 1999 31(6):1631-41.

Hiltbold et al. "Mechanisms of processing and presentation of the antigens of Listeria monocytogenes", Infect. Agents Dis. Oct. 1993; 2(5):314-23.
Hiltbold et al. "The presentation of class I and class II epitopes of listeriolysin O is regulated by intracellular localization and by intracelluar spread of Listeria monocytegenes", J. Immunol. Aug. 1, 1996; 157(3):1163-75.
Hino et al. Tumor Cell Expression of Programmed Cell Death-1 Is a Prognostic Factor for Malignant Melanoma. Cancer (2010 116(7):1757-66.
Hjortland et al., "Immunotoxin Treatment Targeted to the Higher-Molecular Weight Melanoma-Associated Antigen Prolonging the Survival of Immunodeficient Rats With Invasive Intracranial Human Glioblastoma Multiforme", J. Neurosurg. 2004, vol. 100, No. 2, pp. 320-327.
Hodgson 2000, "Generalized transduction of serotype 1/2 and serotype 4b strains of Listeria monocytogenes", Mol. Microbiol. 35(2):312-23.
Hoogenboom et al. "Natural and designer binding sites made by phage display technology", Immunol. Today 21:371-377 (2000).
Hsing et al. "Requirement for Nuclear Factor-kB Activation by a Distinct Subset of CD40-Mediated Effector Functions in B Lymphocytes", J. Immunol. 162:2804-2811 (1999).
Huang et al., 1994, "Role of bone marrow-derived cells in presenting MHC class I-restricted tumor antigens" Science 264:961-965.
Hussain et al., "What Is Needed for Effective Antitumor Immunotherapy? Lessons Learned Using Listeria Monocytogenes as a Live Vector for HPV-Associated Tumors", Cancer Immunology, Immunotherapy, vol. 54, No. 6, 2005, pp. 577-586.
Hussain et al., 2004, "CD4+CD25+ regulatory T cells that secrete TGFbeta and IL-10 are preferentially induced by a vaccine vector" J. Immunother. Sep.-Oct.; 27(5):339-46.
Ikonomidis et al. "Delivery of a viral antigen to the class I processing and presentation pathway by Listeria monocytogenes", J Exp Med. Dec. 1, 1994 ;180(6):2209-18.
Ikonomidis et al., "Influenza-specific immunity induced by recombinant Listeria monoctogenese vaccines", Vaccine, vol. 15, No. 4, 1997, pp. 433-440.
Ikonomidis et al., 1994, Abstract E-90, Abstracts, 94th General Meeting of the American society for Microbiology, May 23-27.
Inman et al. PD-L1 (B7-H1) Expression by Urothelial Carcinoma of the Bladder and BCG-Induced Granulomata: Associations With Localized Stage Progression. Cancer (2007): 109: 1499-1505.
International Search Report for PCT Application No. PCT/US12/28757 dated Aug. 27, 2012.
Jensen et al., 1997, "Recombinant Listeria monocytogenes as a live vaccine vehicle and a probe for studying-cell-mediated immunity" Immunological Review 158:147-157.
Jensen, 1997, "Recombinant Listeria monocytogenes vaccination eliminates papillomavirus-induced tumors and prevents papilloma formation from viral DNA", J. Virol. 71(11):8467-8474.
Jiang et al. "Characterization of a mutant Listeria monocytogenes strain expressing green fluorescent protein" Acta. Biochim. Biophys Sin (Shanghai), 37(1): 19-24, (2005).
Johnson et al., "Kabat Database and Its Applications: 30 Years After the First Variability Plot", Nucleic Acids Research, 2000, vol. 28, No. 1, pp. 214-218.
Jones et al., 1994, "Characterization of Listeria monocytogenes pathogenesis in a strain expressing perfingolysin O in place of listeriolysin O", Infect. Immun. 62:5608-5613.
Kabat "The Structural Basis of Antibody Complementarity", Adv. Prot. Chem. 32:1-75 (1978).
Kabat et al., "Unusual distributions of amino acids in complementarity-determining (hypervariable) segments of heavy and light chains of immunoglobulins and their possible roles in specificity of antibody-combining sites" (1977) J. Biol. Chem. 252:6609-6616.
Kaithamana et al. Induction of Experimental Autoimmune Graves' Disease in BALB/c Mice; J. Immunol. 163:5157-5164 (1999).
Karlin et al. "Methods for assessing the statistical significance of molecular sequence features by using general scoring schemes" (1990) Proc. Natl. Acad. Sci. USA 87:2264-2268.

(56) References Cited

OTHER PUBLICATIONS

Karlin et al., "Applications and Statistics for Multiple High-Scoring Segments in Molecular Sequences" (1993) Proc. Natl. Acad. Sci. USA 90:5873-5877.
Kaufman et al., "Impact of intracellular location of and antigen display by intracellular bacteria:implications for vaccine development", J. Immunol. Lett. 1999, 65(1-2):81-84.
Kaufmann "Immunity to intracellular bacteria", Annu Rev Immunol. 1993;11:129-63.
King et al. "Amplification of a novel v-erbB-related gene in a human mammary carcinoma" Science. 229:974-976, (1985).
Knutson et al., "Immunization with a HER-2/neu helper peptide vaccine generates HER-2/neu CD8 T-cell immunity in cancer patients." The Journal of Clinical Investegation, 107:477-484, 2001.
Kooks et al., 1992, "L monocytogenes-induced act in assembly requires the actA gene product", Cell, vol. 68, No. 3, p. 521-531.
Kohler et al. "Expression of the iap gene coding for protein p60 of Listeria monocytogenes is controlled on the posttranscriptional level", J Bacteriol. Aug. 1991;173(15):4668-74.
Kohler et al. Continuous Cultures of Fused Cells Secreting Antibody of Predefined Specificity; Nature 256: 495 (1975).
Kovacsovics-Bankowski et al., 1993, "Efficient major histocompatibility complex class I peresentation of exogenous antigen upon phagocytosis by macrophages", Proc. Natl. Acad. Sci. USA 90:4942-4946.
Kucera et al. "Prostate Specific Antigen (PSA) in Breat and Ovarian Cancer", Anticancer Res 1997, vol. 17, No. 60, pp. 4735-4737.
Kyte et al. "A Simple Method for Displaying the Hydropathic Character of a Protein", J Mol Biol. May 5, 1982;157(1):105-32.
Lampson et al., 1993, "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ", Cancer Research 53:176-182.
Landy "Mechanistic and Structural Complexity in the Site-Specific Recombination Pathways of INT and FLP", Curr Opin Genet Dev. Oct. 1993;3(5):699-707.
Lasa et al., 1997, "Identification of two regions in the N-terminal domain of ActA involved in the actin comet tail formation by Listeria monocytogenes" EMBO 16(7):1531-40.
Lauer et al. "Construction, Characterization, and Use of Two LM Site-Specific Phage Integration Vectors", J Bacteriol 2002;184(15):4177-86.
Lauer et al., "Characterization of the Attachment Site of Bacteriophage U153 within the Listeria monocytogenes comK Gene" ASM Meeting, Abstract 1999.
Le Doussal et al. Enhanced In Vivo Targeting of an Asymmetric Bivalent Hapten Antibody Conjugate CocktailsTo Double-Antigen-Positive Mouse B Cells With Monoclonal ; J. Immunol. 146:169-175 (1991).
Leao et al., 1995, "A species-specific nucleotide sequence of *Mycobacterium tuberculosis* encodes a protein that exhibts hemolytic activity when expressed in *Escherichia coli*" Infect. Immun. Nov.; 63(11):4301-6.
Lebrun et al., Aug. 1996, "Internallan must be on the Bacterial Surface to mediate Entry of Listeria monocytogenes into Epilhalial Cells", Molecullar Microbiology 21:579-592.
Lee et al. Delivery of macromolecules into cytosol using liposomes containig hemolysin from Listeria monocytogenes, J. Biol. Chem., Mar. 29, 1996, 271(13):7249-52.
Lee et al., 1991, "Construction of single-copy integration vectors for *Staphylococcus aureus*", Gene 103:101-5.
Lehner et al., 1996, "Processing and delivery of peptides presented by MHC class I molecules", Curr. Opin. Immunol. 8(1):59-67.
Lejeune, 1994, "Nitric oxide involvement in tumor-induced immunosuppression" J. Immunol. 152(10):5077-5083.
Lenz "Stable integration vector for nutrient broth-based selection of attenuated Listeria monocytogenes strains with recombinant antigen expression", Clin Vaccine Immunol. 15(9):1414-1419. Sep. 2008.

Li et al. "Conditional Lethality Yields a New Vaccine Strain of Listeria Monocytogenes for the Induction of Cell-Mediated Immunity", Infection and Immunity, 2005, 73(8): 5065-5073.
Liau et al., 2002, "Tumor immunity within the central nervous system stimulated by recombinant Listeria monocytogenes vaccination", Cancer Res., 62(8):2287-93.
Lieberman et al. "Engineered Listeria monocytogenes as an AIDS vaccine", Vaccine. May 6, 2002;20(15):2007-10.
Lin et al., "Treatment of Established Tumors with a Novel Vaccine that Enhances Major Histocompatibility Class II Presentation of Tumor Antigen", Cancer Res. 1996, 56:21-26.
Lin et al., 2002, "Oral vaccination with recombinant Listeria monocytogenes expressing human papillomavirus type 16 E7 can cause tumor growth in mice to regress" Int. J. Cancer, Dec. 20; 102(6):629-37.
Lingnau et al., 1995, "Expression of the Listeria monocytogenes EGD inlA and inlB genes, whose products mediate bacterial entry into tissue culture cell lines, by PrfA-dependent and independent mechanisms" Infect. Immun. Oct.; 63(10):3896-903.
Lipford et al. "Vaccination with immunodominant peptides encapsulated in Quil A-containing liposomes induces peptide-specific primary CD8+ cytotoxic T cells", Vaccine Jan. 1994; 12(1):73-80.
Lipsky et al. "Infliximab and Methotrexate in the Treatment of Rheumatoid Arthritis" (2000) New Engl. J. Med. 343:1594-1602.
Liu et al. "Randomised, double blind, placebo controlled study of interferon beta-1a in relapsing-remitting multiple sclerosis analysed by area under disability/time curves" (1999) J. Neurol. Neurosurg. Psych. 67:451-456.
Lobocka et al. "Organization and expression of the *Escherichia coli* K-12 dad operon encoding the smaller subunit of D-amino acid dehydrogenase and the catabolic alanine racemase", J Bacteriol. Mar. 1994;176(5):1500-10.
Loeffler et al., 2006, "Comparison of different live vaccine strategies in vivo for delivery of protein antigen or antigen-encoding DNA and mRNA by virulence-attenuated Listeria monocytogenes" Infect. Immun. Jul; 74(7):3946-57.
Loessner et al., 1994 "Structural Proteins and DNA Characteristics of 14 Listeria Typing Bacteriophages", J. Gen. Virol. 75:701-710.
Loessner et al., 1995, "Heterogeneous endolysins in Listeria monocytogenes bacteriophages: a new class of enzymes and evidence for conserved holin genes within the siphoviral lysis cassettes", Mol. Microbiol. Jun.; 16(6):1231-41.
Loessner et al., 2000, "Complete nucleotide sequence, molecular analysis and genome structure of bacteriophage A118 of Listeria monocytogenes: implications for phage evolution", Molecular Microbiology 35(2):324-40.
Ma et al. "Expressionof HER 2 in HumanOsteosarcoma", Science Technology and Engineering vol. 11 No. 13 (2011): 3045-3048.
Maciag et al. "The first clinical use of a live-attenuated Listeria monocytogenes vaccine: a Phase I safety study of Lm-LLO-E7 in patients with advanced carcinoma of the cervix", Vaccine. Jun. 19, 2009;27(30):3975-83.
Madden et al. Applications of Network BLAST Server; Meth. Enzymol. 266:131-141 (1996).
Makela et al., Hand book of Experimental Immunology vol. 1, Chapter 3—"Haptens and carriers", pp. 3.1-3.13; 1987.
Manjili et al., 2003, "HSP110-HER2/neu chaperone complex vaccine induces protective immunity against spontaneous mammary tumors in HER-2/neu trangenic mice" J. Immunol. Oct. 15; 171(8):4054-61.
Marks et al. By-passing Immunization Human Antibodies from V-gene Libraries Displayed on Phage; J. Mol. Biol. 222: 581-597 (1991).
Marquis et al. "Intracytoplasmic growth and virulence of Listeria monocytogenes auxotrophic mutants", Infect Immun. Sep. 1993;61(9):3756-60.
Marquis et al., 1997, "Proteolytic pathways of activation and degradation of a bacterial phospholipase C during intracellular infection by Listeria monocytogenes" J. Cell Biol. 137:1381-1392.
Martin et al., 1986, "Nucleotide sequence of the tetM tetracycline resistance determinant of the streptococcal conjugative shuttle transposon Tn1545", Nucleic Acid Res. 14:7047-7058.

(56) References Cited

OTHER PUBLICATIONS

Marx et al., 2002, "Broad-host-range cre-lox system for antibiotic marker recycling in gramnegativ bacteria" Biotechniques, Nov.; 33(5):1062-7.
Mata et al. "A Hexameric Phosphorothioate Oligonucleotide Telomerase Inhibitor Arrests Growth of Burkitt's Lymphoma Cells In Vitro and In Vivo", Toxicol Appl Pharmacol. May 1997;144(1):189-97.
Mata et al. "Evaluation of a Recombinant Listeria Monocytogenes Expressing an HIV Protein That Protects Mice Against Viral Challenge", Vaccine 19:1435-45, 2001.
Mata et al. Th1 T.cell responses to HIV-1 Gag protein delivered by Listeria monocytogenes vaccine are similar to those induced by endogenous listerial antigen's; J. Immunol 163:1449-1456. (1999).
Mazda et al. (1997) "Extremely Efficient Gene Transfection Into Lympho-Hematopoietic Cell Lines by Epstein-Barr Virus-Based Vectors", J. Immunol. Methods 204, 143-151.
Mazzaccaro et al. "Major histocompatibility class I presentation of soluble antigen facilitated by *Mycobacterium tuberculosis* infection", Proc. Natl. Acad. Sci. U.S.A. Oct. 15, 1996; 93(21):11786-91.
McLaughlan et al., 1998, "Molecular characterization of an autolytic amidase of Listeria monocytogenes EGD", Microbiology, May; 144(Pt 5):1359-67.
Mendez et al. Functional Transplant of Megabase Humanimmunoglobulin Loci Recapitulates Human Antibody Response in Mice; Nature Genetics 15:146-156 (1997).
Mengaud et al. "Transcriptional mapping and nucleotide sequence of the Listeria monocytogenes hlyA region reveal structural features that may be involved in regulation", Infect Immun. Dec. 1989;57(12):3695-701.
Mengaud et al., 1988, "Expression in *Escherichia coli* and sequence analysis of the listeriolysin O determinant of listeria monocytogenes", Infect. Immun., vol. 56, No. 4, 766-772.
Menne et al. "A Comparison of Signal Sequence Predition Methods Using a Test Set of Signal Peptides" (2000) Bioinformatics 16: 741-742.
Merrifield et al., "Solid phase peptide synthesis. 1. The synthesis of a tetrapeptide" J. Am. Chem. Soc., 85:2149-2156 (1963).
Meyaard et al. "Lair-1, A Novel Inhibitory Receptor Expressed on Human Mononuclear Leukocytes" (1997) Immunity 7:283-290.
Mikayama et al. "Molecular cloning and functional expression of a cDNA encoding gycosylation-inhibiting factor", Nov. 1993, Pro Natl. Acad. Sci., USA, vol. 90:10056-10060.
Milgrom et al. "Treatment of Allergic Asthma With Monoclonal Anti-Ige Antibody" (1999) New Engl. J. Med. 341:1966-1973.
Miller et al, "Targeted Vectors for Gene Therapy" 1995, FASEB J., 9:190-199.
Milligan (1993) "Current Concepts in Antisense Drug Design", J. Med. Chem. 36:1923-1937; Antisense Research and Applications (1993, CRC Press).
Mkrtichyan et al. "Anti-PD-1 Antibody Significantly Increases Therapeutic Efficacy of Listeria Monocytogenes (LM)-LLO Immunotherapy", Journal for Immunotherapy of Cancer 2013, 1:15.
Mlynarova et al., 2002, "The promiscuity of heterospecific lox sites increases dramatically in the presence of palindromic DNA", Gene, Aug. 21; 296(1-2):129-37.
Mollet et al., 1993, "Directed genomic integratoin, gene replacement, and integrative gene expression in *Streptococcus thermophilus*" J. Bacteriology 175:4315-4324.
Moriishi et al., 1998, "Sequence analysis of the actA gene of Listeria monocytogenes isolated from human", Microbiol. Immunol., vol. 42, No. 2, p. 129-132.
Myoung-Song et al. "Coexpression of BIP Increased Antithrombotic Hirudin Production in Recombinant *Saccharomyces cerevisiae*", Journal of Biotechnology, vol. 101, No. 1, pp. 81-87, 2003.
Nagai et al 1991 Isolation and Partial Characterization of Major Protein Antigens in the Culture Fluid of *Mycobacterium tuberculosis*. Infect Immun. Jan. 1991;59(1):372-82.

Nakanuma, et al. Anatomic and Molecular Pathology of Intrahepatic Cholangiocarcinoma, J. Hepatobiliary Pancreat. Surg. 10:265-281 (2003).
Narang et al. "Improved phosphotriester method for the synthesis of gene fragments", 1979, Meth. Enzymol. 68:90-99.
Naruishi et al. "Adenoviral Vector-Mediated RTVP-1 Gene-Modified Tumor Cell-Based Vaccine Suppresses the Development of Experimental Prostate Cancer", Cancer Gene Ther. Jul. 2006;13(7):658-63).
Naz et al., "Novel human prostate-specific cDNA: molecular cloning, expression, and immunobiology of the recombinant protein", Biochem Biophys Res. Commun. 297:1075-84, 2002.
Ngo et al., 1994, "The Protein Folding Problem and Tertiary Structure Prediction", pp. 492-495.
Nielsen "Peptide Nucleic Acids as Therapeutic Agents", Curr Opin Struct Biol. Jun. 1999;9(3):353-7.
Nikodinovic et al "A Second Generation SNP-Derived *Escherichia coli*-Streptomyces Shuttle Expression Vector That Is Generally Transferable by Conjugation", Plasmid. Nov. 2006;56(3):223-7.
Nitcheu-Tefit et al. "Listeriolysin O Expressed in a Bacterial Vaccine Suppresses CD4_CD25HIGH Regulatory T Cell Function In Vivo", J Immunol. Aug. 1, 2007;179(3):1532-41.
Nomi et al. Clinical Significance and Therapeutic Potential of the Programmed Death-1 Ligand/Programmed Death-1 Pathway in Human Pancreatic Cancer. Clinical Cancer Research (2007);13:2151-2157.
Noriega et al. "Engineered deltaguaB-A deltavirG Shigella flexneri 2a strain CVD 1205: construction, safety, immunogenicity, and potential efficacy as a mucosal vaccine", Infect Immun. Aug. 1996;64(8):3055-61.
Ochsenbein et al., 1999, "A comparison of T cell memory against the same antigen induced by virus versus intracellular bacteria" Proc. Natl. Acad Sci U.S.A. Aug. 3; 96(16):9293-8.
Office Action dated Jun. 14, 2016 for Japanese Application No. 2014-526219.
Offit et al. "Addressing Parents' Concerns: Do Multiple Vaccines Overwhelm or Weaken the Infant's Immune System?", Pediatrics vol. 109 No. 1 Jan. 2002.
Ogasawara et al "A strategy for making synthetic peptide vaccines", Proc Natl Acad Sci U S A. Oct. 1, 1992;89(19):8995-9.
Ohigashi et al. Clinical Significance of Programmed Death-1 Ligand-1 and Programmed Death-1 Ligand 2 Expression in Human Esophageal Cancer. Clin. Cancer Research (2005): 11:2947-2953.
O'Riordan, et al. Listeria Intracellular Growth and Virulence Require Host-Derived Lipoic Acid, Science 302: 462-464(2003).
Oscarsson et al., 1996, "Induction of haemolytic activity in *Escherichia coli* by the slyA gene product" Mol. Microbiol. Apr.; 20(1):191-9.
Paglia et al., 1997, "The defined attenuated Listeria monocytogenes delta mp12 mutant is an effective oral vaccine carrier to trigger a long-lasting immune response against a mouse fibrosarcoma" Eur. J. Immunol. 27:1570-1575.
Palmeros et al., 2000, "A family of removable cassettes designed to obtain antibiotic-resistance-free genomic modifications of *Escherichia coli* and other bacteria" Gene, Apr. 18; 247(1-2):255-64.
Pamer et al. "Precise prediction of a dominant class I MHC-restricted epitope of Listeria monocytogenes", Nature. Oct. 31, 1991;353(6347):852-5.
Pan et al., "Regression of Established Tumors in Mice Mediated by the Oral Administration of a Recombinant Listeria monocytogenes Vaccine", Cancer Res., 1995, 55:4776-4779.
Pan et al., 1995, "A recombinant Listeria monocytogenes vaccine expressing a model tumour antigen protects mice against lethal tumour cell challenge and causes regression of established tumours" Nature Med. 1:471-477.
Parida et al., 1998, "Internalin B is essential for adhesion and mediates the invasion of Listeria monocytogenes into human endothelial cells" Mol. Microbiol. Apr.; 28(1):81-93.
Parsa et al. "Engineering Bacterial Vectors for Delivery of Genes and Proteins to Antigen-Presenting Cells", Molecular Pharmaceutics, vol. 4, No. 1, 2007, pp. 4-17.

(56) References Cited

OTHER PUBLICATIONS

Passos et al. Recombinant Leishmania Antigens for Serodiagnosis of Visceral Leishmaniasis Clinical and Diagnostic Laboratory Immunology, Oct. 2005, p. 1164-1167, vol. 12, No. 10.

Paterson et al. "Listeria-Based Vaccines for Cancer Treatment", Current Opinion in Molecular Therapeutics, vol. 7, No. 5, 2005, pp. 454-460.

Paterson et al. "Recombinant Listeria monocytogenes cancer vaccines", Curr Opin Immunol. Oct. 1996;8(5):664-9.

Paterson, "Rational approaches to immune regulation", Immunologic Research, 2003; 27/2-3:451-462.

Paul et al. An IL-4 Receptor Region Containing an Insulin Receptor Motif Is Important for IL+Mediated IRS-1 Phosphorylation and Cell Growth, Cell 76 241-251 (1994).

Paul et al. Frequent associations between CTI and T-Helper epitopes in HIV-1 genomes and 12, 13 implications for multi-epitope vaccine designs. BMC Microbiology 10:1-16 (2010).

Paul et al., 1989, "Fundamental Immunology", Second Edition, Raven Press, 987-988.

Pawelek et al. "Tumor-targeted *Salmonella* as a novel anticancer vector", Cancer Res. Oct. 15, 1997;57(20):4537-44.

Peng et al. "Adjuvant Properties of Listeriolysin O in a DNA Vaccine Strategy", Cancer Immunol Immunother, Jun. 2007;56(6):797-806.

Penichet et al., 2001, "Antibody-cytokine fusion proteins for the therapy of cancer" J. Immunological Methods 248:91-101.

Peters et al. "Enhancing the immunogenicity of bioengineered Listeria monocytogenes by passaging through live animal hosts", Vaccine. 21.:1187-94. (2003).

Peters et al. "Tailoring host immune responses to Listeria by manipulation of virulence genes—the interface between innate and acquired immunity", FEMS Immunol Med Microbiol. Apr. 1, 2003;35(3):243-53.

Peters et al. The Induction of HIV Gag-Specific CD8+ T Cells in the Spleen and Gut-Associated Lymphoid Tissue by Parenteral or Mucosal monocytogenes HIV Gag Immunization with Recombinant Listeria; J Immunol; 170:5176-5187 ( 2003).

Pfeifer et al., 1993, "Phagocytic processing of bacterial antigens for class I MHC presentation to T cells" Nature, Jan. 28; 361(6410):359-62.

Portielji et al. IL-12: a promising adjuvant for cancer vaccination, Cancer Immunol. Immunother. 52:133-144 (2003).

Portnoy et al. "Molecular determinants of Listeria monocytogenes pathogenesis", Infect Immun. Apr. 1992;60(4):1263-7.

Presta "Selection, Design, and Engineering of Therapeutic Antibodies" (2005) J. Allergy Clin. Immunol. 116:731.

Pucci et al, "*Staphylococcus haemolyticus* Contains Two D-Glutamic Acid Biosynthetic Activities, a Glutamate Racemase and a D-Amino Acid Transaminase" 1995, J Bacteriol. 177: 336-342.

Pupa et al., 2001, "Prevention of spontaneous neu-expressing mammary tumor development in mice transgenic for rat proto-neu by DNA vaccination" Gene Ther. Jan.; 8(1):75-9.

Purchio et al. "Methods in Enzymology: Methods for Molecular Cloning in Eukaryotic Cells", (2003).

Quenee et al., 2005, "Combined sacB-based negative selection and cre-lox antibiotic marker recycling for efficient gene deletion in pseudomonas aeruginosa", Bioetechniques, Jan.;38(1):63-7.

Raveneau et al., 1992, "Reduced virulence of a Listeria monocytogenes phospholipase-deficient mutant obtained by transposon insertion into the zinc metalloproteas gene" Infect. Immune., 60:916-921.

Realini et al., "Proposed roles in protein-protein association and presentation of peptides by MHC Class I receptors", FEBS Lett., 1994, 348:109-113.

Rechsteiner et al. "Pest Sequences and Regulation by Proteolysis", Trends Biochem Sci 1996; 21(7):267-71.

Reiter et al., 1989, "Transfer RNA genes frequently serve as integration sites for porkaryotic genetic elements", Nucleic Acids Research 17(5):1907-14.

Renard et al., "HER-2 DNA and protein vaccines containing potent Th cell epitopes induce distinct protective and therapeutic antitumor responses in HER-2 transgenic mice", The Journal of Immunology, 171(3):1588-1595, 2003.

Repique, 1992, "Immunosuppression derived from human B-lymphoblastoid and melanoma cell lines" Cancer Invest. 10(3):201-208.

Riegler. Preneoplastic Conditions of the Liver; Seminars in Gastrointestinal Disease vol. 7, No. 2:pp. 74-87 (1996).

Riera et al. Evaluation of a latex agglutination test (KAtex) for detection of Leishmania antigen in urine of patients with HIV-Leishmania coinfection: value in diagnosis and post-treatment follow-up. Eur J Clin Microbiol Infect Dis. Dec;23 (12):899-904 (2004).

Robinson et al. "New Hope for an Aids Vaccine", Nat. Rev. Immunol. 2:239-50 (2002).

Rocken et al. "Pathalogy and Pathogenesis of Hepatocellular", Digestive Diseases 19:269-278 (2001).

Roden et al., 2004, "Vaccination to prevent and treat cervical cancer", Hum. Pathol. 35(8):971-82.

Rogers et al. "Amino Acid Sequences Common to Rapidly Degraded Proteins: The Pest Hypothesis", Science 1986; 234(4774):364-8.

Rongcun, Yang, et al. "Identification of new HER2/neu-derived peptide epitopes that can elicit specific CTL against autologous and allogeneic carcinomas and melanomas." The Journal of Immunology 163.2 (1999): 1037-1044.

Rothman et. al. "The Use of Living Listeria Monocytogenes As an Active Immunotherapy for the Treatment of Cancer", Emerging Cancer Therapy: Microbial Approaches and Biotechnological Tools, Edited by Arsénio M. Fialho and Ananda M. Chakrabarty Copyright © 2010 John Wiley & Sons, Inc..

Rubin et al. "Cloning, Sequence Determination, and Regulation of the Ribonucleotide Reductase Subunits From Plasmodium Falciparum: A Target for Antimalarial Therapy", Proc Natl Acad Sci U S A. Oct. 15, 1993;90(20):9280-4.

Russmann et al., 1998, "Delivery of epitopes by the *Salmonella* type III secretion system for vaccine system for vaccine development", Science, Jul. 24; 281(5376):565-8.

Safley et al. "Role of listeriolysin-O (LLO) in the T lymphocyte response to infection with Listeria monocytogenes. Identification of T cell epitopes of LLO" J. Immunology 146(10):3604-3616; May 1991.

Sambrook et al. "Molecular Cloning: A Laboratory Manual", Cold Spring Harbor Laboratory Press, Cold Spring Harbor, New York 2 (2001).

Samstag et al. "Synthesis and Properties of New Antisense Oligodeoxynucleotides Containing Benzylphosphonate Linkages", Antisense Nucleic Acid Drug Dev. 1996 Fall;6(3):153-6.

Schafer et al. "Induction of a Cellular Immune Response to a Foreign Antigen by a Recombinant Listeria Monocytogenes Vaccine", J Immunol. Jul. 1, 1992;149(1):53-9.

Scheirlinck et al., 1989, "Integration and expression of alpha-amylase and endoglucanase genes in the Lactobacillus plantarum chromosome", Appl. Environ. Microbiol. 55(9):21130-7.

Scher et al., (2008) "Design and End Points of Clinical Trials for Patients With Progressive Prostate Cancer and Castrate Levels of Testosterone: Recommendations of the Prostate Cancer Clinical Trials Working Group" J. Clin. Oncol. 26(7):1148-159.

Schmidt et al., 1995, "Molecular Analysis of the Plasmid-Encoded Hemolysin of *Escherichia coli* O157:H7 Strain EDL 933", Infection and Immunity, 63(3):1055-1061.

Schneider et al. Induction of CD8+ T cells using heterologous prime-boost immunisation strategies, Immunol.Rev. 170:29-38 (1999).

Schnupf et al. "Listeriolysino: A Phagosome-Specific Lysine", Microbes & Infect. 2007, 9:1176-1187.

Schnupf et al., "Phosphorylation, ubiquitination and degradation of listeriolysic O in mammalian cells: role of the PEST-like sequence" Cellular microbiology 8(2):353-364, 2006.

Scortti et al., 2007, "The PrfA virulence regulon", Microbes Infect. Aug.; 9(10):1196-207.

(56) References Cited

OTHER PUBLICATIONS

Scott, P. et al. Amino Acid Sequences Common to Rapidly Degraded Proteins: The PEST Hypothesis; Immunol. Today vol. 234 364-348.,(1991).
Seavey "A novel human Her-2/neu chimeric molecule expressed by Listeria monocytogenes can elicit potent HLA-A2 restricted CD8-positive T cell responses and impact the growth and spread of Her-2/neu-positive breast tumors" Clin Cancer Res. 15(3):924-32, Feb. 1, 2009.
Sehgal et al "Prostate Cancer Cells Show Elevated Urokinase Receptor in a Mouse Model of Metastasis" Cancer Cell Int. Aug. 23, 2006;6:21.
Sewell et al. Regression of HPV-Positive Tumors Treated with a New Listeria monocytogenes Vaccine Arch Otolaryngol., Head Neck Surg., Jan. 2004, vol. 130, pp. 92-97.
Sewell et al., "Recombinant Listeria Vaccines Containing Pest Sequences Are Potent Immune Adjuvants for the Tumor-Associates Antigen Human Pappilomavirus-16 E7", Cancer Research, American Association for Cancer Research, vol. 64, No. 24, 2004, p. 8821-8825.
Shahabi et al. "A Live, Attenuated Listeria-Based Immunotherapeutic for the Treatment of Breast Cancer", 2009 ASCO Breast Cancer Symposium, Oct. 8, 2009, Abstract.
Shahabi et al. "Development of a Live and Highly Attenutated Listeria Monocytogenes-Based Vaccine for the Treatment of HER2/NEU-Overexpressing Cancers in Human", Cancer Gene Therapy, vol. 18, No. 1, Jan. 1, 2011, pp. 53-62.
Shahabi et al. "Development of a Live and Highly Attenuated Listeria Monocytogenes-Based Vaccine for the Treatment of HER2/Neu-Overexpressing Cancers in Human", Cancer Gene Therapy, 2010, pp. 1-10.
Shahabi et al. "Live, Attenuated Strains of Listeria and *Salmonella* as Vaccine Vectors in Cancer Treatment", Bioeng. Bugs, 2010, vol. 1, No. 4, p. 235-243.
Shahabi et al., "Development of a Listeria Monocytogenes Based Vaccine Against Prostate Cancer" Cancer Immunol Immunother (2008) 57:1301-1313.
Sharpe et al. "The Function of Programmed Cell Death 1 and Its Ligands in Regulating Autoimmunity and Infection", Nature Immunology ; 8:239-245 (2007).
Shaw et al. "Complete Nucleotide Sequence of Macrolide-Lincosamide-Streptogramin B-Resistance Transposon TN917 in *Streptococcus faecalis*", J Bacteriol. Nov. 1985; 164(2):782-96.
Shen et al., 1995, "Recombinant Listeria monocytogenes as a live vaccine vehicle for the induction of protective anti-viral cell-mediated immunity" Proc. Nat'l Acad Sci U.S.A., 92(9):3987-91.
Shen et al., 1998, "Compartmentalization of bacterial antigens: diffrential effects on priming of CD8 T cells and protective immunity" Cell., Feb. 20; 92(4):535-45.
Shetron-Rama et al., 2002, "Intracellular induction of Listeria monocytogenes actA expression" Infect. Immun. 70:1087-1096.
Shimauchi et al. Augmented expression of programmed death-1 in both neoplasmatic and nonneoplastic CD4+ T-cells in adult T-cell Leukemia/ Lymphoma. Int. J. Cancer (2007): 121:2585-2590.
Shimizu et al., 1994, "Effects of CD4+ and CD8+ T cells in tumor-bearing mice on antibody production" Cancer Immunol. Immunother 38(4):272-276.
Shiver et al., Replication-Incompetent Adenoviral Vaccine Vector Elicits Effective Antiimmunode ®Ciency-Virus Immunity, Nature 415: 331-5 (2002).
Sin et al. DNA Priming—Protein Boosting Enhances Both Antigen-Specific Antibody and TH1-Type Cellular Immune Responses in a Murine Herpes Simplex Virus-2 GD Vaccine Model, DNA Cell Biol. 18:771-9 (1999).
Singh "Fusion to Listeriolysin O and Delivery by Listeria monocytogenes Enhances the Immunogenicity of HER-2/neu and Reveals Subdominant Epitope in the FVB/N Mouse", J. Immunology, Sep. 15, 2005, vol. 175, pp. 3663-3673.
Singh et al. "Cancer Immunotherapy Using Recombinant Listeria Monocytogenes Transition From Bench to Clinic", Human Vaccines, 2011, vol. 7(5), pp. 497-505.
Singh et al. Immunoediting Sculpts Tumor Epitopes During Immunotherapy Cancer Res;67:1887-1892.(2007).
Sirard et al., 1997, "Intrtracytoplasmic delivery of Lidteriolysin O by vaccinal strain of Bacillus anthracis induces CD8-mediated protection against listeria monocytogenes", J. Immunology, vol. 159, p. 4435-4443.
Sizemore et al. "Attenuated Shigella as a DNA Delivery Vehicle for DNA-Mediated Immunization", Science. Oct. 13, 1995;270(5234):299-302.
Skoble et al., Aug. 7, 2000, "Three Regions within ActA Promote Atp2/3 Complex-mediated Actin Nucleation and Listeria monocytogenes Motility", The Journal of cell Biology 150(3):527-537.
Skolnick et al. "Form genes to protein structure and function: novel applications of computational approaches in the genomic era", Jan. 2000, Trends in Biotech., 18(1):34-39.
Slamon et al. "Use of Chemotherapy Plus a Monoclonal Antibody Against HER2 for Metastatic Breast Cancer That Overexpresses HER2" 2001, New Engl. J. Med. 344:783-792.
Slifka et al., 1996, "Antiviral cytotoxic T-cell memory by vaccination with recombinant Listeria monocytogenes" J. Virol. 70(5):2902-10.
Smith et al. "Use of a New Integrational Vector to Investigate Compartment-Specific Expression of the Bacillus Subtilis Spoiim Gene", Biochimie. Jul.-Aug. 1992;74(7-8):705-11.
Smith et al., 1995, "The two distinct phospholipases C of Listeria monocytogenes have overlapping roles in escape from a vacuole and cell-to-cell spread", Infect. Immun. 63:4231-4237.
Smith et al., Sep. 1995, "Asymmetric Distribution of the Listeria monocytogenes ActA Protein is Required and Sufficient to Direct Actin-Based Motility", Molecular Microbiology 17:945-951..
Souders et al., 2006, "In vivo bactofection: listeriacan function as a DNA-cancer vaccine" DNA Cell Biol. Mar.; 25(3):142-51.
Soussi et al. "Effect of Intragastric and Intraperitoneal Immunization With Attenuated and Wild-Type Lack-Expressing Listeria Monocytogenes on Control Murine Leishmania Major Infection", Vaccine, vol. 20, No. 21-22, pp. 2702-2712, 2002.
Soussie et al. "Listeria Monocytogenes as a Short Lived Delivery System for the Induction of Type 1 Cell-Mediated Immunity Againdt the P36/Lack Antigen of Leishmania Major", Infection and Immunity, vol. 68, No. 3, 2000, pp. 1498-1506.
Stahl et al., 1984, "Replacement of the Bacillus subtilisin structural gene with an in vitro-derived deletion mutation", J. Bacteriol. 158:411-418.
States, D.J. et al. Improved Sensitivity of Nucleic Acid Database Searches Using Application-Specific Scoring Matrices, Methods 3:66-70 (1991).
Stitz et al., 1990, "Characterization and immunological properties of influenza A virus nucleoprotein (NP): cell-associated NP isolated from infected cells or viral NP expressed by vaccinia recombinant virus do not confer protection" J. Gen. Virol., 71(Pt 5):1169-1179.
Strauss-Soukup et al. "Effects of Neutralization Pattern and Stereochemistry on DNA Bending by Methylphosphonate Substituions", Biochemistry. Jul. 22, 1997;36(29):8692-8.
Strungnell et al., 1990, "Stable expression of forgein antigens from the chromosome of *Salmonella typhimurium* vaccine strains", Gene 88:57-63.
Strych et al, "Mutant Analysis Shows That Alanine Racemases From Pseudomonas Aeruginosa and *Escherichia coli* Are Dimeric" 2002, J. Bacteriol. 184:4321-4325.
Strych et al. "Characterization of the alanine racemases from two mycobacteria", FEMS Microbiol Lett. Mar. 15, 2001;196(2):93-8.
Stryer et al., "Levels of structure in protein architecture", Biochemistry, Third Edition, W H Freeman Company, New York, pp. 31-33, 1998.
Su et al. "Relevance of Hepatic Preneoplasia for Human Hepatocarcinogenesis" (2003) Toxicol. Pathol. 31:126-133.
Sun et al. "Isolation of Listeria Monocytogenes Small-Plaque Mutants Defective for Intracellular Growth and Cell-To-Cell Spread", Infect Immun. Nov. 1990;58(11):3770-8.

(56) References Cited

OTHER PUBLICATIONS

Supplementary European Search Report for European Application No. 12758350.8 dated Aug. 14, 2014.
Szalay et al. "Presentation of Listeria monocytogenes antigenes by major histocompatibility complex class I molecules to CD8 cytotoxic T lymphocytes independent of listeriolysin secretion and virulence", Eur. J. Immunol. Jul. 1994;24(7):1471-7.
Tanabe et al., "Induction of Protective T Cells against Listeria monocytogenes in Mice by Immunization with a Listeriolysin O-Negative Avirulent Strain of Bacteria and Liposome-Encapsulated Listeriolysin O", Infect. Immun., 1999, 67(2):568-575.
Tang et al. "Protein Chemistry and Structure: Use of a Peptide Mimotope to Guide the Humanization of MRK-16, an Anti-P-Glycoprotein Monoclonal Antibody", 1999 J. Biol. Chem. 274:27371-27378.
Tanghe "Improved Immunogenicity and Protective Efficacy of a Tuberculosis DNA Vaccine Encoding AG85 by Protein Boosting" Infect. Lmmun. 69:3041-7 (2001).
Tanizawa et al. "The primary structure of thermostable D-amino acid aminotransferase from a thermophilic Bacillus species and its correlation with L-amino acid aminotransferases", J Biol Chem. Feb. 15, 1989;264(5):2450-4.
Tanizawa et al. "Thermostable alanine racemase from Bacillus stearothermophilus: DNA and protein sequence determination and secondary structure prediction", Biochemistry. Feb. 23, 1988;27(4):1311-6.
Taube, J. M. et al. Colocalization of Inflammatory Response with B7-H1 Expression in Human Melanocytic Lesions Supports an Adaptive Resistance Mechanism of Immune Escape, Sci Transl Med 4, 127ra37 (2012).
Tauch et al. "The Alanine Racemase Gene ALR Is an Alternative to Antibiotic Resistance Genes in Cloning Systems for Industrial Corynebacterium Glutamicum Strains", J Biotechnol. Oct. 9, 2002;99(1):79-91.
Teitelbaum et al. "Mycobacterial infection of macrophages results in membrane-permeable phagosomes", Proc. Natl. Acad. Sci. U.S. A, Dec. 21, 1999, 96(26):15190-5.
Terracciano et al. "Cytogenetic alterations in liver cell tumors as detected by Comparitive Genomic Hybridization", Pathologica 95:71-82 (2003).
Thomas-Kaskel et al "Vaccination of Advanced Prostate Cancer Patients With PSCA and PSA Peptide-Loaded Dendritic Cells Induces DTH Responses That Correlate With Superior Overall Survival", Int J Cancer. 2006 Nov. 15, 2006;119(10):2428-34).
Thompson et al. "Costimulatory B7-H1 in Renal Cell Carcinoma Patients: Indicator of Tumor Aggressiveness and Potential Therapeutic Target" PNAS 101 (49); 17174-17179 (2004).
Thompson et al. "Overall Survival and PD-L1 Expression in Metastasized Malignant Melanoma" Cancer Res. 66:3381-3385 (2006).
Thompson et al. "Pathogenicity and immunogenicity of a Listeria monocytogenes strain that requires D-alanine for growth", Infect Immun. Aug. 1998;66(8):3552-61.
Thompson et al. "PD-1 Is Expressed by Tumor Infiltrating Cells and Is Associated With Poor Outcome for Patients With Renal Carcinoma" Clinical Cancer Research (2007) 15: 1757-1761.
Tilney et al., 1989, "Actin filaments and the growth, momvement, and speard of the intracellular bacterial parasite, Listeria monocytogenes" J. Cell Biol., Oct.; 109(4 Pt 1):1597-608.
Topalian et al., "Safety, Activity, and Immune Correlates of Anti-PD-1 Antibody in Cancer" New Eng. J Med. 366 (26): 2443-2454 (2012).
Triglia et al. "A procedure for in vitro amplification of DNA segments that lie outside the boundaries of known sequences", Nucleic Acids Res. Aug. 25, 1988;16(16):8186.
Uenaka et al. "T Cell Immunomonitoring and Tumor Responses in Patients Immunized With a Complex of Cholesterol-Bearing Hydrophobized Pullulan (CHP) and NY-ESO-1 Protein", Cancer Immun. Apr. 19, 2007;7(9)).

Ulmanen et al., "Transcription and translation of foreign genes in Bacillus Subtilis by the aid of a secretion vector" 1985, J. Bacteriol. 162:176-182.
Vasil et al., 1982, "Cloning of a phosphate-regulated hemolysin gene (phospholipase C) from Pseudomonas aeruginosa" J. Bacteriol. Oct.; 152(1):431-40.
Vaughan et al. Human Antibodies with Sub-nanomolar Affinities Isolated from a Large Non-immunized Phage Display Library, Nature Biotechnol. 14:309-314 (1996).
Vazquez et al. Differential regulation of Ia expression and antigen presentation by listeriolysin-producing versus non-producing strains of Listeria monocytogenes, J. Leukoc Biol. May 1996; 59(5):683-90.
Vazquez-Boland et al., 1992, "Nucleotide sequence of the lecithinase operon of Listeria monocytogenes and possible role of lecithinase in cell-to-cell spread" Infect. Immun. 60:219-230.
Verch et al. "Listeria Monocytogenes-Based Antibiotic Resistance Gene-Free Antigen Delivery System Applicable to Other Bacterial Vectors and DNA Vaccines", Infect Immun. Nov. 2004;72(11):6418-25.
Verma et al., 1995, "Delivery of class I and class II MHC-restricted T-cell epitopes of listeriolysin of listeria monocytogenes by attenuated *Salmonella*", Vacine, vol. 13, No. 2, p. 142-150.
Villanueva et al. "Listeriolysin is processed efficiently into an MHC class I-associated epitope in Listeria monocytogenes-infected cells", J. Immunol. Dec. 1, 1995;155(11):5227-33.
Vines et al. "Identfication and characterization of nucleotide sequence difference in three virulence-associate genes of listeria monocytogenes strains representing clinically important serotypes", Current Microbiology, May 1998, vol. 36, No. 5, pp. 309-318.
Von Heijne "A New Method for Predicting Signal Sequence Cleavage Sites" (1986) Nucleic Acids Res. 14:4683-4690.
Von Heijne. Patterns of Amino Acids near Signal-Sequence Cleavage Sites Eur. J. Biochem. 133:17-21 (1983).
Wada, Takuro "Development of Cancer Vaccine Therapy for Bone and Soft Tissue Sarcomas", J. Jpn. Orthop. Assoc. 78(8) 2004, p. S950.
Walker et al., 1994, "Tumor growth Alters T cell and macrophage production of and responsiveness to granulocyte-macrophage colony-stimulating factor: partial dysregulation through interleukin-10" Cell Immunol. 154(1):342-357.
Wallecha et al. "Construction and characterization of an attenuated Listeria monocytogenes strain for clinical use in cancer immunotherapy", Clin Vaccine Immunol. Jan. 2009;16(1):96-103.
Wallecha et al. "Multiple Effector Mechanisms Induced by Recombinant Listeria Monocytogenes Anticancer Immunotherapeutics", Advances in Applied Microbiology, vol. 66, 2009, pp. 1-27.
Ward et al., "Construction and characterisation of a series of multi-copy promoter-probe plasmid vectors for Streptomyces using the aminoglycoside phosphotransferase gene from Tn5 as indicator" 1986, Mol. Gen. Genet. 203:468-478.
Wasserman et al. "Catabolic alanine racemase from *Salmonella typhimurium*: DNA sequence, enzyme purification, and characterization", Biochemistry. Oct. 23, 1984;23(22):5182-7.
Watson et al., 1991, "Splenic macrophages from tumor-bearing mice co-expressing MAC-1 and MAC-2 antigen exert immunoregulatory functions via two distinct mechanisms" J. Leukoc Biol. 49(2):126-138.
Weber "Assessing Tumor Response to Therapy" Nucl. Med. 50:1S-10S (2009).
Wei et al., 2005, "Listeria monocytogenes phosphatidylinositol-specific phospholipase C has evolved for virulence by greatly reduced activity on GPI anchors" Proc. Natl. Acad. Sci. U.S.A. 102:12927-12931.
Weidt et al., 1994, "CD8+ T lymphocyte-mediated antiviral immunity in mice as a result of injection of recombinant viral proteins", J. Immunol. Sep. 15; 153(6):2554-61.
Weiskirch "Listeria monocytogenes: a potent vaccine vector for neoplastic and infectious disease" Immunol. Rev., vol. 158, Aug. 1997, p. 159-169.
Welch et al., Jul. 3, 1998, "Interaction of Human Arp2/3 Complex and the Listeria monocytogenes ActA Protein in Actin Filament Nucleation" Science 281:105-108; pa-998020.

(56) References Cited

OTHER PUBLICATIONS

Wilson et al. "Transient expression of bacterial gene fragments in eukaryotic cells: implications for CD8(+) T cell epitope analaysis", J. Immunol. Methods, Feb. 3, 2000; 234 (1-2):137-47.
Wipke et al. "Variable binding affinities of listeriolysin O peptides for the H-2Kd class I molecule", Eur J Immunol. Aug. 1993;23(8):2005-10.
Wirth et al., 1986, "Highly efficient protoplast transformation system for *Streptococcus faecalis* and a new *Escherichia coli*-S faecalis shuttle vector", J. Bacteriol. 165(3):831-6.
Wolff et. al. "Direct Gene Transfer into Mouse Muscle in Vivo", Science 247:1465(1990).
Wood et al. "Cancer immunotherapy using Listeria monocytogenes and listerial virulence factors" Immunol Res. ; 42(1-3):233-45. (2008).
Wootton et al. Statistics of Local Complexity in Amino Acid Sequences and Sequence Databases, Comput. Chem. 17:149-163 (1993).
Wright et al. "Lymphoid/Neuronal Cell Surface OX2 Glycoprotein Recognizes a Novel Receptor on Macrophages Implicated in the Control of Their Function", (2000) Immunity 13:233-242.
Wu et al., "Engineering an itracellular pathway for major histrocompatibility complex class II presentation of antigens", Proc. Natl. Acad. Sci. USA, 1995, 92:11671-5.
Yang et al. "A Randomized Trial of Bevacizumab, an Anti—Vascular Endothelial Growth Factor Antibody, for Metastatic Renal Cancer" (2003) New Engl. J. Med. 349:427-434.
Young et al., 1992, "Tumor-derived cytokines induce bone marrow suppressor cells that mediate immunosuppression through transforming growth factor beta", Cancer Immunol. Immunother. 35(1):14-18.
Young et al., 1995, "Holins: form and function in bacteriophage lysis" FEMS Microbiol Rev., Aug., 17 (1-2):191-205.
Zhang et al. "Powerblast: A New Network Blast Application for Interactive or Automated Sequence Analysis and Annotation" (1997) Genome Res. 7:649-656.
Zhang et al., 1993, "Functional replacement of the hemolysin A transport signal by a different primary sequence", Proc. Natl. Acad. Sci. U.S.A May 1; 90(9):4211-5.
Zhao et al. "Pathogenicity and immunogenicity of a vaccine strain of Listeria monocytogenes that relies on a suicide plasmid to supply an essential gene product", Infect Immun. Sep. 2005;73(9):5789-98.
Zwickey et al. "Antigen secreted from noncytosolic Listeria monocytogenes is processed by the classical MHC class I processing pathway", J. Immunol. Jun. 1, 1999;162(11):6341-50.
Zwickey et al. "Peptide epitopes from noncytosolic Listeria monocytogenes can be presented by major histocompatibility complex class I molecules", Infect. Immun. May 1996; 64(5):1870-2.
Yang et al. "A Randomized Trial of Bevacizumab, an Anti-Vascular Endothelial Growth Factor Antibody, for Metastatic Renal Cancer" (2003) New Engl. J. Med. 349:427-434.
Alpdogan et al., "Interleukin-15 enhances immune reconstitution after allogeneic bone marrow transplantation," Blood, 105(2):865-873, (2005).
Baumhoer et al., "Aberrant expression of the human epidermal growth factor receptor 2 oncogene is not a common feature in osteosarcoma," Human Pathology, 42(6):859-866, (2011).
Braun et al., "InIB: an invasion protein of Listeria monocytogenes with a novel type of surface association," Mol Microbiol. Jul. 1997; 25(2):285-294.
Broad, "The case of the unmentioned malignancy," Science, 210(4475):1229-1230, (1980).
Bruhn et al., "Listeria as a Vaccine Vector," Microbes and Infection, 9(10):1226-1235, (2007).
Caudy et al., "Fragile X-related protein and VIG associate with the RNA interference machinery" Genes and Development 16: 2491-2496, (2002).
Da'Dara et al., "Helminth infection suppresses T-cell immune response to HIV-DNA-based vaccine in mice," Vaccine 24(24): 5211-5219, (2006).

Glaser et al., "Comparative genomics of Listeria species," Science. Oct. 26, 2001;294(5543):849-852.
Kawashima, et al., "Identification of HLA-A3-restricted Cytotoxic T Lymphocyte Epitopes from Carcinoembryonic Antigen and HER-2/neu by Primary in Vitro Immunization with Peptide-pulsed Dendrite Cells," Cancer Research, 59:431-435, (1999).
Keegan, et al., "An IL-4 receptor region containing an insulin receptor motif is important for IL-4-mediated IRS-1 phosphorylation and cell growth," Cell, 76(5):811-820, (1994).
Kim et al., "High efficacy of a Listeria-based vaccine against metastatic breast cancer reveals a dual mode of action," Cancer Res. 69(14):5860-5866, (2009).
Kumar, et al., "Prognostic and predictive value of c-erbB2 overexpression in osteogenic sarcoma," Journal of Cancer Research and Therapeutics, 2(1):20, (2006).
Lauer et al., "Systematic mutational analysis of the amino-terminal domain of the Listeria monocytogenes ActA protein reveals novel functions in actin-based motility" Molecular Microbiology 42(5):1163-1177, 2001.
Li et al., "A meta-analysis on the association of HER-2 oveoreoxpression with prognosis in human osteosarcoma," European Journal of Cancer Care, 19(3):313-316, (2010).
Lucey et al., "Henrietta Lacks, HeLa cells, and cell culture contamination," Archives of Pathology & Laboratory Medicine, 133(9):1463-1467, (2009).
Mitchell et al., "Avoidance of Autophagy Mediated by PlcA or ActA Is Required for Listeria monocytogenes Growth in Macrophages," Infect Immun. May 2015;83(5):2175-2184.
Mustafa, et al., "Listeria Monocyiogenes Delivery of HPV-16 Major Capsid Protein L1 Induces Systemic and Mucosal Cell-Mediated CD4+ and CD8+ T-Cell Responses After Oral Immunization," Viral Immunology, 22(3):195-204, (2009).
Ogasawara Database EMBL, Oct. 13, 1997, "Bacillus subtilis Genome Sequence."
Ostrand-Rosenberg, "Myeloid-Derived Suppressor Cells: Linking Inflammation and Cancer," J Immunol. Apr. 15, 2009;182(8):4499-4506.
Roback, "Vaccine-enhanced donor lymphocy-te infusion (veDLI)," ASH Education Program Book, 2006(1):486-491, (2006).
Seggewiss et al., "Immune reconstitution after allogeneic transplantation and expanding options for immunomodulation: an update," Blood, 115(19):3861-3868, (2010).
Starks et al., "Listeria monocytogenes as a Vaccine Vector: Virulence Attenuation or Existing Antivector Immunity Does Not Diminish Therapeutic Efficacy," The Journal of Immunology, 173(1):420-427, (2004).
Thompson, et al., "Tumor B7-H1 is associated with poor prognosis in renal cell carcinoma patients with long-term follow-up," Cancer Research, 66(7):3381-3385, (2006). [Retrieved from Internet Nov. 28, 2017: <http://cancerres.aacrjournals.org/content/canres/66/7/3381.full.pdf>].
Yalçin et al., "C-erbB-2 expression and prognostic significance in osteosarcoma," Pediatric Blood & Cancer, 51(2):222-227, (2008).
Yomamoto et al., "Listeriolysin O derived from Listeria monocytogenes inhibits the effector phase of an experimental allergic rhinitis induced by ovalbumin in mice," Clin. Exp. Immunol., Jun. 2006;144(3):475-484.
Yeung et al., "Heat-killed Listeria monocytogenes as an Adjuvant Converts Established Murine Th2-Dominated Immune Response into Th1-Dominated Responses," The Journal of Immunology, 161(8):4146-4152, (1998).
Zakrzewski et al., "Adoptlve transfer of T-cell precursors enhances T-cell reconstitution after allogeneic hematopoietic stem cell transplantation," Nature Medicine,12(9):1039-1047, (2006).
EP Supplementary European Search Report for application 15758226.3 dated Aug. 7, 2014.
EP Supplementary European Search Report for application EP15755609.3 dated Aug. 1, 2017.
European Search Report Application No. 09751395.6 dated Jul. 11, 2012.
European Search Report Application No. 10830785.1 dated Dec. 10, 2013.

(56) References Cited

OTHER PUBLICATIONS

European Search Report Application No. 14190388.0 dated Mar. 2, 2015.
International Search report Application No. PCT/US 10/56534 dated Jun. 27, 2011.
International Search report Application No. PCT/US2012/051187 dated Jan. 23, 2013.
International Search Report for PCT Application No. PCT/US15/040911 dated Nov. 2, 2015.
International Search Report for PCT Application No. PCT/US15/40855 dated Dec. 18, 2015.
PCT International Preliminary Report on Patentability for application PCT/US2009/044538 dated Nov. 23, 2010.
PCT International Preliminary Report on Patentability for application PCT/US2010/056534 dated May 15, 2012.
PCT International Preliminary Report on Patentability for application PCT/US2012/028757 dated Sep. 17, 2013.
PCT International Preliminary Report on Patentability for application PCT/US2013/030521 dated Sep. 16, 2014.
PCT International Preliminary Report on Patentability for application PCT/US2015/017559 dated Aug. 30, 2016.
PCT International Preliminary Report on Patentability for application PCT/US2015/040911 dated Jan. 24, 2017.
PCT International Preliminary Report on Patentability for application PCT/US2016/016452 dated Aug. 8, 2017.
PCT International Preliminary Report on Patentability for application PCT/US2012/051187 dated Feb. 18, 2014.
PCT International Preliminary Report on Patentability for application PCT/US2015/018915 dated Sep. 6, 2016.
PCT International Preliminary Report on Patentability for application PCT/US2015/040855 dated Jan. 24, 2017.
PCT International Search Report and Written Opinion of the International Searching Authority for application PCT/US2015/040855 dated Dec. 18, 2015.
PCT International Search Report and Written Opinion of the International Searching Authority for application PCT/US2016/016452 dated Aug. 24, 2016.
PCT International Search Report for application PCT/US2013/030521 dated May 14, 2013.
PCT International Search Report for application PCT/US2015/018915 dated Jun. 19, 2015.
PCT Written Opinion of the International Searching Authority for application PCT/US2012/051187 dated Jan. 23, 2013.
PCT Written Opinion of the International Searching Authority for application PCT/US2009/044538 dated Aug. 14, 2009.
PCT Written Opinion of the International Searching Authority for application PCT/US2010/056534 dated Jun. 27, 2011.
PCT Written Opinion of the International Searching Authority for application PCT/US2012/028757 dated Aug. 27, 2012.
PCT Written Opinion of the International Searching Authority for application PCT/US2013/030521 dated May 14, 2013.
PCT Written Opinion of the International Searching Authority for application PCT/US2015/017559 dated Jun. 5, 2015.
PCT Written Opinion of the International Searching Authority for application PCT/US2015/040911 dated Nov. 2, 2015.
Supplementary European Search Report for European Application No. 11863004.5 dated Nov. 10, 2015
Supplementary European Search Report for European Application No. 12824212.0 dated Jun. 3, 2015
Supplementary European Search Report for European Application No. 13761946.6 dated Sep. 8, 2015.
WIPO Application No. PCT/US2009/044538, PCT International Search Report dated Aug. 14, 2009.
WIPO Application No. PCT/US2015/017559, PCT International Search Report dated Jun. 5, 2015.

atggcgcgggatggtatactatacaagcgtatggttcaaaaagatactttgaattaagaagt
acaataaagttaacttcattagacaaaaagaaaaaacaaggaagaatagtacatagttataa
atacttggagagtgaggtgtaatatgggggcagctgattttgggtttcatatatgtagtt
tcaagattagccattgttgcggcagtagtttacttcttatacttattgagaaaaattgcaaa
taaatagaaaaaagccttgtcaaacgaggcttttttatgcaaaaaatacgacgaatgaag
ccatgtgagacaatttggaatagcagacaacaaggaaggtagaacatgtttgaaaaattta
ctgattttcgattattattaacgcttgttaatttaaacatctcttattttgctaacatata
agtatacaaagggacataaaaaggttaacagcgtttgttaaataggaagtatatgaaaatcc
tcttttgtgttctaaatttatttttaaggagtggagaatgttgaaaaaaaataattggtta
caaaatgcagtaatagcaatgctagtgttaattgtaggtctgtgcattaatatgggttctgg
aacaaaagtacaagctgagagtattcaacgaccaacgcctattaaccaagttttccagatc
ccggcctagcgaatgcagtgaaacaaaatttagggaagcaaagtgttacagaccttgtatca
caaaaggaactatctggagtacaaaatttcaatggagataatagcaacattcaatctcttgc
gggaatgcaattttcactaatttaaaagaacttcatctatcccataatcaaataagtgacc
ttagtcctttaaaggatctaactaagttagaagagctatctgtgaatagaaacagactgaaa
aatttaaacggaattccaagtgcttgtttatctcgcttgttttagataacaacgaactcag
agatactgactcgcttattcatttgaaaaatctagaaatcttatctattcgtaataataagt
taaaaagtattgtgatgcttggttttttatcaaaactagaggtattagatttgcatggtaat
gaaataacaaatacaggtggactaactagattgaagaaagttaactggatagatttaactgg
tcagaaatgtgtgaatgaaccagtaaaataccaaccagaattgtatataacaaatactgtca
aagacccagatggaagatggatatctccatattacatcagtaatggtgggagttatgtagat
ggttgtgtcctgtgggaattgccagtttatacagatgaagtaagctataagtttagcgaata
tataaacgttggggagactgaggctatatttgatggaacagttacacaacctatcaagaatt
aggacttgtgcacacctgtatactttgagctctcgtataatcacgagagcttttaaatatg
taagtcttaattatctcttgacaaaaagaacgtttattcgtataaggttaccaagagatgaa
gaaactattttatttacaattcaccttgacaccaaaaactccatatgatatagtaaataagg
ttattaaacaagaaagaagaagcaacccgcttctcgcctcgttaacacgaacgttttcaggc
aaaaaattcaaactttcgtcgcgtagcttacgcgattttgaatgtgcgggattgctgaaaag
cagcccgttttttatggcctccgaacgaatgagttagcaggccgcagatttgaacagctat
tttctatcttgttgtaacaaaattaagtggaggtggctcaccattagcaaagacatgttggt
aaacgatgggattcgtgcacgtgaagtaagattgatcgaccaagacggtgaacaattaggcg
tgaagagtaaaatcgatgcgcttcaaattgctgaaaggctaatcttgatctagtgcttgtt
gctccaacagcgaaaccgccagtagctcgta (SEQ ID NO: 37)

FIG. 2

GAATTCatggcgcgggatggtatactatacaagcgtatggttcaaaaagatactttgaattaa
gaagtacaataaagttaacttcattagacaaaaagaaaaaacaaggaagaatagtacatagtt
ataaatacttggagagtgaggtgtaatatgggggcagctgattttggggtttcatatatgta
gtttcaagattagccattgttgcggcagtagtttacttctatacttattgagaaaaattgca
aataaatagaaaaaagccttgtcaaacgaggctttttatgcaaaaaatacgacgaatgaa
gccatgtgagacaatttggaatagcagacaacaaggaaggtagaacatgttttgaaaaattta
ctgattttcgattattattaacgcttgttaatttaaacatctcttatttttgctaacatataa
gtatacaaagggacataaaaaggttaacagcgtttgttaaataggaagtatatgaaaatcctc
ttttgtgtttctaaatttattttaaggagtggagaGGATCCggacttgtgcacacctgtata
ctttgagctctcgtataatcacgagagctttttaaatatgtaagtcttaattatctcttgaca
aaaagaacgtttattcgtataaggttaccaagagatgaagaaactattttatttacaattcac
cttgacaccaaaaactccatatgatatagtaaataaggttattaaacaagaagaagaagcaa
cccgcttctcgcctcgttaacacgaacgttttcaggcaaaaaattcaaactttcgtcgcgtag
cttacgcgattttgaatgtgcgggattgctgaaaagcagcccgttttttatggcctccgaac
gaatgagttagcaggccgcagatttgaacagctatttctatcttgttgtaacaaaattaagt
ggaggtggctcaccattagcaaagacatgttggtaaacgatgggattcgtgcacgtgaagtaa
gattgatcgaccaagacggtgaacaattaggcgtgaagagtaaaatcgatgcgcttcaaattg
ctgaaaaggctaatcttgatctagtgcttgttgctccaacagcgaaaccgccagtagctcgta
CTGCAG (SEQ ID NO: 38)

FIG. 3 gcgccaaatcattggttgattggtgaggatgtctgtgtgcgtgggtcgcgagatgggcgaataagaagcattaaagatcctgacaaatat
aatcaagcggctcatatgaaagattacgaatcgcttccactcacagaggaaggcgactggggcggagttcattataatagtggtatccc
gaataaagcagcctataatactatcactaaacttggaaaagaaaaaacagaacagctttattttcgcgccttaaagtactatttaacgaaaa
aatcccagtttaccgatgcgaaaaaagcgcttcaacaagcagcgaaagatttatatggtgaagatgcttctaaaaaagttgctgaagctt
gggaagcagttggggttaactgattaacaaatgttagagaaaaattaattctccaagtgatattcttaaaataattcatgaatatttttcttata
ttagctaattaagaagataactaactgctaatccaattttaacggaacaaattagtgaaaatgaaggccgaattttccttgttctaaaaaggt
tgtattagcgtatcacgaggagggagtataa*gtgggattaaacagatttatgcgtgcgatgatggtggttttcattactgccaattgcatt
acgattaaccccgacgtcgacccatacgacgttaattcttgcaatgttagctattggcgtgttctctttagggggcgtttatcaaaattatt
caattaagaaaaaataatta*aaaacacagaacgaaagaaaaagtgaggtgaatgatatgaaattcaaaaaggtggttctaggtatgtg
cttgatcgcaagtgttctagtcttccggtaacgataaaagcaaatgcctgttgtgatgaatacttacaaacacccgcagctccgcatgata
ttgacagcaaattaccacataaacttagttggtccgcggataacccgacaaatactgacgtaaatacgcactattggcttttaaacaagc
ggaaaaaatactagctaaagatgtaaatcatatgcgagctaatttaatgaatgaacttaaaaaattcgataaacaaatagctcaaggaata
tatgatgcggatcataaaaaatccatattatgatactagtacattttatctcattttataatcctgatagagataatacttatttgccgggttttgc
taatgcgaaaataacaggagcaaagtatttcaatcaatcggtgactgattaccgagaagggaa (SEQ ID NO: 41)

FIG. 5

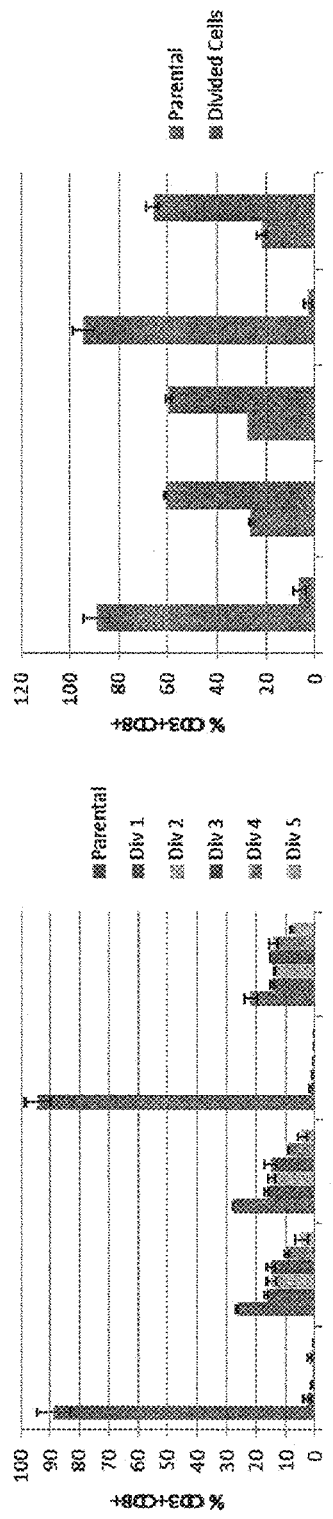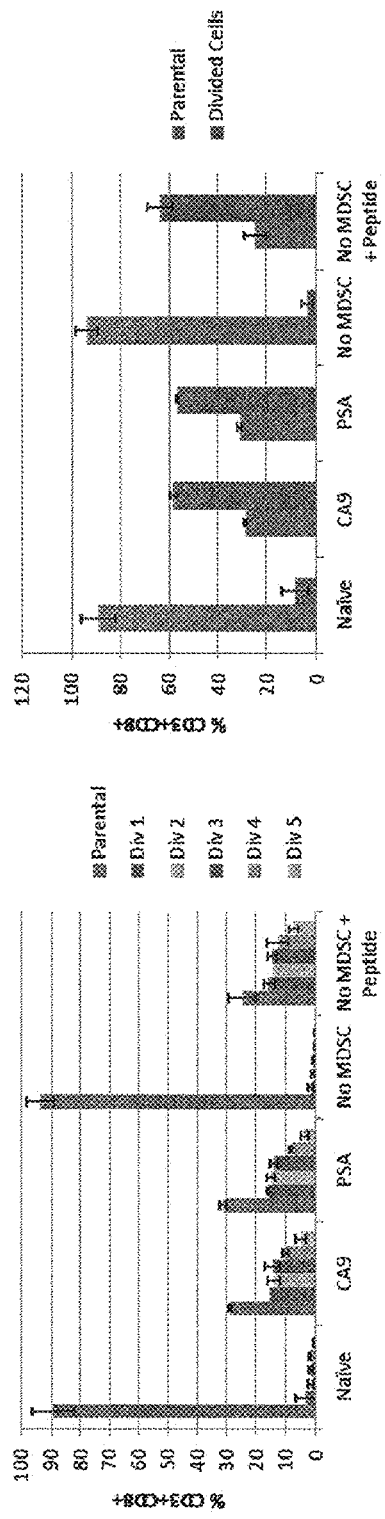
FIG. 8

US 10,064,898 B2

LISTERIA-BASED ADJUVANTS

CROSS-REFERENCE TO RELATED APPLICATIONS

This application is a divisional of U.S. application Ser. No. 14/004,455, filed Mar. 26, 2014, which is a National Phase Application of PCT International Application No. PCT/US 12/28757, International Filing Date Mar. 12, 2012, which claims priority to U.S. Provisional Patent application No. 61/451,651, filed Mar. 11, 2011. International Application No. PCT/US 12/28757 is also a continuation of U.S. application Ser. No. 13/210,696, filed Aug. 16, 2011 now U.S. Pat. No. 9,017,660, and is a continuation of U.S. application Ser. No. 13/290,783, filed Nov. 7, 2011, each of which is incorporated by reference herein in its entirety.

FIELD OF INVENTION

This invention provides methods and compositions for using *Listeria monocytogenes* as an adjuvant for enhancing immune responses in a subject.

BACKGROUND OF THE INVENTION

Adjuvants have extensive use in immunotherapy. The majority of cellular based immunotherapies administer adjuvants prior to giving antigen specific treatment. Typically these antigens include GM-CSF, IL-1, QP-100, Keyhole Limpet Cynanin, and others. These adjuvants are typically administered systemically via IV, IM, ID or similar routes.

*Listeria monocytogenes* (Lm) is an intracellular pathogen that primarily infects antigen presenting cells and has adapted for life in the cytoplasm of these cells. *Listeria monocytogenes* and a protein it produces named listeriolysin O (LLO) have strong adjuvant properties, that unlike the majority of adjuvants used for cellular based immunotherapies, can be administered after providing an antigen specific treatment.

A method of rapidly elevating a subject's immune response to any antigen is needed in order to decrease disease frequency in the subject and mortality resulting thereof. The present invention provides methods of elevating an immune response in subjects such as human adults and children by taking advantage of the adjuvant properties provided by live Lm vaccines that secrete non-hemolytic LLO or a truncated ActA.

Further, the same method is provided to reconstitute the immune response or facilitate the recovery of an immune response to normal or approximately normal levels in subjects that have undergone cytotoxic treatment as a result of cancer.

SUMMARY OF THE INVENTION

In one embodiment the invention relates to a method of reconstituting an immune response in a subject, the method comprising the step of administering a live attenuated *Listeria* vaccine strain to the subject.

In one embodiment the invention relates to a method of reconstituting an immune response in a subject, the method comprising the step of administering a live attenuated *Listeria* vaccine strain to the subject, the *Listeria* strain comprising a nucleic acid molecule, wherein the nucleic acid molecule comprises a first open reading frame encoding a PEST-containing polypeptide.

In one embodiment, the invention relates to a method of facilitating recovery of immune responses after cytotoxic treatments in a subject, the method comprising administering a live attenuated *Listeria* vaccine strain to the subject.

In one embodiment, the invention relates to a method of facilitating recovery of immune responses after cytotoxic treatments in a subject, the method comprising administering a live attenuated *Listeria* vaccine strain to the subject. In another embodiment the *Listeria* strain comprising a nucleic acid molecule, wherein the nucleic acid molecule comprises a first open reading frame encoding a PEST-containing polypeptide.

In one embodiment, the invention relates to a method of improving the immunogenicity of a vaccine, said method comprising the step of co-administering the vaccine and a *Listeria*-based adjuvant to a subject, wherein the *Listeria*-based adjuvant enhances the immunogenicity of said vaccine, thereby improving the immunogenicity of the vaccine.

In one embodiment, the invention relates to a method of enhancing an immune response against a disease in an antigen-independent manner in a subject, said method comprising administering a *Listeria*-based adjuvant to the subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

FIG. 2 shows the DNA sequences present upstream and downstream of the inlC region on the genome of *Listeria* strain EGD. DNA-up (red), inlC gene (blue) and DNA-down (black).

FIG. 3 shows the the sequence of DNA that is cloned in the temperature sensitive plasmid, pKSV7 to create inl C deletion mutant. The restriction enzyme sites used for cloning of these regions are indicated in caps and underlined. GAATTC-EcoRI, GGATCC-BamHI and CTGCAg-PstI. The EcoRI-PstI insert is cloned in the vector, pKSV7.

FIG. 5 shows the DNA sequence present upstream and downstream of the actA gene in the *Listeria* chromosome. The region in italics contains the residual actA sequence element that is present in the LmddΔactA strain. The underlined sequence gtcgac represent the restriction site of XhoI, which is the junction between the N-T and C-T region of actA.

FIG. 8 shows suppressor assay data demonstrating that monocytic MDSCs from TPSA23 tumors are less suppressive after *Listeria* vaccination. This change in the suppressive ability of the MDSCs is not antigen specific as the same decrease in suppression is seen with PSA-antigen specific T cells and also with non-specifically stimulated T cells. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.

DETAILED DESCRIPTION OF THE INVENTION

Figure 1A:
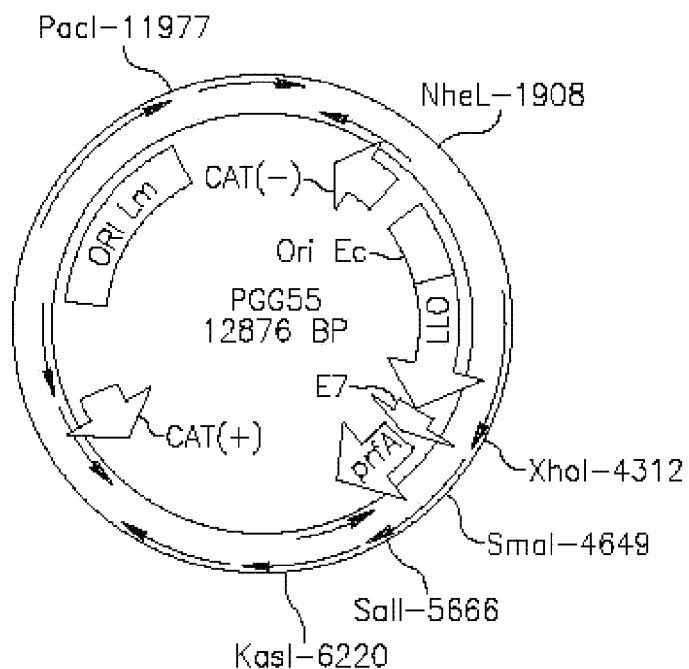
FIGS. 1A-B are schematic maps of *E. coli-Listeria* shuttle plasmids pGG55 (FIG. 1A) and pTV3 (FIG. 1B). CAT(−): *E. coli* chloramphenicol transferase; CAT(+): *Listeria* chloramphenicol transferase; Ori Lm: replication origin for *Listeria*; Ori Ec: p15 origin of replication for *E. coli*; prfA: *Listeria* pathogenicity regulating factor A; LLO: C-terminally truncated listeriolysin O, including its promoter; E7: HPV E7; p60-dal; expression cassette of p60 promoter and *Listeria* dal gene. Selected restriction sites are also depicted.

A novel and heretofore unexplored use is to create a live attenuated *Listeria* vaccine strain devoid of exogenous antigen.

A novel and heretofore unexplored use is to create a live attenuated *Listeria* vaccine strain devoid of antigen that enables the *Listeria* to secrete only the non-hemolytic form of LLO (Lm-LLO) or a truncated ActA (Lm-ActA) as an adjuvant. The invention provided herein addresses the first live adjuvant.

In one embodiment, provided herein is a method of reconstituting an immune response in a subject, the method comprising the step of administering a live attenuated *Listeria* vaccine strain to the subject. In another embodiment the *Listeria* strain comprises a nucleic acid molecule, wherein the nucleic acid molecule comprises a first open reading frame encoding a PEST-containing polypeptide.

In one embodiment, the *Listeria* over expresses said PEST-containing polypeptide. In another embodiment, the PEST-containing polypeptide is a non-hemolytic LLO protein or immunogenic fragment thereof, an ActA protein or truncated fragment thereof, or a PEST amino acid sequence.

In one embodiment, provided herein is a method of facilitating recovery of immune responses after cytotoxic treatments in a subject, the method comprising administering a live attenuated *Listeria* vaccine strain to the subject. In another embodiment, the *Listeria* strain comprises a nucleic acid molecule, wherein the nucleic acid molecule comprises a first open reading frame encoding a PEST-containing polypeptide.

In one embodiment, provided herein is a method of improving the immunogenicity of a vaccine, the method comprising the step of co-administering the vaccine and a *Listeria*-based adjuvant to a subject, wherein the *Listeria*-based adjuvant enhances the immunogenicity of the vaccine, thereby improving the immunogenicity of the vaccine.

In one embodiment, provided herein is a method of enhancing an immune response against a disease in an antigen-independent manner in a subject, the method comprising administering a *Listeria*-based adjuvant to the subject.

In one embodiment, provided herein is a composition and method for bioengineering a live Lm bacterium that infects specific cells, including; antigen processing cells (APC), Kupffer cells, vascular endothelium, bone marrow, and others; as well as structures such as solid tumors and spleen. In another embodiment, the live Lm adjuvant then synthesizes and secretes a modified LLO fragment in situ where the adjuvant is needed and used to stimulate immune responses. In another embodiment the live Lm synthesizes ActA. In another embodiment, unlike previous adjuvants, the instant invention administers the ability to make an adjuvant in situ and does not involve the systemic administration of an immune adjuvant.

In one embodiment, provided herein is a method of eliciting an adult-level enhanced immune response in neonate subjects, the method comprising the step of administering a recombinant *Listeria* vaccine strain to the subject. In another embodiment, the *Listeria* strain comprising a nucleic acid molecule, wherein the nucleic acid molecule comprises a first open reading frame encoding a non-hemolytic listeriolysin O (LLO) or ActA, wherein the nucleic acid molecule further comprises a second open reading frame encoding a metabolic enzyme, wherein the metabolic enzyme complements an endogenous gene that is lacking in the chromosome of the recombinant *Listeria* strain.

In one embodiment, provided herein a method of facilitating recovery of immune responses after cytotoxic treatments in a subject, the method comprising administering a recombinant *Listeria* vaccine strain to the subject. In another embodiment, the *Listeria* strain comprising a nucleic acid molecule, wherein the nucleic acid molecule comprises a first open reading frame encoding a non-hemolytic listeriolysin O or ActA, wherein the nucleic acid molecule further comprises a second open reading frame encoding a metabolic enzyme, wherein the metabolic enzyme complements an endogenous gene that is lacking in the chromosome of said recombinant *Listeria* strain. In another embodiment, the subject is an adult human subject.

The ability of an adjuvant to increase the immune response to an antigen is typically manifested by a significant increase in immune-mediated protection. For example, an increase in humoral immunity is typically manifested by a significant increase in the titer of antibodies raised to the antigen, and an increase in T-cell activity is typically manifested in increased cell proliferation, increased cytokine production and/or antigen specific cytolytic activity. An adjuvant may also alter an immune response, for example, by enabling a Th1 response against a background of a persistent Th2 phenotype.

In one embodiment, this invention provides methods and compositions for preventing disease, treating disease and vaccinating a human subject.

In another embodiment, the present invention is directed to enhancing immune response of a human, a neonate, or a human that has been subjected to cytotoxic treatment as a result of cancer.

In one embodiment, a *Listeria*-based adjuvant refers to a live-attenuated *Listeria* vaccine strain. *In another embodiment, the Listeria*-based adjuvant is an Lm-LLO or an Lm-ActA. In another embodiment, Lm-LLO expresses a non-hemolytic LLO. In another embodiment, Lm-ActA expresses a truncated ActA protein. In another embodiment, Lm-LLO or Lm-ActA can be used alone, or in combination with any therapy in which an adjuvant is appropriate, and may have utility in settings where no adjuvant has been commonly used, such as chemotherapy or radiotherapy.

In another embodiment, the *Listeria* strain provided herein further comprises a third open reading frame encoding a metabolic enzyme.

In one embodiment, the metabolic enzyme is an amino acid metabolism enzyme. In another embodiment, the metabolic enzyme encoded by the second open reading frame is an alanine racemase enzyme or a D-amino acid transferase enzyme. In another embodiment, the metabolic enzyme encoded by the third open reading frame is an alanine racemase enzyme or a D-amino acid transferase enzyme. In another embodiment, the metabolic enzyme is encoded dal gene, where in another embodiment the dal gene is from *B. subtilis*. In another embodiment, the metabolic enzyme is encoded by the dat gene.

In another embodiment, the recombinant *Listeria* is an attenuated auxotrophic strain.

In one embodiment the attenuated strain is Lmdd. In another embodiment the attenuated strain is Lmdda. In another embodiment, the attenuated strain is LmΔPrfA. In another embodiment, the attenuated strain is LmΔPlcB. In another embodiment, the attenuated strain is LmΔPlcA. In another embodiment, the attenuated strain is LmddAΔinlC. In another embodiment, the LmddAΔinlC mutant strain is created using EGD strain of Lm, which is different from the background strain 10403S, the parent strain for Lm dal dat actA (LmddA). In another embodiment, this strain exerts a strong adjuvant effect which is an inherent property of *Listeria*-based vaccines. In another embodiment, this strain is constructed from the EGD *Listeria* backbone.

In another embodiment, the strain used in the invention is a *Listeria* strain that expresses a non-hemolytic LLO. In yet another embodiment the *Listeria* strain is a prfA mutant, ActA mutant, a plcB deletion mutant, or a double mutant lacking both plcA and plcB. All these *Listeria* strain are contemplated for use in the methods provided herein. Each possibility represents a separate embodiment of the present invention.

In one embodiment, the LmddAΔinlC mutant strain is safe for use in humans and induces high levels of innate immune responses. In one embodiment, the inlC deletion mutant generates an enhanced level of innate immune responses that are not antigen specific.

In one embodiment, translocation of *Listeria* to adjacent cells is inhibited by two separate mechanisms, deletion of actA and inlC genes, both of which are involved in the process, thereby resulting in unexpectedly high levels of attenuation with increased immunogenicity and utility as a vaccine backbone. In another embodiment, translocation of *Listeria* to adjacent cells is inhibited by two separate mechanisms, deletion of actA or inlC genes, both of which are involved in the process, thereby resulting in unexpectedly high levels of attenuation with increased immunogenicity and utility as a vaccine backbone.

Internalins are associated with increased virulence and their presence is associated with increased immunogenicity of *Listeria*, however, in the present invention, excising the inlC gene increases immunogenicity of the *Listeria* vaccine vector provided herein. In another embodiment, the present invention provides the novelty that the inlC genes are excised from a vector in which actA is deleted, thereby removing both, the ability to form actin flagella necessary for movement through the host cell membrane and into the neighboring cell, and the ability for transmembrane passage. Therefore, the combination of these two deletions yields the surprising result of decreased virulence and increased immunogenicity of a *Listeria* vaccine vector over a wild-type *Listeria* strain or a single mutant strain.

In another embodiment, the nucleic acid molecule provided herein is integrated into the *Listeria* genome. In another embodiment, the nucleic acid molecule is in a plasmid in the recombinant *Listeria* vaccine strain also provided herein. In another embodiment, the plasmid provided herein is stably maintained in the recombinant *Listeria* vaccine strain in the absence of antibiotic selection. In another embodiment, the plasmid does not confer antibiotic resistance upon said recombinant *Listeria*.

In one embodiment, the recombinant *Listeria* strain provided herein is attenuated. In another embodiment, the recombinant *Listeria* lacks the ActA virulence gene. In another embodiment, the recombinant *Listeria* lacks the PrfA virulence gene.

In another embodiment, the recombinant *Listeria* vaccine strain comprises an adjuvant, wherein the adjuvant is listeriolysin O. In another embodiment, the recombinant *Listeria* vaccine strain comprises an adjuvant, wherein the adjuvant is ActA.

In one embodiment, the *Listeria* vaccine strain is LmddAinlC142 strain. LmddAinlC142 is based on a *Listeria* vaccine vector which is attenuated due to the deletion of inlC gene and retains the plasmid for PSA expression in vivo and in vitro by complementation of dal gene. In another embodiment, LmddAinlC142 exerts strong and antigen specific anti-tumor responses with ability to break tolerance toward a heterologous antigen in a subject. In another embodiment, the LmddAinlC142 strain is highly attenuated and has a better safety profile than previous *Listeria* vaccine generation, as it is more rapidly cleared from the spleens of the immunized mice. In another embodiment, LmddAinlC142 strain is highly immunogenic, able to break tolerance toward a heterologous antigen and prevents tumor formation in a subject.

In another embodiment, the methods provided herein further provide methods of overcoming or "breaking" tolerance toward a heterologous antigen that is a self-antigen. Such antigens may be aberrantly expressed by various tumors which are subject to treatment or prophylaxis under the scope of the present invention by using the methods and compositions provided herein.

In one embodiment, recombinant attenuated, antibiotic-free Listerias expressing listeriolysin O in combination with other therapeutic modalities are useful for enhancing an immune response, and for preventing, and treating a cancer or solid tumors. In another embodiment, recombinant attenuated, antibiotic-free Listerias expressing listeriolysin O alone, or in combination with other therapeutics are useful for preventing, and treating infectious diseases in a subject. In another embodiment, the subject is a neonate, a child, or an adult.

In one embodiment, recombinant attenuated, antibiotic-free Listerias expressing ActA in combination with other therapeutic modalities are useful for enhancing an immune response, and for preventing, and treating a cancer or solid tumors. In another embodiment, recombinant attenuated, antibiotic-free Listerias expressing ActA alone, or in combination with other therapeutics are useful for preventing, and treating infectious diseases in a subject. In another embodiment, the subject is a neonate, a child, or an adult.

In one embodiment, the immune response induced by the methods and compositions provided herein is a therapeutic one. In another embodiment it is a prophylactic immune response. In another embodiment, it is an enhanced immune response over methods available in the art for inducing an immune response in a subject afflicted with the conditions provided herein. In another embodiment, the immune response leads to clearance of the disease provided herein that is afflicting the subject.

It is to be understood that the methods of the present invention may be used to treat any infectious disease, which in one embodiment, is bacterial, viral, microbial, microorganism, pathogenic, or combination thereof, infection. In another embodiment, the methods of the present invention are for inhibiting or suppressing a bacterial, viral, microbial, microorganism, pathogenic, or combination thereof, infection in a subject. In another embodiment, the present invention provides a method of eliciting a cytotoxic T-cell response against a bacterial, viral, microbial, microorganism, pathogenic, or combination thereof, infection in a subject. In another embodiment, the present invention provides a method of inducing a Th1 immune response against a bacterial, viral, microbial, microorganism, pathogenic, or combination thereof, infection in a Th1 unresponsive subject. In one embodiment, the infection is viral, which in one embodiment, is HIV. In one embodiment, the infection is bacterial, which in one embodiment, is mycobacteria, which in one embodiment, is tuberculosis. In one embodiment, the infection is eukaryotic, which in one embodiment, is plasmodium, which in one embodiment, is malaria.

In one embodiment, provided herein is a method of inducing a Th1 immune response in a Th1 unresponsive subject having a concomitant helminth infection, where in another embodiment, the method comprises using a *Listeria* vaccine vector.

In another embodiment, provided herein is a method of improving the immunogenicity of a vaccine, the method comprising co-administering the vaccine and a *Listeria*-based adjuvant to a subject, wherein the *Listeria*-based adjuvant enhances the immunogenicity of the vaccine, thereby improving the immunogenicity of the vaccine. In one embodiment, the method enables the treatment of a disease for which said vaccine is specific against.

In one embodiment, provided herein is a method of enhancing an immune response against a disease in an antigen-independent manner, the method comprising administering a *Listeria*-based adjuvant to a subject.

In another embodiment, the *Listeria*-based adjuvant is an LLO-expressing *Listeria* strain or an LLO protein or a non-hemolytic fragment thereof. In another embodiment, the *Listeria*-based adjuvant is an ActA-expressing *Listeria* strain or an ActA protein or a truncated fragment thereof. In another embodiment, *Listeria*-based adjuvant is used alone or is combined with an additional adjuvant. In another embodiment, the additional adjuvant is a non-nucleic acid adjuvant including aluminum adjuvant, Freund's adjuvant, MPL, emulsion, GM-CSF, QS21, SBAS2, CpG-containing oligonucleotide, a nucleotide molecule encoding an immune-stimulating cytokine, the adjuvant is or comprises a bacterial mitogen, or a bacterial toxin. In another embodiment, the LLO protein or hemolytic fragment thereof is admixed with or chemically coupled to said vaccine.

In one embodiment, the vaccine is selected from the group consisting of hepatitis B virus blood-derived vaccine, hepatitis B virus genetic engineering protein vaccines, HBV virus vector vaccine, hepatitis B virus bacterium vector vaccine, hepatitis B virus transgenic plant vaccine, rabies virus blood-derived vaccine, rabies virus genetic engineering protein vaccines, rabies virus vector vaccine, rabies virus bacterium vector vaccine, and rabies virus transgenic plant vaccine, and the DNA vaccine is selected from the group consisting of hepatitis B virus DNA vaccine and rabies DNA vaccine.

In another embodiment, the *Listeria*-based adjuvant is used alone or is combined with an additional adjuvant.

In another embodiment, the adjuvant of the present invention is co-administered with an additional adjuvant. In another embodiment, the additional adjuvant utilized in methods and compositions of the present invention is, in another embodiment, a granulocyte/macrophage colony-stimulating factor (GM-CSF) protein. In another embodiment, the adjuvant comprises a GM-CSF protein. In another embodiment, the adjuvant is a nucleotide molecule encoding GM-CSF. In another embodiment, the adjuvant comprises a nucleotide molecule encoding GM-CSF. In another embodiment, the adjuvant is saponin QS21. In another embodiment, the adjuvant comprises saponin QS21. In another embodiment, the adjuvant is monophosphoryl lipid A. In another embodiment, the adjuvant comprises monophosphoryl lipid A. In another embodiment, the adjuvant is SBAS2. In another embodiment, the adjuvant comprises SBAS2. In another embodiment, the adjuvant is an unmethylated CpG-containing oligonucleotide. In another embodiment, the adjuvant comprises an unmethylated CpG-containing oligonucleotide. In another embodiment, the adjuvant is an immune-stimulating cytokine. In another embodiment, the adjuvant comprises an immune-stimulating cytokine. In another embodiment, the adjuvant is a nucleotide molecule encoding an immune-stimulating cytokine. In another embodiment, the adjuvant comprises a nucleotide molecule encoding an immune-stimulating cytokine. In another embodiment, the adjuvant is or comprises a quill glycoside. In another embodiment, the adjuvant is or comprises a bacterial mitogen. In another embodiment, the adjuvant is or comprises a bacterial toxin. In another embodiment, the adjuvant is or comprises any other adjuvant known in the art. Each possibility represents a separate embodiment of the present invention.

In one embodiment, provided herein is a nucleic acid molecule that encodes the adjuvant of the present invention. In another embodiment, the nucleic acid molecule is used to transform the *Listeria* in order to arrive at a recombinant *Listeria*. In another embodiment, the nucleic acid provided herein used to transform *Listeria* lacks a virulence gene. In another embodiment, the nucleic acid molecule integrated into the *Listeria* genome carries a non-functional virulence gene. In another embodiment, the virulence gene is mutated in the recombinant *Listeria*. In yet another embodiment, the nucleic acid molecule is used to inactivate the endogenous gene present in the *Listeria* genome. In yet another embodiment, the virulence gene is an ActA gene, an inlC gene or a PrfA gene. As will be understood by a skilled artisan, the virulence gene can be any gene known in the art to be associated with virulence in the recombinant *Listeria*.

In one embodiment, the metabolic gene, the virulence gene, etc. is lacking in a chromosome of the *Listeria* strain. In another embodiment, the metabolic gene, virulence gene, etc. is lacking in the chromosome and in any episomal genetic element of the *Listeria* strain. In another embodiment, the metabolic gene, virulence gene, etc. is lacking in the genome of the virulence strain. In one embodiment, the virulence gene is mutated in the chromosome. In another embodiment, the virulence gene is deleted from the chromosome. Each possibility represents a separate embodiment of the present invention.

In another embodiment, the nucleic acids and plasmids provided herein do not confer antibiotic resistance upon the recombinant *Listeria*.

"Nucleic acid molecule" refers, in another embodiment, to a plasmid. In another embodiment, the term refers to an integration vector. In another embodiment, the term refers to a plasmid comprising an integration vector. In another embodiment, the integration vector is a site-specific integration vector. In another embodiment, a nucleic acid molecule of methods and compositions of the present invention are composed of any type of nucleotide known in the art. Each possibility represents a separate embodiment of the present invention.

"Metabolic enzyme" refers, in another embodiment, to an enzyme involved in synthesis of a nutrient required by the host bacteria. In another embodiment, the term refers to an enzyme required for synthesis of a nutrient required by the host bacteria. In another embodiment, the term refers to an enzyme involved in synthesis of a nutrient utilized by the host bacteria. In another embodiment, the term refers to an enzyme involved in synthesis of a nutrient required for sustained growth of the host bacteria. In another embodiment, the enzyme is required for synthesis of the nutrient. Each possibility represents a separate embodiment of the present invention.

"Stably maintained" refers, in another embodiment, to maintenance of a nucleic acid molecule or plasmid in the absence of selection (e.g. antibiotic selection) for 10 generations, without detectable loss. In another embodiment, the period is 15 generations. In another embodiment, the period is 20 generations. In another embodiment, the period is 25 generations. In another embodiment, the period is 30 generations. In another embodiment, the period is 40 generations. In another embodiment, the period is 50 generations. In another embodiment, the period is 60 generations. In another embodiment, the period is 80 generations. In another embodiment, the period is 100 generations. In another embodiment, the period is 150 generations. In another embodiment, the period is 200 generations. In another embodiment, the period is 300 generations. In another embodiment, the period is 500 generations. In another embodiment, the period is more than generations. In another embodiment, the nucleic acid molecule or plasmid is maintained stably in vitro (e.g. in culture). In another embodiment, the nucleic acid molecule or plasmid is maintained stably in vivo. In another embodiment, the nucleic acid molecule or plasmid is maintained stably both in vitro and in vitro. Each possibility represents a separate embodiment of the present invention.

In another embodiment, the metabolic enzyme of the methods and compositions provided herein is an amino acid metabolism enzyme, where, in another embodiment, the metabolic enzyme is an alanine racemase enzyme. In another embodiment, the metabolic enzyme is a D-amino acid transferase enzyme. In another embodiment, the metabolic enzyme catalyzes a formation of an amino acid used for a cell wall synthesis in the recombinant *Listeria* strain, where in another embodiment the metabolic enzyme is an alanine racemase enzyme.

In another embodiment, the gene encoding the metabolic enzyme is expressed under the control of the *Listeria* p60 promoter. In another embodiment, the in1A (encodes internalin) promoter is used. In another embodiment, the hly promoter is used. In another embodiment, the ActA promoter is used. In another embodiment, the integrase gene is expressed under the control of any other gram positive promoter. In another embodiment, the gene encoding the metabolic enzyme is expressed under the control of any other promoter that functions in *Listeria*. The skilled artisan will appreciate that other promoters or polycistronic expression cassettes may be used to drive the expression of the gene. Each possibility represents a separate embodiment of the present invention.

The LLO utilized in the methods and compositions provided herein is, in one embodiment, a *Listeria* LLO. In one embodiment, the *Listeria* from which the LLO is derived is *Listeria monocytogenes* (Lm). In another embodiment, the *Listeria* is *Listeria ivanovii*. In another embodiment, the *Listeria* is *Listeria welshimeri*. In another embodiment, the *Listeria* is *Listeria seeligeri*.

In one embodiment, the LLO protein is encoded by the following nucleic acid sequence set forth in (SEQ ID NO: 1).

(SEQ ID NO: 1)
atgaaaaaaataatgctagttttattacacttatatattagttagtcta ccaattgcgcaacaaactgaagcaaaggatgcatctgcattcaataaa gaaaattcaatttcatccatggcaccaccagcatctccgcctgcaagt cctaagacgccaatcgaaaagaaacacgcggatgaaatcgataagtat atacaaggattggattacaataaaaacaatgtattagtataccacgga gatgcagtgacaaatgtgccgccaagaaaaggttacaaagatggaaat gaatatattgttgtggagaaaaagaagaaatccatcaatcaaaataat gcagacattcaagttgtgaatgcaatttcgagcctaacctatccaggt gctctcgtaaaagcgaattcggaattagtagaaaatcaaccagatgtt ctccctgtaaaacgtgattcattaacactcagcattgatttgccaggt atgactaatcaagacaataaaatagttgtaaaaaatgccactaaatca aacgttaacaacgcagtaaatacattagtggaaagatggaatgaaaaa tatgctcaagcttatccaaatgtaagtgcaaaaattgattatgatgac gaaatggcttacagtgaatcacaattaattgcgaaatttggtacagca tttaaagctgtaaataatagcttgaatgtaaacttcggcgcaatcagt gaagggaaaatgcaagaagaagtcattagttttaaacaaatttactat aacgtgaatgttaatgaacctacaagaccttccagattttcggcaaa gctgttactaaagagcagttgcaagcgcttggagtgaatgcagaaaat cctcctgcatatatctcaagtgtggcgtatggccgtcaagtttatttg aaattatcaactaattcccatagtactaaagtaaaagctgcttttgat gctgccgtaagcggaaaatctgtctcaggtgatgtagaactaacaaat atcatcaaaaattcttccttcaaagccgtaatttacggaggttccgca aaagatgaagttcaaatcatcgacggcaacctcggagacttacgcgat attttgaaaaaggcgctacttttaatcgagaaacaccaggagttccc attgcttatacaacaaacttcctaaaagacaatgaattagctgttatt aaaaacaactcagaatatattgaaacaacttcaaaagcttatacagat ggaaaaattaacatcgatcactctggaggatacgttgctcaattcaac atttcttgggatgaagtaaattatgatctcgag.

In another embodiment, the LLO protein has the sequence SEQ ID NO: 2

(SEQ ID NO: 2)
M K K I M L V F I T L I L V S L P I A Q Q T E A

K D A S A F N K E N S I S S M A P P A S P P A S

P K T P I E K K H A D E I D K Y I Q G L D Y N K

N N V L V Y H G D A V T N V P P R K G Y K D G N

E Y I V V E K K K K S I N Q N N A D I Q V V N A

I S S L T Y P G A L V K A N S E L V E N Q P D V

L P V K R D S L T L S I D L P G M T N Q D N K I

V V K N A T K S N V N N A V N T L V E R W N E K

Y A Q A Y P N V S A K I D Y D D E M A Y S E S Q

L I A K F G T A F K A V N N S L N V N F G A I S

E G K M Q E E V I S F K Q I Y Y N V N V N E P T

R P S R F F G K A V T K E Q L Q A L G V N A E N

P P A Y I S S V A Y G R Q V Y L K L S T N S H S

-continued

TKVKAAFDAAVSGKSVSGDVELTN

IIKNSSFKAVIYGGSAKDEVQIID

GNLGDLRDILKKGATFNRETPGVP

IAYTTNFLKDNELAVIKNNSEYIE

TTSKAYTDGKINIDHSGGYVAQFN

ISWDEVNYDL

The first 25 amino acids of the proprotein corresponding to this sequence are the signal sequence and are cleaved from LLO when it is secreted by the bacterium. Thus, in this embodiment, the full length active LLO protein is 504 residues long. In another embodiment, the LLO protein has a sequence set forth in GenBank Accession No. DQ054588, DQ054589, AY878649, U25452, or U25452. In another embodiment, the LLO protein is a variant of an LLO protein. In another embodiment, the LLO protein is a homologue of an LLO protein. Each possibility represents a separate embodiment of the present invention.

In another embodiment, "truncated LLO" or "tLLO" refers to a fragment of LLO that comprises the PEST-like domain. In another embodiment, the terms refer to an LLO fragment that does not contain the activation domain at the amino terminus and does not include cystine 484. In another embodiment, the LLO fragment consists of a PEST sequence. In another embodiment, the LLO fragment comprises a PEST sequence. In another embodiment, the LLO fragment consists of about the first 400 to 441 amino acids of the 529 amino acid full-length LLO protein. In another embodiment, the LLO fragment is a non-hemolytic form of the LLO protein.

In one embodiment, the LLO fragment consists of about residues 1-25. In another embodiment, the LLO fragment consists of about residues 1-50. In another embodiment, the LLO fragment consists of about residues 1-75. In another embodiment, the LLO fragment consists of about residues 1-100. In another embodiment, the LLO fragment consists of about residues 1-125. In another embodiment, the LLO fragment consists of about residues 1-150. In another embodiment, the LLO fragment consists of about residues 1175. In another embodiment, the LLO fragment consists of about residues 1-200. In another embodiment, the LLO fragment consists of about residues 1-225. In another embodiment, the LLO fragment consists of about residues 1-250. In another embodiment, the LLO fragment consists of about residues 1-275. In another embodiment, the LLO fragment consists of about residues 1-300. In another embodiment, the LLO fragment consists of about residues 1-325. In another embodiment, the LLO fragment consists of about residues 1-350. In another embodiment, the LLO fragment consists of about residues 1-375. In another embodiment, the LLO fragment consists of about residues 1-400. In another embodiment, the LLO fragment consists of about residues 1-425. Each possibility represents a separate embodiment of the present invention.

In another embodiment, provided herein, is a vaccine comprising a recombinant form of *Listeria* of the present invention.

In another embodiment, provided herein, is a culture of a recombinant form of *Listeria* of the present invention.

In one embodiment, the live attenuated *Listeria* or recombinant *Listeria* provided herein expresses an ActA protein or a fragment thereof. In another embodiment of the methods and compositions of the present invention, a fragment of an ActA protein is fused to the heterologous antigen or a fragment thereof also provided herein. In another embodiment, the fragment of an ActA protein has the sequence:
MRAMMVVFITANCITINPDIIFAATDSEDSSLNT-DEWEEEKTEEQPSEVNTGP RYETAREVS SRDIKELEKSNKVRNTNKADLIAMLKEKAEKGPN-INNNNSEQTENAAI NEEASGADRPAIQVERRH-PGLPSDSAAEIKKRRKAIASSDSELESLTYPDKPTK-VNKK
KVAKESVADASESDLDSSMQSADESSPQPLKAN-QQPFFPKVFKKIKDAGKWVRDKID ENPEVK-KAIVDKSAGLIDQLLTKKKSEEVNASDFPPPPTDEEL-RLALPETPMLLGFNA
PATSEPSSFEFPPPPTDEELRLALPETPMLLGFNAPAT-SEPSSFEFPPPPTEDELEIIRETA SSLDSSFTRGDLASL-RNAINRHSQNFSDFPPIPTEEELNGRGGRP (SEQ ID No: 3). In another embodiment, an ActA AA sequence of methods and compositions of the present invention comprises the sequence set forth in SEQ ID No: 3. In another embodiment, the ActA AA sequence is a homologue of SEQ ID No: 3. In another embodiment, the ActA AA sequence is a variant of SEQ ID No: 3. In another embodiment, the ActA AA sequence is a fragment of SEQ ID No: 3. In another embodiment, the ActA AA sequence is an isoform of SEQ ID No: 3. Each possibility represents a separate embodiment of the present invention.

In another embodiment, the ActA fragment is encoded by a recombinant nucleotide comprising the sequence:
ATGCGTGCGATGATGGTGGTTTTCATTACTGC-CAATTGCATTACGATTAACCCCGA CATAATATTT-GCAGCGACAGATAGCGAAGAT-TCTAGTCTAAACACAGATGAATGG
GAAGAAGAAAAAACAGAAGAGCAACCAAGCGAG-GTAAATACGGGACCAAGATA CGAAACTGCACGT-GAAGTAAGTTCACGTGATATTAAAGAACTA-GAAAAATCGAA
TAAAGTGAGAAATACGAACAAAGCAGAC-CTAATAGCAATGTTGAAAGAAAAAGC
AGAAAAAGGTCCAAATATCAATAATAACAACAGT-GAACAAACTGAGAATGCGGC TATAAATGAAGAG-GCTTCAGGAGCCGACCGACCAGCTATACAAGTG-GAGCGTCG
TCATCCAGGATTGCCATCGGATAGCGCAGCG-GAAATTAAAAAAAGAAGGAAAGC CATAGCAT-CATCGGATAGTGAGCTTGAAAGCCTTACTTATCCG-GATAAACCAACA
AAAGTAAATAAGAAAAAAGTGGCGAAAGAGTCA-GTTGCGGATGCTTCTGAAAGT GACTTAGATTCTAG-CATGCAGTCAGCAGATGAGTCTTCACCACAACCTT-TAAAAG
CAAACCAACAACCATTTTTCCCTAAAGTATT-TAAAAAAATAAAAGATGCGGGGA AATGGGTACGT-GATAAAATCGACGAAAATCCTGAAG-TAAAGAAAGCGATTGTTG
ATAAAAGTGCAGGGTTAATTGACCAATTATTAAC-CAAAAAGAAAAGTGAAGAGG TAAATGCTTCG-GACTTCCCGCCACCACCTACGGATGAAGAGT-TAAGACTTGCTTT
GCCAGAGACACCAATGCTTCTTGGTTTTAATGCTC-CTGCTACATCAGAACCGAGC TCATTCGAATTTC-CACCACCACCTACGGATGAAGAGTTAAGACTT-GCTTTGCCAG
AGACGCCAATGCTTCTTGGTTTTAATGCTCCTGC-TACATCGGAACCGAGCTCGTTC GAATTTCCACCGC-CTCCAACAGAAGATGAACTAGAAATCATC-CGGGAAACAGCA TCCTCGCTAGATTCTAGTTTTACAAGAGGGGATT-TAGCTAGTTTGAGAAATGCTAT TAATCGCCATAGT-CAAAATTTCTCTGATTTCCCACCAATCCCAACA-GAAGAAGAG TTGAA CGGGAGAGGCGGTAGACCA (SEQ ID NO: 4). In another embodiment, the recombinant nucleotide has the sequence set forth in SEQ ID NO: 4. In another embodiment, an ActA-encoding nucleotide of methods and compositions of the present invention comprises the sequence set forth in SEQ ID No: 4. In another embodiment, the ActA-encoding nucleotide is a homologue of SEQ ID No: 4. In another embodiment, the ActA-encoding nucleotide is a variant of SEQ ID No: 4. In another embodiment, the ActA-encoding nucleotide is a fragment of SEQ ID No: 4. In another embodiment, the ActA-encoding nucleotide is an isoform of SEQ ID No: 4. Each possibility represents a separate embodiment of the present invention.

In another embodiment, the ActA fragment is encoded by a recombinant nucleotide comprising the sequence:

Tttatcacgtacccatttccccgcatctttattttttaaatactttagggaaaa atggttttttgatttgcttttaaaggttgtggtgtagactcgtctgctgactgcatgcta-gaa tctaagtcactttcagaagcatccacaactgactctttcgccacttttctcttattt-gcttt tgttggtttatctggataagtaaggctttcaagctcactatccgacgacgc-tatggctttc ttcttttttaatttccgctgcgctatccgatgacagacctggatgacgacgctccact-tgc agagttggtcggtcgactcctgaagcctcttcatttatagccacatttcctgttt-gctcacc gttgttattattgttattcggacctttctctgcttttgctttcaacattgctatt-aggtctg ctttgttcgtattttcactttattcgattttttctagttcctcaatatcacgtgaacttact tcacgtgcagtttcgtatcttggtcccgtatttacctcgcttggctgctcttctgttttttc ttcttcccattcatctgtgtttagactggaatcttcgctatctgtcgctgcaaatattatgt cggggttaatcgtaatgcagttggcagtaatgaaaactaccatcatcgcacgcat (SEQ ID NO: 5). In another embodiment, the recombinant nucleotide has the sequence set forth in SEQ ID NO: 5. In another embodiment, an ActA-encoding nucleotide of methods and compositions of the present invention comprises the sequence set forth in SEQ ID No: 5. In another embodiment, the ActA-encoding nucleotide is a homologue of SEQ ID No: 5. In another embodiment, the ActA-encoding nucleotide is a variant of SEQ ID No: 5. In another embodiment, the ActA-encoding nucleotide is a fragment of SEQ ID No: 5. In another embodiment, the ActA-encoding nucleotide is an isoform of SEQ ID No: 5. Each possibility represents a separate embodiment of the present invention.

In another embodiment of methods and compositions of the present invention, a fragment of an ActA protein is fused to a heterologous antigen or fragment thereof. In another embodiment, the fragment of an ActA protein has the sequence as set forth in Genbank Accession No. AAF04762. In another embodiment, an ActA AA sequence of methods and compositions of the present invention comprises the sequence set forth in Genbank Accession No. AAF04762. In another embodiment, the ActA AA sequence is a homologue of Genbank Accession No. AAF04762. In another embodiment, the ActA AA sequence is a variant of Genbank Accession No. AAF04762. In another embodiment, the ActA AA sequence is a fragment of Genbank Accession No. AAF04762. In another embodiment, the ActA AA sequence is an isoform of Genbank Accession No. AAF04762. Each possibility represents a separate embodiment of the present invention.

An N-terminal fragment of an ActA protein utilized in methods and compositions of the present invention has, in another embodiment, the sequence set forth in SEQ ID NO: 6: MRAMMVVFITANCITINPDIIFAATDSEDS SLNT-DEWEEEKTEEQPSEVNTGPRYETA REVS SRDIKELEKSNKVRNTNKADLIAMLKEKAEKGPN-INNNNSEQTENAAINEEAS GADRPAIQVERRH-PGLPSDSAAEIKKRRKAIASSDSELESLTYPDKPTK-VNKKKVAKE SVADASESDLDSSMQSADESSPQPLKANQQPFFPK-VFKKIKDAGKWVRDKIDENPEV KKAIVDKSA-GLIDQLLTKKKSEEVNASDFPPPPTDEELRLALPETP-MLLGFNAPATSEP SSFEFPPPPTDEELRLALPETPMLLGFNAPATSEPSS-FEFPPPPTEDELEIIRETASSLDSS FTRGDLASLR-NAINRHSQNFSDFPPIPTEEELNGRGGRP. In another embodiment, the ActA fragment comprises the sequence set forth in SEQ ID NO: 6. In another embodiment, the ActA fragment is any other ActA fragment known in the art. Each possibility represents a separate embodiment of the present invention.

In another embodiment, the recombinant nucleotide encoding a fragment of an ActA protein comprises the sequence set forth in SEQ ID NO: 7

Atgcgtgcgatgatggtggttttcattactgccaattgcattacgattaac-cccgacataatatttgcagcgacagatagcgaagattcta gtctaaacacagat-gaatgggaagaagaaaaaacagaagagcaaccaagcgaggtaaatacgggac-caagatacgaaactgcacg
tgaagtaagttcacgtgatattaaagaactagaaaaatcgaataaagt-gagaaatacgaacaaagcagacctaatagcaatgttgaaag aaaaagca-gaaaaaggtccaaatatcaataataacaacagtgaacaaactgagaatgcggc-tataaatgaagaggcttcaggagccg
accgaccagctatacaagtggagcgtcgtcatccaggattgccatcgga-tagcgcagcggaaattaaaaaaagaaggaaagccatag catcatcggatagt-gagcttgaaagccttacttatccggataaaccaacaaaag-taaataagaaaaaagtggcgaaagagtcagttgcg
gatgcttctgaaagtgacttagattctagcatgcagtcagcagatgagtcttcacca-caaccttaaaagcaaaccaacaaccattttccc taaagtatt-taaaaaaataaaagatgcggggaaatgggtacgtgataaaatcgacgaaaatcct-gaagtaaagaaagcgattgttgata
aaagtgcagggttaattgaccaattattaaccaaaaagaaaagtgaagaggtaaat-gcttcggacttcccgccaccacctacggatgaa gagttaagacttgctttgccaga-gacaccaatgcttcttggttttaatgctcctgctacatcagaaccgagctcattc-gaatttccaccacca
cctacggatgaagagttaagacttgctttgccagagacgccaatgcttcttggttt-taatgctcctgctacatcggaaccgagctcgttcga atttccaccgcctccaaca-gaagatgaactagaaatcatccgggaaacagcatcctcgctagattctagtttta-caagagggatttagct
agtttgagaaatgctattaatcgccatagtcaaaatttctctgatttcccaccaatc-caacagaagaagagttgaacgggagaggcggt agacca. In another embodiment, the recombinant nucleotide has the sequence set forth in SEQ ID NO: 7. In another embodiment, the recombinant nucleotide comprises any other sequence that encodes a fragment of an ActA protein. Each possibility represents a separate embodiment of the present invention.

In another embodiment, the ActA fragment is encoded by a recombinant nucleotide comprising the sequence as set forth in Genbank Accession No. AF103807. In another embodiment, the recombinant nucleotide has the sequence set forth in Genbank Accession No. AF103807. In another embodiment, an ActA-encoding nucleotide of methods and compositions of the present invention comprises the sequence set forth in Genbank Accession No. AF103807. In another embodiment, the ActA-encoding nucleotide is a homologue of Genbank Accession No. AF103807. In another embodiment, the ActA-encoding nucleotide is a variant of Genbank Accession No. AF103807. In another embodiment, the ActA-encoding nucleotide is a fragment of Genbank Accession No. AF103807. In another embodiment, the ActA-encoding nucleotide is an isoform of Genbank Accession No. AF103807. Each possibility represents a separate embodiment of the present invention.

In another embodiment, the ActA fragment is any other ActA fragment known in the art. In another embodiment, a recombinant nucleotide of the present invention comprises any other sequence that encodes a fragment of an ActA protein. In another embodiment, the recombinant nucleotide comprises any other sequence that encodes an entire ActA protein. Each possibility represents a separate embodiment of the present invention.

In one embodiment, the live attenuated *Listeria* or recombinant *Listeria* provided herein expresses a PEST sequence peptide. In another embodiment of methods and compositions of the present invention, a PEST AA sequence is fused to the heterologous antigen or fragment. In another embodiment, the PEST AA sequence is KENSISSMAPPASPPASP-KTPIEKKHADEIDK (SEQ ID NO: 8). In another embodiment, the PEST sequence is KENSISSMAPPASPPASPK (SEQ ID No: 9).

In another embodiment, the PEST AA sequence is a PEST sequence from a *Listeria* ActA protein. In another embodiment, the PEST sequence is KTEEQPSEVNTGPR (SEQ ID NO: 10), KASVTDTSEGDLDSSMQSADESTPQPLK (SEQ ID NO: 11), KNEEVNASDFPPPPTDEELR (SEQ ID NO: 12), or RGGIPTSEEFSSLNSGDFTDDENSETTEEE-IDR (SEQ ID NO: 13). In another embodiment, the PEST-like sequence is a variant of the PEST sequence described hereinabove, which in one embodiment, is KESVVDASE SDLDSSMQSADESTPQPLK (SEQ ID NO: 14, K SEEVNASDFPPPPTDEELR (SEQ ID NO: 15), or RGG RPTSEEFSSLNSGDFTDDENSETTEEEIDR (SEQ ID NO: 16), as would be understood by a skilled artisan. In another embodiment, the PEST-like sequence is from *Listeria seeligeri* cytolysin, encoded by the lso gene. In another embodiment, the PEST sequence is RSEVTISPAETPESP-PATP (SEQ ID NO: 17). In another embodiment, the PEST sequence is from Streptolysin O protein of *Streptococcus sp*. In another embodiment, the PEST sequence is from *Streptococcus pyogenes* Streptolysin 0, e.g. KQN-TASTETTTTNEQPK (SEQ ID NO: 18) at AA 35-51. In another embodiment, the PEST-like sequence is from *Streptococcus equisimilis* Streptolysin O, e.g. KQNTAN-TETTTTNEQPK (SEQ ID NO: 19) at AA 38-54. In another embodiment, the PEST-like sequence has a sequence selected from SEQ ID NO: 8-16. In another embodiment, the PEST-like sequence has a sequence selected from SEQ ID NO: 8-19. In another embodiment, the PEST sequence is another PEST AA sequence derived from a prokaryotic organism.

Identification of PEST sequences is well known in the art, and is described, for example in Rogers S et al (Amino acid sequences common to rapidly degraded proteins: the PEST hypothesis. Science 1986; 234(4774):364-8) and Rechsteiner M et al (PEST sequences and regulation by proteolysis. Trends Biochem Sci 1996; 21(7):267-71). "PEST sequence" refers, in another embodiment, to a region rich in proline (P), glutamic acid (E), serine (S), and threonine (T) residues. In another embodiment, the PEST sequence is flanked by one or more clusters containing several positively charged amino acids. In another embodiment, the PEST sequence mediates rapid intracellular degradation of proteins containing it. In another embodiment, the PEST sequence fits an algorithm disclosed in Rogers et al. In another embodiment, the PEST sequence fits an algorithm disclosed in Rechsteiner et al. In another embodiment, the PEST sequence contains one or more internal phosphorylation sites, and phosphorylation at these sites precedes protein degradation.

In one embodiment, PEST sequences of prokaryotic organisms are identified in accordance with methods such as described by, for example Rechsteiner and Rogers (1996, Trends Biochem. Sci. 21:267-271) for Lm and in Rogers S et al (Science 1986; 234(4774):364-8). Alternatively, PEST AA sequences from other prokaryotic organisms can also be identified based on this method. Other prokaryotic organisms wherein PEST AA sequences would be expected to include, but are not limited to, other *Listeria* species. In one embodiment, the PEST sequence fits an algorithm disclosed in Rogers et al. In another embodiment, the PEST sequence fits an algorithm disclosed in Rechsteiner et al. In another embodiment, the PEST sequence is identified using the PEST-find program.

In another embodiment, identification of PEST motifs is achieved by an initial scan for positively charged AA R, H, and K within the specified protein sequence. All AA between the positively charged flanks are counted and only those motifs are considered further, which contain a number of AA equal to or higher than the window-size parameter. In another embodiment, a PEST-like sequence must contain at least 1 P, 1 D or E, and at least 1 S or T.

In another embodiment, the quality of a PEST motif is refined by means of a scoring parameter based on the local enrichment of critical AA as well as the motifs hydrophobicity. Enrichment of D, E, P, S and T is expressed in mass percent (w/w) and corrected for 1 equivalent of D or E, 1 of P and 1 of S or T. In another embodiment, calculation of hydrophobicity follows in principle the method of J. Kyte and R. F. Doolittle (Kyte, J and Dootlittle, R F. J. Mol. Biol. 157, 105 (1982).

In another embodiment, a potential PEST motif's hydrophobicity is calculated as the sum over the products of mole percent and hydrophobicity index for each AA species. The desired PEST score is obtained as combination of local enrichment term and hydrophobicity term as expressed by the following equation:

PEST score=0.55*DEPST−0.5*hydrophobicity index.

In another embodiment, "PEST sequence", "PEST-like sequence" or "PEST-like sequence peptide" refers to a peptide having a score of at least +5, using the above algorithm. In another embodiment, the term refers to a peptide having a score of at least 6. In another embodiment, the peptide has a score of at least 7. In another embodiment, the score is at least 8. In another embodiment, the score is at least 9. In another embodiment, the score is at least 10. In another embodiment, the score is at least 11. In another embodiment, the score is at least 12. In another embodiment, the score is at least 13. In another embodiment, the score is at least 14. In another embodiment, the score is at least 15. In another embodiment, the score is at least 16. In another embodiment, the score is at least 17. In another embodiment, the score is at least 18. In another embodiment, the score is at least 19. In another embodiment, the score is at least 20. In another embodiment, the score is at least 21. In another embodiment, the score is at least 22. In another embodiment, the score is at least 22. In another embodiment, the score is at least 24. In another embodiment, the score is at least 24. In another embodiment, the score is at least 25. In another embodiment, the score is at least 26. In another embodiment, the score is at least 27. In another embodiment, the score is at least 28. In another embodiment, the score is at least 29. In another embodiment, the score is at least 30. In another embodiment, the score is at least 32. In another embodiment, the score is at least 35. In another embodiment, the score is at least 38. In another embodiment, the score is at least 40. In another embodiment, the score is at least 45. Each possibility represents a separate embodiment of the present invention.

In another embodiment, the PEST sequence is identified using any other method or algorithm known in the art, e.g the CaSPredictor (Garay-Malpartida H M, Occhiucci J M, Alves J, Belizario J E. Bioinformatics. 2005 June; 21 Suppl 1:i169-76). In another embodiment, the following method is used:

A PEST index is calculated for each stretch of appropriate length (e.g. a 30-35 AA stretch) by assigning a value of 1 to the AA Ser, Thr, Pro, Glu, Asp, Asn, or Gln. The coefficient value (CV) for each of the PEST residue is 1 and for each of the other AA (non-PEST) is 0.

Each method for identifying a PEST-like sequence represents a separate embodiment of the present invention.

In another embodiment, the PEST sequence is any other PEST sequence known in the art. Each PEST sequence and type thereof represents a separate embodiment of the present invention.

"Fusion to a PEST sequence" refers, in another embodiment, to fusion to a protein fragment comprising a PEST sequence. In another embodiment, the term includes cases wherein the protein fragment comprises surrounding sequence other than the PEST sequence. In another embodiment, the protein fragment consists of the PEST sequence. Thus, in another embodiment, "fusion" refers to two peptides or protein fragments either linked together at their respective ends or embedded one within the other. Each possibility represents a separate embodiment of the present invention.

In another embodiment, provided herein is a vaccine comprising a recombinant form of *Listeria* of the present invention.

In another embodiment, provided herein, is a culture of a recombinant form of *Listeria* of the present invention.

In another embodiment, the *Listeria* of methods and compositions of the present invention is *Listeria monocytogenes*. In another embodiment, the *Listeria* is *Listeria ivanovii*. In another embodiment, the *Listeria* is *Listeria welshimeri*. In another embodiment, the *Listeria* is *Listeria seeligeri*. Each type of *Listeria* represents a separate embodiment of the present invention.

In one embodiment, attenuated *Listeria* strains, such as Lm delta-actA mutant (Brundage et al, 1993, Proc. Natl. Acad. Sci., USA, 90:11890-11894), *L. monocytogenes* delta-plcA (Camilli et al, 1991, J. Exp. Med., 173:751-754), or delta-ActA, delta INL-b (Brockstedt et 5 al, 2004, PNAS, 101:13832-13837) are used in the present invention. In another embodiment, attenuated *Listeria* strains are constructed by introducing one or more attenuating mutations, as will be understood by one of average skill in the art when equipped with the disclosure herein. Examples of such strains include, but are not limited to *Listeria* strains auxotrophic for aromatic amino acids (Alexander et al, 1993, Infection and Immunity 10 61:2245-2248) and mutant for the formation of lipoteichoic acids (Abachin et al, 2002, Mol. Microbiol. 43:1-14) and those attenuated by a lack of a virulence gene (see examples herein).

In another embodiment, the nucleic acid molecule of methods and compositions of the present invention is operably linked to a promoter/regulatory sequence. In another embodiment, the first open reading frame of methods and compositions of the present invention is operably linked to a promoter/regulatory sequence. In another embodiment, the second open reading frame of methods and compositions of the present invention is operably linked to a promoter/regulatory sequence. In another embodiment, each of the open reading frames are operably linked to a promoter/regulatory sequence. Each possibility represents a separate embodiment of the present invention.

The skilled artisan, when equipped with the present disclosure and the methods provided herein, will readily understand that different transcriptional promoters, terminators, carrier vectors or specific gene sequences (e.g. those in commercially available cloning vectors) can be used successfully in methods and compositions of the present invention. As is contemplated in the present invention, these functionalities are provided in, for example, the commercially available vectors known as the pUC series. In another embodiment, non-essential DNA sequences (e.g. antibiotic resistance genes) are removed. Each possibility represents a separate embodiment of the present invention. In another embodiment, a commercially available plasmid is used in the present invention. Such plasmids are available from a variety of sources, for example, Invitrogen (La Jolla, Calif.), Stratagene (La Jolla, Calif.), Clontech (Palo Alto, Calif.), or can be constructed using methods well known in the art.

Another embodiment is a plasmid such as pCR2.1 (Invitrogen, La Jolla, Calif.), which is a prokaryotic expression vector with a prokaryotic origin of replication and promoter/regulatory elements to facilitate expression in a prokaryotic organism. In another embodiment, extraneous nucleotide sequences are removed to decrease the size of the plasmid and increase the size of the cassette that can be placed therein.

Such methods are well known in the art, and are described in, for example, Sambrook et al. (1989, Molecular Cloning: A Laboratory Manual, Cold Spring Harbor Laboratory Press, New York) and Ausubei et al. (1997, Current Protocols in Molecular Biology, Green & Wiley, N.Y.).

Antibiotic resistance genes are used in the conventional selection and cloning processes commonly employed in molecular biology and vaccine preparation. Antibiotic resistance genes contemplated in the present invention include, but are not limited to, gene products that confer resistance to ampicillin, penicillin, methicillin, streptomycin, erythromycin, kanamycin, tetracycline, cloramphenicol (CAT), neomycin, hygromycin, gentamicin and others well known in the art. Each gene represents a separate embodiment of the present invention.

Methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.) In another embodiment, the *Listeria* vaccine strain of the present invention is transformed by electroporation. Each method represents a separate embodiment of the present invention.

In another embodiment, conjugation is used to introduce genetic material and/or plasmids into bacteria. Methods for conjugation are well known in the art, and are described, for example, in Nikodinovic J et al. (A second generation snp-derived *Escherichia coli-Streptomyces* shuttle expression vector that is generally transferable by conjugation. Plasmid. 2006 November; 56(3):223-7) and Auchtung J M et al (Regulation of a *Bacillus subtilis* mobile genetic element by intercellular signaling and the global DNA damage response. Proc Natl Acad Sci USA. 2005 Aug. 30; 102 (35):12554-9). Each method represents a separate embodiment of the present invention.

"Transforming," in one embodiment, is used identically with the term "transfecting," and refers to engineering a bacterial cell to take up a plasmid or other heterologous DNA molecule. In another embodiment, "transforming" refers to engineering a bacterial cell to express a gene of a plasmid or other heterologous DNA molecule. Each possibility represents a separate embodiment of the present invention.

Plasmids and other expression vectors useful in the present invention are described elsewhere herein, and can include such features as a promoter/regulatory sequence, an origin of replication for gram negative and gram positive bacteria, an isolated nucleic acid encoding a fusion protein and an isolated nucleic acid encoding an amino acid metabolism gene. Further, an isolated nucleic acid encoding a fusion protein and an amino acid metabolism gene will have a promoter suitable for driving expression of such an isolated nucleic acid. Promoters useful for driving expression in a bacterial system are well known in the art, and include bacteriophage lambda, the bla promoter of the beta-lactamase gene of pBR322, and the CAT promoter of the chloramphenicol acetyl transferase gene of pBR325. Further examples of prokaryotic promoters include the major right and left promoters of 5 bacteriophage lambda (PL and PR), the trp, recA, lacZ, lad, and gal promoters of *E. coli*, the alpha-amylase (Ulmanen et al, 1985. J. Bacteriol. 162:176-182) and the S28-specific promoters of *B. subtilis* (Gilman et al, 1984 Gene 32:11-20), the promoters of the bacteriophages of *Bacillus* (Gryczan, 1982, In: The Molecular Biology of the Bacilli, Academic Press, Inc., New York), and *Streptomyces* promoters (Ward et al, 1986, Mol. Gen. Genet. 203:468-478). Additional prokaryotic promoters contemplated in the present invention are reviewed in, for example, Glick (1987, J. Ind. Microbiol. 1:277-282); Cenatiempo, (1986, Biochimie, 68:505-516); and Gottesman, (1984, Ann. Rev. Genet. 18:415-442). Further examples of promoter/regulatory elements contemplated in the present invention include, but are not limited to the Listerial prfA promoter, the Listerial hly promoter, the Listerial p60 promoter and the Listerial ActA promoter (GenBank Acc. No. NC_003210) or fragments thereof.

In one embodiment, DNA encoding the recombinant non-hemolytic LLO is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen is ligated into a plasmid. Each method represents a separate embodiment of the present invention.

In another embodiment, the present invention further comprises a phage based chromosomal integration system for clinical applications. A host strain that is auxotrophic for essential enzymes, including, but not limited to, d-alanine racemase will be used, for example Lmdal(−)dat(−). In another embodiment, in order to avoid a "phage curing step," a phage integration system based on PSA is used (Lauer, et al., 2002 J Bacteriol, 184:4177-4186). This requires, in another embodiment, continuous selection by antibiotics to maintain the integrated gene. Thus, in another embodiment, the current invention enables the establishment of a phage based chromosomal integration system that does not require selection with antibiotics. Instead, an auxotrophic host strain will be complemented.

The recombinant proteins of the present invention are synthesized, in another embodiment, using recombinant DNA methodology. This involves, in one embodiment, creating a DNA sequence, placing the DNA in an expression cassette, such as the plasmid of the present invention, under the control of a particular promoter/regulatory element, and expressing the protein. DNA encoding the protein (e.g. non-hemolytic LLO) of the present invention is prepared, in another embodiment, by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 15 1859-1862); and the solid support method of U.S. Pat. No. 4,458,066.

In another embodiment, chemical synthesis is used to produce a single stranded oligonucleotide. This single stranded oligonucleotide is converted, in various embodiments, into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences can be obtained by the ligation of shorter sequences. In another embodiment, subsequences are cloned and the appropriate subsequences cleaved using appropriate restriction enzymes. The fragments are then be ligated to produce the desired DNA sequence.

In another embodiment, DNA encoding the recombinant protein of the present invention is cloned using DNA amplification methods such as polymerase chain reaction (PCR). Thus, the gene for non-hemolytic LLO is PCR amplified, using a sense primer comprising a suitable restriction site and an antisense primer comprising another restriction site, e.g. a non-identical restriction site to facilitate cloning.

In another embodiment, the recombinant fusion protein gene is operably linked to appropriate expression control sequences for each host. Promoter/regulatory sequences are described in detail elsewhere herein. In another embodiment, the plasmid further comprises additional promoter regulatory elements, as well as a ribosome binding site and a transcription termination signal. For eukaryotic cells, the control sequences will include a promoter and an enhancer derived from e.g. immunoglobulin genes, SV40, cytomegalovirus, etc., and a polyadenylation sequence. In another embodiment, the sequences include splice donor and acceptor sequences.

In one embodiment, the term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

In another embodiment, in order to select for an auxotrophic bacteria comprising the plasmid, transformed auxotrophic bacteria are grown on a media that will select for expression of the amino acid metabolism gene. In another embodiment, a bacteria auxotrophic for D-glutamic acid synthesis is transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. In another embodiment, a bacterium auxotrophic for D-alanine synthesis will grow in the absence of D-alanine when transformed and expressing the plasmid of the present invention if the plasmid comprises an isolated nucleic acid encoding an amino acid metabolism enzyme for D-alanine synthesis. Such methods for making appropriate media comprising or lacking necessary growth factors, supplements, amino acids, vitamins, antibiotics, and the like are well known in the art, and are available commercially (Becton-Dickinson, Franklin Lakes, N.J.). Each method represents a separate embodiment of the present invention.

In another embodiment, once the auxotrophic bacteria comprising the plasmid of the present invention have been selected on appropriate media, the bacteria are propagated in the presence of a selective pressure. Such propagation comprises growing the bacteria in media without the auxotrophic factor. The presence of the plasmid expressing an amino acid metabolism enzyme in the auxotrophic bacteria ensures that the plasmid will replicate along with the bacteria, thus continually selecting for bacteria harboring the plasmid. The skilled artisan, when equipped with the present disclosure and methods herein will be readily able to scale-up the production of the *Listeria* vaccine vector by adjusting the volume of the media in which the auxotrophic bacteria comprising the plasmid are growing.

The skilled artisan will appreciate that, in another embodiment, other auxotroph strains and complementation systems are adopted for the use with this invention.

In one embodiment, provided herein is a method of administering the composition of the present invention. In another embodiment, provided herein is a method of administering the vaccine of the present invention. In another embodiment, provided herein is a method of administering the recombinant polypeptide or recombinant nucleotide of the present invention. In another embodiment, the step of administering the composition, vaccine, recombinant polypeptide or recombinant nucleotide of the present invention is performed with an attenuated recombinant form of *Listeria* comprising the composition, vaccine, recombinant nucleotide or expressing the recombinant polypeptide, each in its own discrete embodiment. In another embodiment, the administering is performed with a different attenuated bacterial vector. In another embodiment, the administering is performed with a DNA vaccine (e.g. a naked DNA vaccine). In another embodiment, administration of a recombinant polypeptide of the present invention is performed by producing the recombinant protein, then administering the recombinant protein to a subject. Each possibility represents a separate embodiment of the present invention.

In one embodiment, the vaccine for use in the methods of the present invention comprises a recombinant *Listeria monocytogenes*, in any form or embodiment as described herein. In one embodiment, the vaccine for use in the present invention consists of a recombinant *Listeria monocytogenes* of the present invention, in any form or embodiment as described herein. In another embodiment, the vaccine for use in the methods of the present invention consists essentially of a recombinant *Listeria monocytogenes* of the present invention, in any form or embodiment as described herein. In one embodiment, the term "comprise" refers to the inclusion of a recombinant *Listeria monocytogenes* in the vaccine, as well as inclusion of other vaccines or treatments that may be known in the art. In another embodiment, the term "consisting essentially of" refers to a vaccine, whose functional component is the recombinant *Listeria monocytogenes*, however, other components of the vaccine may be included that are not involved directly in the therapeutic effect of the vaccine and may, for example, refer to components which facilitate the effect of the recombinant *Listeria monocytogenes* (e.g. stabilizing, preserving, etc.). In another embodiment, the term "consisting" refers to a vaccine, which contains the recombinant *Listeria monocytogenes*.

In another embodiment, the methods of the present invention comprise the step of administering a recombinant *Listeria monocytogenes*, in any form or embodiment as described herein. In one embodiment, the methods of the present invention consist of the step of administering a recombinant *Listeria monocytogenes* of the present invention, in any form or embodiment as described herein. In another embodiment, the methods of the present invention consist essentially of the step of administering a recombinant *Listeria monocytogenes* of the present invention, in any form or embodiment as described herein. In one embodiment, the term "comprise" refers to the inclusion of the step of administering a recombinant *Listeria monocytogenes* in the methods, as well as inclusion of other methods or treatments that may be known in the art. In another embodiment, the term "consisting essentially of" refers to a method, whose functional component is the administration of recombinant *Listeria monocytogenes*, however, other steps of the methods may be included that are not involved directly in the therapeutic effect of the methods and may, for example, refer to steps which facilitate the effect of the administration of recombinant *Listeria monocytogenes*. In one embodiment, the term "consisting" refers to a method of administering recombinant *Listeria monocytogenes* with no additional steps.

In another embodiment, the immune response elicited by methods and compositions of the present invention comprises a $CD8^+$ T cell-mediated response. In another embodiment, the immune response consists primarily of a $CD8^+$ T cell-mediated response. In another embodiment, the only detectable component of the immune response is a $CD8^+$ T cell-mediated response (see Examples 7-11).

In another embodiment, the immune response elicited by methods and compositions provided herein comprises a $CD4^+$ T cell-mediated response. In another embodiment, the immune response consists primarily of a $CD4^+$ T cell-mediated response. In another embodiment, the only detectable component of the immune response is a $CD4^+$ T cell-mediated response. In another embodiment, the $CD4^+$ T cell-mediated response is accompanied by a measurable antibody response against the antigen. In another embodiment, the $CD4^+$ T cell-mediated response is not accompanied by a measurable antibody response against the antigen (see Examples 7-11).

In another embodiment, the immune response elicited by methods and compositions provided herein comprises an innate immune response wherein M1 macrophages and dendritic cells (DCs) are activated.

In one embodiment, provided herein is a method of increasing intratumoral ratio of CD8+/T regulatory cells, whereby and in another embodiment, the method comprising the step of administering to the subject a composition comprising the recombinant polypeptide, recombinant *Listeria*, or recombinant vector of the present invention (see Examples 7-11).

In another embodiment, provided herein is a method of increasing intratumoral ratio of CD8+/T regulatory cells, whereby and in another embodiment, the method comprises the step of administering to the subject a composition comprising the recombinant polypeptide, recombinant *Listeria*, or recombinant vector of the present invention (see Examples 7-11).

In one embodiment, provided herein is a method of increasing intratumoral ratio of CD8+/myeloid-derived suppressor cells (MDSC), whereby and in another embodiment, the method comprises the step of administering to the subject a composition comprising the recombinant *Listeria*, or recombinant vector of the present invention.

In another embodiment, provided herein is a method of increasing the ratio of CD8+/myeloid-derived suppressor cells (MDSC) at sites of disease, whereby and in another embodiment, the method comprises the step of administering to the subject a composition comprising the recombinant *Listeria*, or recombinant vector of the present invention.

Common plasma markers in human MDSCs include CD33, CD11b, CD15, CD14 negative, MHC class II negative, HLA DR$^{low\ or\ -}$. Common intracellular markers include arginase, and iNOS. Further, human MDSCs' suppressive activity or mechanism includes use of nitric oxide (NO), arginase, or nitrotyrosine. In mice, myeloid-derived suppressor cells (MDSC) are CD11b and Gr-1 double positive and have also have been described as F4/80$^{int}$, CD11c$^{low}$, MHCII-/$^{low}$, Ly6C+. CD11b+/Gr-1+ cells that have immunosuppressive ability have been described to produce IFN-g. MDSCs can be monocytic and/or granulocytic as well.

In one embodiment, MDSCs at disease sites can unexpectedly inhibit both, the function of antigen-specific and non-specific T cell function, while spleen MDSCs can only inhibit the function of antigen-specific T cells. As demonstrated in the Examples below (see Examples 21-24), the live attenuated *Listeria* provided herein reduces the amount or quantity of suppressor cells in a disease thereby allowing CD8 T cell replication and infiltration at the disease site, for example, a tumor site.

Lm or sublytic doses of LLO in human epithelial Caco-2 cells induce the expression of IL-6 that reduces bacterial intracellular growth and causes over expression of inducible nitric oxide synthase (NOS). Nitric oxide appears to be an essential component of the innate immune response to Lm, having an important role in listericidal activity of neutrophils and macrophages, with a deficiency of inducible NO synthase (iNOS) causing susceptibility to Lm infection.

Lm infection also results in the generation of robust MHC Class 2 restricted CD4$^+$ T cell responses, and shifts the phenotype of CD4$^+$ T cells to Th-1. Further, CD4$^+$ T cell help is required for the generation and maintenance of functional CD8$^+$ T cell memory against Lm. Moreover, it has been reported infection of mice intraperitoneally with Lm caused a local induction of CD4$^+$ T$_{\gamma\delta}$ cells associated with IL-17 secretion in the peritoneal cavity however no changes were observed in the splenic or lymph node T cell populations after these injections. In addition, *Listeria* infection also involves other systems not essentially a part of the immune system but which support immune function to affect a therapeutic outcome, such as myelopoesis and vascular endothelial cell function.

Lm infected macrophages produce TNF-α, IL-18 and IL-12, all of which are important in inducing the production of IFN-γ and subsequent killing and degradation of Lm in the phagosome. IL-12 deficiency results in an increased susceptibility to listeriosis, which can be reversed through administration of IFN-γ. NK cells are the major source of IFN-γ in early infection. Upon reinfection memory CD8$^+$ T cells have the ability to produce IFN-γ in response to IL-12 and IL-18 in the absence of the cognate antigen. CD8$^+$ T cells co-localize with the macrophages and Lm in the T cell area of the spleen where they produce IFN-γ independent of antigen. IFN-γ production by CD8$^+$ T cells depends partially on the expression of LLO.

IFN-γ plays an important role in anti-tumor responses obtained by Lm-based vaccines. Although produced initially by NK cells, IFN-γ levels are subsequently maintained by CD4$^+$ T-helper cells for a longer period. Lm vaccines require IFN-γ for effective tumor regression, and IFN-γ is specifically required for tumor infiltration of lymphocytes. IFN-γ also inhibits angiogenesis at the tumor site in the early effector phase following vaccination.

A poorly described property of LLO, is its ability to induce epigenetic modifications affecting control of DNA expression. Extracellular LLO induces a dephosphorylation of the histone protein H3 and a similar deacetylation of the histone H4 in early phases of *Listeria* infection. This epigenetic effect results in reduced transcription of certain genes involved in immune function, thus providing a mechanism by which LLO may regulate the expression of gene products required for immune responses. Another genomic effect of LLO is its ability to increase NF-κβ translocation in association with the expression of ICAM and E-selectin, and the secretion of IL-8 and MCP-1. Another signaling cascade affected by LLO is the Mitogen Activated Protein Kinase (MAPK) pathway, resulting in increase of Ca$^{2+}$ influx across the cell membrane, which facilitates the entry of *Listeria* into endothelial cells and their subsequent infection.

LLO is also a potent inducer of inflammatory cytokines such as IL-6, IL-8, IL-12, IL-18, TNF-α, and IFN-γ, GM-CSF as well as NO, chemokines, and costimulatory molecules that are important for innate and adaptive immune responses. The proinflammatory cytokine-inducing property of LLO is thought to be a consequence of the activation of the TLR4 signal pathway. One evidence of the high Th1 cytokine-inducing activity of LLO is in that protective immunity to Lm can be induced with killed or avirulent Lm when administered together with LLO, whereas the protection is not generated in the absence of LLO. Macrophages in the presence of LLO release IL-1α, TNF-α, IL-12 and IL-18, which in turn activate NK cells to release IFN-γ resulting in enhanced macrophage activation.

IL-18 is also critical to resistance to Lm, even in the absence of IFN-γ, and is required for TNF-α and NO production by infected macrophages. A deficiency of caspase-1 impairs the ability of macrophages to clear Lm and causes a significant reduction in IFN-γ production and listericidal activity that can be reversed by IL-18. Recombinant IFN-γ injection restores innate resistance to listeriosis in caspase-1$^{-/-}$ mice. Caspase-1 activation precedes the cell death of macrophages infected with Lm, and LLO deficient mutants that cannot escape the phagolysosome have an impaired ability to activate caspase-1.

LLO secreted by cytosolic Lm causes specific gene upregulation in macrophages resulting in significant IFN-γ transcription and secretion. Cytosolic LLO activates a potent type I interferon response to invasive Lm independent of Toll-like receptors (TLR) without detectable activation of NF-KB and MAPK. One of the IFN I-specific apoptotic genes, TNF-α related apoptosis-inducing ligand (TRAIL), is up-regulated during Lm infection in the spleen. Mice lacking TRAIL are also more resistant to primary listeriosis coincident with lymphoid and myeloid cell death in the spleen.

Lm also secretes P60 which acts directly on naïve DCs to stimulate their maturation in a manner that permits activation of NK cells. Both activated DCs and IFN-γ that is produced by NK cells can boost cellular (Th1-type) immune responses. ActA stimulate toll receptors, for example TLR-5, which plays a fundamental role in pathogen recognition and activation of innate immune response.

In one embodiment, the Lm vaccines provided herein reduce the number of Tregs and MDSCs in a disease further provided herein. In another embodiment, Lm vaccines provided herein are useful to improve immune responses by reducing the number of Tregs and MDSCs at a specific site in a subject. Such a site can be an inflammation site due to allergies, trauma, infection, disease or the site can be a tumor site.

In another embodiment, both monocytic and granulocytic MDSCs purified from the tumors of *Listeria*-treated mice are less able to suppress the division of CD8+ T cells than MDSCs purified from the tumors of untreated mice, whereas monocytic and granulocytic MDSCs purified from the spleens of these same tumor-bearing mice show no change in their function after vaccination with *Listeria* (see Examples 7-11 herein). In one embodiment, this effect is seen because splenic MDSCs are only suppressive in an antigen-specific manner. Hence, treatment with *Listeria* has the distinct advantage that it allows for tumor-specific inhibition of tumor suppressive cells such as Tregs and MDSCs (see Examples 7-11 herein). Another unexpected advantage provided by the live attenuated *Listeria* of the methods and compositions provided herein is that there are lower amount of Tregs in the tumor, and the ones that persist lose the ability to suppress T cell replication (see Examples 7-11 herein).

In one embodiment, provided herein is a method of reducing the percentage of suppressor cells in a disease site in a subject, the method comprising the step of administering a live attenuated *Listeria* vaccine strain to the subject.

In another embodiment, provided herein is a method of reducing suppressor cells' ability to suppress T cell replication in a disease site in a subject, the method comprising the step of administering a live attenuated *Listeria* vaccine strain to said subject.

In one embodiment, reducing the number of the suppressor cells at a disease site effectively treats the disease. In another embodiment, reducing the number of the suppressor cells at the disease site enhances an anti-disease immune response in the subject having the disease at the disease site. In another embodiment, the immune response is a cell-mediated immune response. In another embodiment, the immune response is a tumor infiltrating T-lymphocytes (TILS) immune response.

In one embodiment, provided herein is a method of reducing the percentage of suppressor cells in a disease in a subject and enhancing a therapeutic response against the disease in the subject, the method comprising the step of administering a live attenuated *Listeria* vaccine strain to the subject, thereby reducing the percentage of suppressor cells in the disease and enhancing a therapeutic response against the disease in the subject.

In another embodiment, provided herein is a method of reducing suppressor cells' ability to suppress replication of T cells in a disease in a subject and enhancing a therapeutic response against the disease in the subject, the method comprising the step of administering a live attenuated *Listeria* vaccine strain to the subject.

In one embodiment, the term "percentage" is representative of the amount, quantity, or numbers, etc., of either Tregs, MDSCs, or CD8/CD4 T cells measures in an assay or in an immune response. In another embodiment, it refers to the amount, quantity, percentage, etc. of any composition, cell, protein, bacteria or *Listeria* cell provided herein.

In one embodiment, provided herein is a method of attenuating a recombinant *Listeria* vaccine strain, wherein the method comprises deleting the genomic prfA, inlC and actA genes, where in another embodiment, the attenuation is relative to the wild-type strain or a mutant strain having a mutant prfA, inlC, or actA, or any virulence gene thereof. In another embodiment, provided herein is a method of further enhancing the immunogenicity of a recombinant *Listeria* vaccine strain also provided herein, wherein the method comprises deleting the genomic prfA, inlC and actA genes. In one embodiment, provided herein is a method of attenuating a recombinant *Listeria* vaccine strain, wherein the method comprises deleting the genomic prfA, inlC or actA genes, where in another embodiment, the attenuation is relative to the wild-type strain or a mutant strain having a mutant prfA, inlC, or actA, or any virulence gene thereof. In another embodiment, provided herein is a method of further enhancing the immunogenicity of a recombinant *Listeria* vaccine strain also provided herein, wherein the method comprises deleting the genomic prfA, inlC or actA genes.

In another embodiment, provided herein is a method of eliciting an enhanced immune response in a subject recovering from cytotoxic treatment to a tumor or a cancer, the method comprising administering to said subject a composition comprising the recombinant *Listeria* strain provided herein. In another embodiment, the recombinant *Listeria* strain comprises a mutation or deletion of the inlC gene, an actA gene, a prfA gene, a PlcA gene, a PLcB gene, a dal gene or a dal/dat gene. In another embodiment, the recombinant *Listeria* strain comprises an inlC and actA mutation or deletion. In another embodiment, the recombinant *Listeria* strain comprises an inlC or actA mutation or deletion. In another embodiment, the recombinant *Listeria* strain consists of an inlC or actA mutation or deletion.

In one embodiment, the immune response elicited by the compositions and methods provided herein is not antigen specific.

In another embodiment, the present invention provides a method of reducing an incidence of cancer or infectious disease, comprising administering a composition of the present invention. In another embodiment, the present invention provides a method of ameliorating cancer or infectious disease, comprising administering a composition of the present invention. Each possibility represents a separate embodiment of the present invention.

In one embodiment, the cancer treated by a method of the present invention is breast cancer. In another embodiment, the cancer is a cervix cancer. In another embodiment, the cancer is an Her2 containing cancer. In another embodiment, the cancer is a melanoma. In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, it is a glioblastoma multiforme. In another embodiment, it is a hypoxic solid tumor. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma. Each possibility represents a separate embodiment of the present invention.

It is to be understood that the methods of the present invention may be used to treat any infectious disease, which in one embodiment, is bacterial, viral, microbial, microorganism, pathogenic, or combination thereof, infection. In another embodiment, the methods of the present invention are for inhibiting or suppressing a bacterial, viral, microbial, microorganism, pathogenic, or combination thereof, infection in a subject. In another embodiment, the present invention provides a method of eliciting a cytotoxic T-cell response against a bacterial, viral, microbial, microorganism, pathogenic, or combination thereof, infection in a subject. In another embodiment, the present invention provides a method of inducing an immune response against a bacterial, viral, microbial, microorganism, pathogenic, or combination thereof, infection in a subject. In one embodiment, the infection is viral, which in one embodiment, is HIV. In one embodiment, the infection is bacterial, which in one embodiment, is mycobacterial, which in one embodiment, is tuberculosis. In one embodiment, the infection is eukaryotic, which in one embodiment, is plasmodium, which in one embodiment, is malaria.

In one embodiment, the present invention provides a method of inducing an immune response in a subject having a concomitant helminth infection, where in another embodiment, the method comprises using a *Listeria* vaccine vector.

In another embodiment, the present invention provides a method of inducing an immune response in a subject having concomitant infectious disease and helminth infections, the method comprising administering to the subject a therapeutically effective dose of a *Listeria* vaccine vector, wherein the *Listeria* vaccine vector expresses and secretes an antigen of the infectious disease.

In another embodiment, the present invention provides a method of inducing an immune response in a subject having concomitant infectious disease and helminth infections, the method comprising administering to the subject a therapeutically effective dose of a *Listeria* vaccine vector, wherein the *Listeria* vaccine vector expresses and secretes an antigen of the infectious disease fused to an additional immunogenic polypeptide.

In another embodiment, the present invention provides a method of enhancing an innate immune response against an infectious disease in a subject, the method comprising the step of administering to the subject a therapeutically effective dose of the composition comprising the *Listeria* vaccine vector provided herein.

In one embodiment, the present invention provides a method of eliciting an enhanced immune response to an infectious disease in a subject, the method comprising administering to the subject a therapeutically effective dose of the composition comprising the *Listeria* vaccine vector provided herein. In another embodiment, the immune response is not antigen specific.

In another embodiment, the present invention provides a method of preventing the onset of an infectious disease in a subject, the method comprising the step of administering to the subject a therapeutically effective dose of the composition comprising the *Listeria* vaccine vector provided herein. In another embodiment, the immune response is not antigen specific.

In one embodiment, the present invention provides a method of treating an infectious disease in a subject, the method comprising the step of administering to the subject a therapeutically effective dose of the composition comprising the *Listeria* vaccine vector provided herein. In another embodiment, the immune response is not antigen specific.

In one embodiment, the infectious disease is one caused by, but not limited to, any one of the following pathogens: BCG/Tuberculosis, Malaria, Plasmodium falciparum, plasmodium malariae, plasmodium vivax, Rotavirus, Cholera, Diptheria-Tetanus, Pertussis, Haemophilus influenzae, Hepatitis B, Human papilloma virus, Influenza seasonal), Influenza A (H1N1) Pandemic, Measles and Rubella, Mumps, Meningococcus A+C, Oral Polio Vaccines, mono, bi and trivalent, Pneumococcal, Rabies, Tetanus Toxoid, Yellow Fever, *Bacillus anthracis* (anthrax), *Clostridium botulinum* toxin (botulism), *Yersinia pestis* (plague), Variola major (smallpox) and other related pox viruses, *Francisella tularensis* (tularemia), Viral hemorrhagic fevers, Arena viruses (LCM, Junin virus, Machupo virus, Guanarito virus, Lassa Fever), Bunyaviruses (Hantaviruses, Rift Valley Fever), Flaviruses (Dengue), Filo viruses (Ebola, Marburg), *Burkholderia pseudomallei, Coxiella burnetii* (Q fever), *Brucella* species (brucellosis), *Burkholderia mallei* (glanders), *Chlamydia psittaci* (Psittacosis), Ricin toxin (from *Ricinus communis*), Epsilon toxin of *Clostridium perfringens, Staphylococcus* enterotoxin B, Typhus fever (*Rickettsia prowazekii*), other Rickettsias, Food- and Waterborne Pathogens, Bacteria (Diarrheagenic *E. coli*, Pathogenic Vibrios, *Shigella* species, Salmonella BCG/, *Campylobacter jejuni, Yersinia enterocolitica*), Viruses (Caliciviruses, Hepatitis A, West Nile Virus, LaCrosse, Calif. encephalitis, VEE, EEE, WEE, Japanese Encephalitis Virus, Kyasanur Forest Virus, Nipah virus, hantaviruses, Tick borne hemorrhagic fever viruses, Chikungunya virus, Crimean-Congo Hemorrhagic fever virus, Tick borne encephalitis viruses, Hepatitis B virus, Hepatitis C virus, Herpes Simplex virus (HSV), Human immunodeficiency virus (HIV), Human papillomavirus (HPV)), Protozoa (*Cryptosporidium parvum, Cyclospora cayatanensis, Giardia lamblia, Entamoeba histolytica*, Toxoplasma), Fungi (Microsporidia), Yellow fever, Tuberculosis, including drug-resistant TB, Rabies, Prions, Severe acute respiratory syndrome associated coronavirus (SARS-CoV), *Coccidioides posadasii, Coccidioides immitis*, Bacterial vaginosis, *Chlamydia trachomatis*, Cytomegalovirus, *Granuloma inguinale, Hemophilus ducreyi, Neisseria gonorrhea, Treponema pallidum, Trichomonas vaginalis*, or any other infectious disease known in the art that is not listed herein.

In another embodiment, the infectious disease is a livestock infectious disease. In another embodiment, livestock diseases can be transmitted to man and are called "zoonotic diseases." In another embodiment, these diseases include, but are not limited to, Foot and mouth disease, West Nile Virus, rabies, canine parvovirus, feline leukemia virus, equine influenza virus, infectious bovine rhinotracheitis (IBR), pseudorabies, classical swine fever (CSF), IBR, caused by bovine herpesvirus type 1 (BHV-1) infection of cattle, and pseudorabies (Aujeszky's disease) in pigs, toxoplasmosis, anthrax, vesicular stomatitis virus, rhodococcus equi, Tularemia, Plague (*Yersinia pestis*), *trichomonas*.

In another embodiment of the methods of the present invention, the subject mounts an immune response against an antigen-expressing tumor or target antigen, thereby mediating anti-tumor effects.

In one embodiment, the recombinant *Listeria monocytogenes* for use in the present invention secretes a heterologous peptide. In another embodiment, the recombinant *Listeria monocytogenes* for use in the present invention expresses a heterologous peptide. In another embodiment, the recombinant *Listeria monocytogenes* for use in the present invention expresses and secretes a non-hemolytic LLO, as described herein.

In one embodiment, a treatment protocol of the present invention is therapeutic. In another embodiment, the protocol is prophylactic. In another embodiment, the vaccines of the present invention are used to protect people at risk for cancer such as breast cancer or other types of tumors because of familial genetics or other circumstances that predispose them to these types of ailments as will be understood by a skilled artisan. Similarly, in another embodiment, the vaccines of the present invention are used to protect people at risk for infectious disease; such as tuberculosis, malaria, influenza, and leishmaniasis. In another embodiment, the vaccines are used as a cancer immunotherapy in early stage disease, or after debulking of tumor growth by surgery, conventional chemotherapy or radiation treatment. Following such treatments, the vaccines of the present invention are administered so that the CTL response to the tumor antigen of the vaccine destroys remaining metastases and prolongs remission from the cancer. In another embodiment, vaccines of the present invention are used to effect the growth of previously established tumors and to kill existing tumor cells. Each possibility represents a separate embodiment of the present invention.

In another embodiment, the vaccines and immunogenic compositions utilized in any of the methods described above have any of the characteristics of vaccines and immunogenic compositions of the present invention. Each characteristic represents a separate embodiment of the present invention.

Various embodiments of dosage ranges are contemplated by this invention. In one embodiment, in the case of vaccine vectors, the dosage is in the range of 0.4 $LD_{50}$/dose. In another embodiment, the dosage is from about 0.4-4.9 $LD_{50}$/dose. In another embodiment the dosage is from about 0.5-0.59 $LD_{50}$/dose. In another embodiment the dosage is from about 0.6-0.69 $LD_{50}$/dose. In another embodiment the dosage is from about 0.7-0.79 $LD_{50}$/dose. In another embodiment the dosage is about 0.8 $LD_{50}$/dose. In another embodiment, the dosage is 0.4 $LD_{50}$/dose to 0.8 of the $LD_{50}$/dose.

In another embodiment, the dosage is $10^7$ bacteria/dose. In another embodiment, the dosage is $1.5 \times 10^7$ bacteria/dose. In another embodiment, the dosage is $2 \times 10^7$ bacteria/dose. In another embodiment, the dosage is $3 \times 10^7$ bacteria/dose. In another embodiment, the dosage is $4 \times 10^7$ bacteria/dose. In another embodiment, the dosage is $6 \times 10^7$ bacteria/dose. In another embodiment, the dosage is $8 \times 10^7$ bacteria/dose. In another embodiment, the dosage is $1 \times 10^8$ bacteria/dose. In another embodiment, the dosage is $1.5 \times 10^8$ bacteria/dose. In another embodiment, the dosage is $2 \times 10^8$ bacteria/dose. In another embodiment, the dosage is $3 \times 10^8$ bacteria/dose. In another embodiment, the dosage is $4 \times 10^8$ bacteria/dose. In another embodiment, the dosage is $6 \times 10^8$ bacteria/dose. In another embodiment, the dosage is $8 \times 10^8$ bacteria/dose. In another embodiment, the dosage is $1 \times 10^9$ bacteria/dose. In another embodiment, the dosage is $1.5 \times 10^9$ bacteria/dose. In another embodiment, the dosage is $2 \times 10^9$ bacteria/dose. In another embodiment, the dosage is $3 \times 10^9$ bacteria/dose. In another embodiment, the dosage is $5 \times 10^9$ bacteria/dose. In another embodiment, the dosage is $6 \times 10^9$ bacteria/dose. In another embodiment, the dosage is $8 \times 10^9$ bacteria/dose. In another embodiment, the dosage is $1 \times 10^{10}$ bacteria/dose. In another embodiment, the dosage is $1.5 \times 10^{10}$ bacteria/dose. In another embodiment, the dosage is $2 \times 10^{10}$ bacteria/dose. In another embodiment, the dosage is $3 \times 10^{10}$ bacteria/dose. In another embodiment, the dosage is $5 \times 10^{10}$ bacteria/dose. In another embodiment, the dosage is $6 \times 10^{10}$ bacteria/dose. In another embodiment, the dosage is $8 \times 10^{10}$ bacteria/dose. In another embodiment, the dosage is $8 \times 10^9$ bacteria/dose. In another embodiment, the dosage is $1 \times 10^{11}$ bacteria/dose. In another embodiment, the dosage is $1.5 \times 10^{11}$ bacteria/dose. In another embodiment, the dosage is $2 \times 10^{11}$ bacteria/dose. In another embodiment, the dosage is $3 \times 10^{11}$ bacteria/dose. In another embodiment, the dosage is $5 \times 10^{11}$ bacteria/dose. In another embodiment, the dosage is $6 \times 10^{11}$ bacteria/dose. In another embodiment, the dosage is $8 \times 10^{11}$ bacteria/dose. Each possibility represents a separate embodiment of the present invention.

In one embodiment, the adjuvant vaccine of the present invention comprise a vaccine given in conjunction. In another embodiment, the adjuvant vaccine of the present invention is administered following administration of a vaccine regimen, wherein the vaccine regimen is a viral, bacteria, nucleic acid, or recombinant polypeptide vaccine formulation.

"Adjuvant" typically refers, in another embodiment, to compounds that, when administered to an individual or tested in vitro, increase the immune response to an antigen in the individual or test system to which the antigen is administered. In another embodiment, an immune adjuvant enhances an immune response to an antigen that is weakly immunogenic when administered alone, i.e., inducing no or weak antibody titers or cell-mediated immune response. In another embodiment, the adjuvant increases antibody titers to the antigen. In another embodiment, the adjuvant lowers the dose of the antigen effective to achieve an immune response in the individual. However, in one embodiment, in the present invention, the adjuvant enhances an immune response in an antigen-unspecific manner in order to enable a heightened state of an immune response, as it applies to neonates, or in order to enable the recovery of the immune response following cytotoxic treatment, as it applies to older children and adults and also as further provided herein.

In another embodiment, the methods of the present invention further comprise the step of administering to the subject a booster vaccination. In one embodiment, the booster vaccination follows a single priming vaccination. In another embodiment, a single booster vaccination is administered after the priming vaccinations. In another embodiment, two booster vaccinations are administered after the priming vaccinations. In another embodiment, three booster vaccinations are administered after the priming vaccinations. In one embodiment, the period between a prime and a boost vaccine is experimentally determined by the skilled artisan. In another embodiment, the period between a prime and a boost vaccine is 1 week, in another embodiment it is 2 weeks, in another embodiment, it is 3 weeks, in another embodiment, it is 4 weeks, in another embodiment, it is 5 weeks, in another embodiment it is 6-8 weeks, in yet another embodiment, the boost vaccine is administered 8-10 weeks after the prime vaccine.

In one embodiment, a vaccine or immunogenic composition of the present invention is administered alone to a subject. In another embodiment, the vaccine or immunogenic composition is administered together with another cancer therapy. In another embodiment, the cancer therapy is chemotherapy, immuno therapy, radiation, surgery or any other type of therapy available in the art as will be understood by a skilled artisan. Each possibility represents a separate embodiment of the present invention.

In one embodiment, the construct or nucleic acid molecule is integrated into the Listerial chromosome using homologous recombination. Techniques for homologous recombination are well known in the art, and are described, for example, in Baloglu S, Boyle S M, et al. (Immune responses of mice to vaccinia virus recombinants expressing either *Listeria monocytogenes* partial listeriolysin or *Brucella abortus* ribosomal L7/L12 protein. Vet Microbiol 2005, 109(1-2): 11-7); and Jiang L L, Song H H, et al., (Characterization of a mutant *Listeria monocytogenes* strain expressing green fluorescent protein. Acta Biochim Biophys Sin (Shanghai) 2005, 37(1): 19-24). In another embodiment, homologous recombination is performed as described in U.S. Pat. No. 6,855,320. In this case, a recombinant Lm strain that expresses E7 was made by chromosomal integration of the E7 gene under the control of the hly promoter and with the inclusion of the hly signal sequence to ensure secretion of the gene product, yielding the recombinant referred to as Lm-AZ/E7. In another embodiment, a temperature sensitive plasmid is used to select the recombinants. Each technique represents a separate embodiment of the present invention.

In another embodiment, the construct or nucleic acid molecule is integrated into the Listerial chromosome using transposon insertion. Techniques for transposon insertion are well known in the art, and are described, inter alia, by Sun et al. (Infection and Immunity 1990, 58: 3770-3778) in the construction of DP-L967. Transposon mutagenesis has the advantage, in another embodiment, that a stable genomic insertion mutant can be formed but the disadvantage that the position in the genome where the foreign gene has been inserted is unknown.

In another embodiment, the construct or nucleic acid molecule is integrated into the Listerial chromosome using phage integration sites (Lauer P, Chow M Y et al, Construction, characterization, and use of two *Listeria monocytogenes* site-specific phage integration vectors. J Bacteriol 2002; 184(15): 4177-86). In certain embodiments of this method, an integrase gene and attachment site of a bacteriophage (e.g. U153 or PSA listeriophage) is used to insert the heterologous gene into the corresponding attachment site, which may be any appropriate site in the genome (e.g. comK or the 3' end of the arg tRNA gene). In another embodiment, endogenous prophages are cured from the attachment site utilized prior to integration of the construct or heterologous gene. In another embodiment, this method results in single-copy integrants. Each possibility represents a separate embodiment of the present invention.

In another embodiment, one of various promoters is used to express protein containing same. In one embodiment, an Lm promoter is used, e.g. promoters for the genes hly, actA, plcA, plcB and mpl, which encode the Listerial proteins hemolysin, ActA, phosphotidylinositol-specific phospholipase, phospholipase C, and metalloprotease, respectively. Each possibility represents a separate embodiment of the present invention.

In another embodiment, the construct or nucleic acid molecule is expressed from an episomal vector, with an endogenous nucleic acid sequence encoding an LLO, PEST or ActA sequence or functional fragments thereof. In another embodiment, the construct or nucleic acid molecule comprises a first and at least a second open reading frame each encoding a first and at least a second polypeptide, wherein the first and the at least second polypeptide each comprise a heterologous antigen or a functional fragment thereof fused to an endogenous PEST-containing polypeptide. Such compositions are described in U.S. patent application Ser. No. 13/290,783, incorporated by reference herein in its entirety.

In another embodiment, the PEST-containing polypeptide is a truncated non-hemolytic LLO, an N-terminal ActA, or a PEST sequence.

In another embodiment, provided herein is a recombinant *Listeria* strain comprising an episomal recombinant nucleic acid molecule, the nucleic acid molecule comprising a first and at least a second open reading frame each encoding a first and at least a second polypeptide, wherein the first and the at least second polypeptide each comprise a heterologous antigen or a functional fragment thereof fused to an endogenous PEST-containing polypeptide, wherein the nucleic acid further comprises an open reading frame encoding a plasmid replication control region. Such compositions are described in U.S. patent application Ser. No. 13/290,783, incorporated by reference herein in its entirety.

In another embodiment, methods and compositions of the present invention utilize a homologue of a heterologous antigen or LLO sequence of the present invention. The terms "homology," "homologous," etc, when in reference to any protein or peptide, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in one embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 1-41 of greater than about 70%. In another embodiment, "homology" refers to identity to a sequence selected from SEQ ID No: 1-41 of greater than about 70%. In another embodiment, the identity is greater than about 75%. In another embodiment, the identity is greater than about 78%. In another embodiment, the identity is greater than about 80%. In another embodiment, the identity is greater than about 82%. In another embodiment, the identity is greater than about 83%. In another embodiment, the identity is greater than about 85%. In another embodiment, the identity is greater than about 87%. In another embodiment, the identity is greater than about 88%. In another embodiment, the identity is greater than about 90%. In another embodiment, the identity is greater than about 92%. In another embodiment, the identity is greater than about 93%. In another embodiment, the identity is greater than about 95%. In another embodiment, the identity is greater than about 96%. In another embodiment, the identity is greater than about 97%. In another embodiment, the identity is greater than about 98%. In another embodiment, the identity is greater than about 99%. In another embodiment, the identity is 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

In one embodiment of the present invention, "nucleic acids" refers to a string of at least two base-sugar-phosphate combinations. The term includes, in one embodiment, DNA and RNA. "Nucleotides" refers, in one embodiment, to the monomeric units of nucleic acid polymers. RNA may be, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA may be in form of plasmid DNA, viral DNA, linear DNA, or chromosomal DNA or derivatives of these groups. In addition, these forms of DNA and RNA may be single, double, triple, or quadruple stranded. The term also includes, in another embodiment, artificial nucleic acids that may contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

The terms "contacting" or "administering," in one embodiment, refer to directly contacting the cancer cell or tumor with a composition of the present invention. In another embodiment, the terms refer to indirectly contacting the cancer cell or tumor with a composition of the present invention. In another embodiment, methods of the present invention include methods in which the subject is contacted with a composition of the present invention after which the composition is brought in contact with the cancer cell or tumor by diffusion or any other active transport or passive transport process known in the art by which compounds circulate within the body. Each possibility represents a separate embodiment of the present invention.

In another embodiment, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals or organisms. This can be readily carried out by using hybridization probes to identify the same genetic locus in a variety of individuals or organisms. Any and all such nucleotide variations and resulting amino acid polymorphisms or variations that are the result of natural allelic variation and that do not alter the functional activity are intended to be within the scope of the invention.

Pharmaceutical Compositions

The pharmaceutical compositions containing vaccines and compositions of the present invention are, in another embodiment, administered to a subject by any method known to a person skilled in the art, such as parenterally, paracancerally, transmucosally, transdermally, intramuscularly, intravenously, intra-dermally, subcutaneously, intra-peritoneally, intra-ventricularly, intra-cranially, intra-vaginally or intra-tumorally.

In another embodiment of the methods and compositions provided herein, the vaccines or compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a gelatin capsule.

In another embodiment, the vaccines or compositions are administered by intravenous, intra-arterial, or intra-muscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to inducing remission. In another embodiment, "treating" refers to slowing the progression of a disease. The terms "reducing", "suppressing" and "inhibiting" refer in another embodiment to lessening or decreasing. Each possibility represents a separate embodiment of the present invention.

The term "therapeutically effective dose" or "therapeutic effective amount" means a dose that produces the desired effect for which it is administered. The exact dose will be ascertainable by one skilled in the art using known techniques.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Experimental Methods

Bacterial Strains, Transformation and Selection

E. coli strain MB2159 was used for transformations, using standard protocols. Bacterial cells were prepared for electroporation by washing with $H_2O$.

E. coli strain MB2159 (Strych U et al, FEMS Microbiol Lett. 2001 Mar. 15; 196(2):93-8) is an alr (−)/dadX (−) deficient mutant that is not able to synthesize D-alanine racemase. Listeria strain Lm dal(−)/dat(−) (Lmdd) similarly is not able to synthesize D-alanine racemase due to partial deletions of the dal and the dat genes.

Plasmid Constructions

Using the published sequence of the plcA gene (Mengaud et al., Infect. Immun. 1989 57, 3695-3701), PCR was used to amplify the gene from chromosomal DNA. The amplified product was then ligated into pAM401 using SalI- and XbaI-generated DNA ends to generate pDP1462.

Plasmid pDP1500, containing prfA alone, was constructed by deleting the plcA gene, bases 429 to 1349 (Mengaud et al., supra), from pDP1462 after restriction with XbaI and PstI, treatment of the DNA ends with T4 DNA polymerase to make them blunt, and intramolecular ligation.

Plasmid pDP1499, containing the plcA promoter and a portion of the 3' end of plcA, was constructed by deleting a plcA internal fragment, bases 428 to 882 (Mengaud et al., Infect. Immun. 1989 57, 3695-3701), from pDP1339 after restriction with PstI and NsiI and intramolecular ligation.

pDP1526 (pKSV7::ΔplcA) was constructed by a single three-part ligation of pKSV7 restricted with BAMHI and XbaI, the 468 bp XbaI and NsiI-generated fragment from pAM401::plcA containing the 5' end of plcA (bases 882 to 1351; Mengaud et al., supra) and, the 501 bp PstI- and BamHI-generated fragment from pAM401::plcA prfA containing the 3' end of plcA (bases 77 to 429; Mengaud et al., supra).

The prfA promoter, bases 1-429 (Mengaud et al., supra), was isolated by EcoRI and PstI double digestion of pDP1462 and the fragment was subsequently ligated into EcoRI- and PstI-restricted pKSV7 to generate pDP1498. Two random HindIII-generated 10403S chromosomal DNA fragments, approximately 3 kb in length, were ligated into HindIII-restricted pKSV7, to generate the random integration control plasmids pDP1519 and pDP1521.

Construction of L. Monocytogenes Mutant Strains

L. monocytogenes strain DP-L1387 was isolated as a mutant with reduced lecithinase (PC-PLC) from a Tn917-LTV3 bank of SLCC 5764, constructed as previously described (Camilli et al., J. Bacteriol. 1990, 172, 3738-3744). The site of Tn917-LTV3 insertion was determined by sequencing one transposon-chromosomal DNA junction as previously described (Sun et al., Infect. Immun. 1990 58, 3770-3778). L. monocytogenes was transformed with plasmid DNA as previously described (Camilli et al., supra). Selective pressure for maintenance of pAM401, pKSV7, and their derivatives in L. monocytogenes was exerted in the presence of 10 .mu.g of chloramphenicol per ml of media. In addition, maintenance of pKSV7 derivatives required growth at 30° C., a permissive temperature for plasmid replication in Gram-positive bacteria.

Integration of pKSV7 derivatives into the L. monocytogenes chromosome occurred by homologous recombination between L. monocytogenes DNA sequences on the plasmids and their corresponding chromosomal alleles. Integration mutants were enriched by growth for approximately 30 generations at 40° C., a non-permissive temperature for pKSV7 replication, in Brain Heart Infusion (BHI) broth containing 10 .mu.g chloramphenicol per ml of media. Each integration strain was subsequently colony purified on BHI agar containing 10 .mu.g chloramphenicol per ml of media and incubated at 40° C. Southern blot analyses of chromosomal DNA isolated from each integration strain confirmed the presence of the integrated plasmid.

Construction of DP-L1552 is achieved by integration of the pKSV7 derivative, pDP1526, to generate a merodiploid intermediate was done as described above. Spontaneous excision of the integrated plasmid, through intramolecular homologous recombination, occurred at a low frequency. Bacteria in which the plasmid had excised from the chromosome were enriched by growth at 30° C. in BHI broth for approximately 50 generations. The nature of the selective pressure during this step was not known but may be due to a slight growth defect of strains containing integrated temperature-sensitive plasmids. Approximately 50% of excision events, i.e., those resulting from homologous recombination between sequences 3' of the deletion, resulted in allelic exchange of ΔplcA for the wild-type allele on the chromosome.

The excised plasmids were cured by growing the bacteria at 40° C. in BHI for approximately 30 generations. Bacteria cured of the plasmid retaining the ΔplcA allele on the chromosome were identified by their failure to produce a zone of turbidity surrounding colonies after growth on BHI agar plates containing a 5 ml overlay of BHI agar/2.5% egg yolk/2.5% phosphate-buffered saline (PBS) (BHI/egg yolk agar). The turbid zones resulted from PI-PLC hydrolysis of PI in the egg yolk, giving an insoluble diacylglycerol precipitate. The correct plcA deletion on the *L. monocytogenes* chromosome was confirmed by amplifying the deleted allele using PCR and sequencing across the deletion.

Thus, PI-PLC negative mutants (plcA deletion mutants) may be used according to the present invention to generate attenuated *L. monocytogenes* vaccines. Other mutants were made using the same method, namely, an actA deletion mutant, a plcB deletion mutant, and a double mutant lacking both plcA and plcB, all of which may also be used according to the present disclosure to generate attenuated *L. monocytogenes* vaccines. Given the present disclosure, one skilled in the art would be able to create other attenuated mutants in addition to those mentioned above.

Construction of Lmdd

The dal gene was initially inactivated by means of a double-allelic exchange between the chromosomal gene and the temperature-sensitive shuttle plasmid pKSV7 (Smith K et al, Biochimie. 1992 July-August; 74(7-8):705-11) carrying an erythromycin resistance gene between a 450-bp fragment from the 5' end of the original 850-bp dal gene PCR product and a 450-bp fragment from the 3' end of the dal gene PCR product. Subsequently, a dal deletion mutant covering 82% of the gene was constructed by a similar exchange reaction with pKSV7 carrying homology regions from the 5' and 3' ends of the intact gene (including sequences upstream and downstream of the gene) surrounding the desired deletion. PCR analysis was used to confirm the structure of this chromosomal deletion.

The chromosomal dat gene was inactivated by a similar allelic exchange reaction. pKSV7 was modified to carry 450-bp fragments derived by PCR from both the 5' and 3' ends of the intact dat gene (including sequences upstream and downstream of the gene). These two fragments were ligated by appropriate PCR. Exchange of this construct into the chromosome resulted in the deletion of 30% of the central bases of the dat gene, which was confirmed by PCR analysis.

Bacterial Culture and In Vivo Passaging of *Listeria*

*E. coli* were cultured following standard methods. *Listeria* were grown at 37° C., 250 rpm shaking in LB media (Difco, Detroit, Mich.). +50 μg/ml streptomycin, and harvested during exponential growth phase. For Lm-LLOE7, 37 μg/ml chloramphenicol was added to the media. For growth kinetics determinations, bacteria were grown for 16 hours in 10 ml of LB+antibiotics. The $OD_{600nm}$ was measured and culture densities were normalized between the strains. The culture was diluted 1:50 into LB+suitable antibiotics and D-alanine if applicable.

Passaging of Lm in Mice $1\times10^8$ CFU were injected intraperitoneally (ip.) into C57BL/6 mice. On day three, spleens were isolated and homogenized in PBS. An aliquot of the spleen suspension was plated on LB plates with antibiotics as applicable. Several colonies were expanded and mixed to establish an injection stock.

Construction of Antibiotic Resistance Factor Free Plasmid pTV3

Construction of p60-dal Cassette.

The first step in the construction of the antibiotic resistance gene-free vector was construction of a fusion of a truncated p60 promoter to the dal gene. The Lm alanine racemase (dal) gene (forward primer: 5'-CCA TGG TGA CAG GCT GGC ATC-3'; SEQ ID NO: 20) (reverse primer: 5'-GCT AGC CTA ATG GAT GTA TTT TCT AGG-3'; SEQ ID NO: 21) and a minimal p60 promoter sequence (forward primer: 5'-TTA ATT AAC AAA TAG TTG GTA TAG TCC-3'; SEQ ID No: 22) (reverse primer: 5'-GAC GAT GCC AGC CTG TCA CCA TGG AAA ACT CCT CTC-3'; SEQ ID No: 23) were isolated by PCR amplification from the genome of Lm strain 10403S. The primers introduced a PacI site upstream of the p60 sequence, an NheI site downstream of the dal sequence (restriction sites in bold type), and an overlapping dal sequence (the first 18 bp) downstream of the p60 promoter for subsequent fusion of p60 and dal by splice overlap extension (SOE)-PCR. The sequence of the truncated p60 promoter was: CAAATAGTTGGTATAGTCCTCTTTAGCCTTTGGAGTATTATCTCATCATTTGTTTTT TAGGTGAAAACTGGGTAAACTTAGTATTATCAATATAAAATTAATTCTCAAATAC TTAATTACGTACTGGGATTTTCTGAAAAAAGAGAGGAGTTTTCC (SEQ ID NO: 24 Kohler et al, J Bacteriol 173: 4668-74, 1991). Using SOE-PCR, the p60 and dal PCR products were fused and cloned into cloning vector pCR2.1 (Invitrogen, La Jolla, Calif.).

Removal of Antibiotic Resistance Genes from pGG55.

The subsequent cloning strategy for removing the Chloramphenicol acetyltransferase (CAT) genes from pGG55 and introducing the p60-dal cassette also intermittently resulted in the removal of the gram-positive replication region (oriRep; Brantl et al, Nucleic Acid Res 18: 4783-4790, 1990). In order to re-introduce the gram-positive oriRep, the oriRep was PCR-amplified from pGG55, using a 5'-primer that added a NarI/EheI site upstream of the sequence (GGCGCCACTAACTCAACGCTAGTAG, SEQ ID NO: 25) and a 3'-primer that added a NheI site downstream of the sequence (GCTAGCCAGCAAAGAAAAACAAACACG, SEQ ID NO: 26). The PCR product was cloned into cloning vector pCR2.1 and sequence verified.

In order to incorporate the p60-dal sequence into the pGG55 vector, the p60-dal expression cassette was excised from pCR-p60dal by PacI/NheI double digestion. The replication region for gram-positive bacteria in pGG55 was amplified from pCR-oriRep by PCR (primer 1,5'-GTC GAC GGT CAC CGG CGC CAC TAA CTC AAC GCT AGT AG-3'; SEQ ID No: 27); (primer 2,5'-TTA ATT AAG CTA GCC AGC AAA GAA AAA CAA ACA CG-3'; SEQ ID No: 28) to introduce additional restriction sites for EheI and NheI. The PCR product was ligated into pCR2.1-TOPO (Invitrogen, Carlsbad, Calif.), and the sequence was verified. The replication region was excised by EheI/NheI digestion, and vector pGG55 was double digested with EheI and NheI, removing both CAT genes from the plasmid simultaneously. The two inserts, p60-dal and oriRep, and the pGG55 fragment were ligated together, yielding pTV3 (FIG. 1). pTV3 also contains a prfA (pathogenicity regulating factor A) gene. This gene is not necessary for the function of pTV3, but can be used in situations wherein an additional selected marker is required or desired.

Preparation of DNA for Real-Time PCR

Total *Listeria* DNA was prepared using the Masterpure® Total DNA kit (Epicentre, Madison, Wis.). *Listeria* were cultured for 24 hours at 37° C. and shaken at 250 rpm in 25 ml of Luria-Bertoni broth (LB). Bacterial cells were pelleted by centrifugation, resuspended in PBS supplemented with 5 mg/ml of lysozyme and incubated for 20 minutes at 37° C., after which DNA was isolated.

In order to obtain standard target DNA for real-time PCR, the LLO-E7 gene was PCR amplified from pGG55 (5'-ATGAAAAAAATAATGCTAGTTTTTATTAC-3' (SEQ ID NO: 29); 5'-GCGGCCGCTTAATGATGATGATGATGAT-GTGGTTTCTG AGAACAGATG-3' (SEQ ID NO: 30)) and cloned into vector pETblue1 (Novagen, San Diego, Calif.). Similarly, the plcA amplicon was cloned into pCR2.1. *E. coli* were transformed with pET-LLOE7 and pCR-plcA, respectively, and purified plasmid DNA was prepared for use in real-time PCR.

Real-Time PCR

Taqman primer-probe sets (Applied Biosystems, Foster City, Calif.) were designed using the ABI PrimerExpress software (Applied Biosystems) with E7 as a plasmid target, using the following primers: 5'-GCAAGTGTGACTC-TACGCTTCG-3' (SEQ ID NO: 31); 5'-TGCCCATTAACA-GGTCTTCCA-3' (SEQ ID NO: 32); 5'-FAM-TGCGTA CAAAGCACACACGTAGACATTCGTAC-TAMRA-3' (SEQ ID NO: 33) and the one-copy gene plcA (TGACATCGTTTGTGTTTGAGCTAG-3' (SEQ ID NO: 34, 5'-GCAGCGCTCTCTATACCAGGTAC-3' (SEQ ID NO: 35); 5'-TET-TTAATGTCCATGTTA TGTCTCCGT-TATAGCTCATCGTA-TAMRA-3'; SEQ ID NO: 36) as a *Listeria* genome target.

0.4 µM primer and 0.05 mM probe were mixed with PuRE Taq RTG PCR beads (Amersham, Piscataway, N.J.) as recommended by the manufacturer. Standard curves were prepared for each target with purified plasmid DNA, pET-LLOE7 and pCR-plcA (internal standard) and used to calculate gene copy numbers in unknown samples. Mean ratios of E7 copies/plcA copies were calculated based on the standard curves and calibrated by dividing the results for Lmdd-TV3 and Lm-LLOE7 with the results from Lm-E7, a *Listeria* strain with a single copy of the E7 gene integrated into the genome. All samples were run in triplicate in each qPCR assay which was repeated three times. Variation between samples was analyzed by Two-Way ANOVA using the KyPlot software. Results were deemed statistically significant if $p<0.05$.

Growth Measurements

Bacteria were grown at 37° C., 250 rpm shaking in Luria Bertani (LB) Medium +/- 100 micrograms (µg)/ml D-alanine and/or 37 µg/ml chloramphenicol. The starting inoculum was adjusted based on $OD_{600}$ nm measurements to be the same for all strains.

Hemolytic Lysis Assay $4 \times 10^9$ CFU of *Listeria* were thawed, pelleted by centrifugation (1 minute, 14000 rpm) and resuspended in 100 µl PBS, pH 5.5 with 1 M cysteine. Bacteria were serially diluted 1:2 and incubated for 45 minutes at 37° C. in order to activate secreted LLO. Defibrinated total sheep blood (Cedarlane, Hornby, Ontario, Canada) was washed twice with 5 volumes of PBS and three to four times with 6 volumes of PBS-Cysteine until the supernatant remained clear, pelleting cells at 3000×g for 8 minutes between wash steps, then resuspended to a final concentration of 10% (v/v) in PBS-Cysteine. 100 µl of 10% washed blood cells were mixed with 100 µl of *Listeria* suspension and incubated for additional 45 minutes at 37° C. Un-lysed blood cells were then pelleted by centrifugation (10 minutes, 1000×g). 100 µl of supernatant was transferred into a new plate and the $OD_{530nm}$ was determined and plotted against the sample dilution.

Therapeutic Efficacy of Lmdd-Tv3

$10^5$ TC-1 (ATCC, Manassas, Va.) were implanted subcutaneously in C57BL/6 mice (n=8) and allowed to grow for about 7 days, after which tumors were palpable. TC-1 is a C57BL/6 epithelial cell line that was immortalized with HPV E6 and E7 and transformed with activated ras, which forms tumors upon subcutaneous implantation. Mice were immunized with 0.1 $LD_{50}$ of the appropriate *Listeria* strain on days 7 and 14 following implantation of tumor cells. A non-immunized control group (naïve) was also included. Tumor growth was measured with electronic calipers.

Construction of LmddAinlC

The deletions in the *Listeria* chromosome are introduced by homologous recombination between a target gene and homologous sequences present on the plasmid, which is temperature sensitive for DNA replication. After transformation of plasmid into the host, the integration of the plasmid into the chromosome by single crossover event is selected during growth at non-permissive temperature (42° C.) while maintaining selective pressure. Subsequent growth of co-integrates at permissive temperatures (30° C.) leads to second recombination event, resulting in their resolution.

To create deletion mutant, DNA fragments that are present upstream and downstream of inl C region (indicated in the figure is amplified by PCR (indicated in FIGS. 2 and 3 and respective SEQ ID NO: 37 and SEQ ID NO: 38).

(SEQ ID NO: 37)
atggcgcgggatggtatactatacaagcgtatggttcaaaaagatact ttgaattaagaagtacaataaagttaacttcattagacaaaaagaaaa aacaaggaagaatagtacatagttataaatacttggagagtgaggtgt aatatgggggcagctgattttgggttttcatatatgtagtttcaaga ttagccattgttgcggcagtagtttacttcttatacttattgagaaaa attgcaaataaatagaaaaaaagccttgtcaaacgaggcttttttat gcaaaaaatacgacgaatgaagccatgtgagacaatttggaatagcag acaacaaggaaggtagaacatgttttgaaaaatttactgattgcgatt attattaacgcttgttaatttaaacatctcttattttgctaacatat aagtatacaaagggacataaaaaggttaacagcgtttgttaaatagga agtatatgaaaatcctcttttgtgtttctaaatttattttaaggagt ggaga atgttgaaaaaaaataattggttacaaaatgcagtaatagcaa tgctagtgttaattgtaggtctgtgcattaatatgggttctggaacaa aagtacaagctgagagtattcaacgaccaacgcctattaaccaagttt ttccagatcccggcctagcgaatgcagtgaaacaaaatttagggaagc aaagtgttacagaccttgtatcacaaaaggaactatctggagtacaaa atttcaatggagataatagcaacattcaatctcttgcgggaatgcaat ttttcactaatttaaaagaacttcatctatcccataatcaaataagtg accttagtcctttaaaggatctaactaagttagaagagctatctgtga atagaaacagactgaaaaatttaaacggaattccaagtgcttgtttat ctcgcttgtttttagataacaacgaactcagagatactgactcgctta ttcatttgaaaaatctagaaatcttatctattcgtaataataagttaa aaagtattgtgatgcttggttttttatcaaaactagaggtattagatt tgcatggtaatgaaataacaaatacaggtggactaactagattgaaga aagttaactggatagatttaactggtcagaaatgtgtgaatgaaccag taaaataccaaccagaattgtatataacaaatactgtcaaagacccag atgaagatggatatctccatattacatcagtaatggtgggagttatg tagatggttgtgtcctgtgggaattgccagtttatacagatgaagtaa -continued gctataagtttagcgaatatataaacgttggggagactgaggctatat ttgatggaacagttacacaacctatcaagaattaggacttgtgcacac ctgtatactttgagctctcgtataatcacgagagcttttaaatatgt aagtcttaattatctcttgacaaaaagaacgtttattcgtataaggtt accaagagatgaagaaactattttatttacaattccccttgacaccaa aaactccatatgatatagtaaataaggttattaaacaagaaagaagaa gcaaccgcttctcgcctcgttaacacgaacgttttcaggcaaaaaat tcaaactttcgtcgcgtagcttacgcgattttgaatgtgcgggattgc tgaaaagcagcccgttttttttatggcctccgaacgaatgagttagcag gccgcagatttgaacagctattttctatcttgttgtaacaaaattaag tggaggtggctcaccattagcaaagacatgttggtaaacgatgggatt cgtgcacgtgaagtaagattgatcgaccaagacggtgaacaattaggc gtgaagagtaaaatcgatgcgcttcaaattgctgaaaaggctaatctt gatctagtgcttgttgctccaacagcgaaaccgccagtagctcgta.

(SEQ ID NO: 38)

<u>GAATTC</u>atggcgcgggatggtatactatacaagcgtatggttcaaaaa gatactttgaattaagaagtacaataaagttaacttcattagacaaaa agaaaaaacaaggaagaatagtacatagttatatacttggagagtg aggtgtaatatgggggcagctgattttttgggttcatatatgtagtt tcaagattagccattgttgcggcagtagttacttcttatacttattg agaaaaattgcaaataaatagaaaaaaagcctttgtcaaacgaggattt tttatgcaaaaaatacgacgaatgaagccatgtgagacaatttggaat agcagacaacaaggaaggtagaacatgttttgaaaaatttactgattt tcgattattattaacgcttgttaatttaaacatctcttattttgcta acatataagtatacaaagggacataaaaaggttaacagcgtttgttaa ataggaagtatatgaaaatcctcttttgtgtttctaaatttattttta aggagtggaga<u>GGATCC</u>ggacttgtgcacacctgtatactttgagctc tcgtataatcacgagagcttttaaatatgtaagtcttaattatctct tgacaaaagaacgtttattcgtataaggttaccaagagatgaagaaa ctattttatttacaattccccttgacaccaaaaactccatatgatata gtaaataaggttattaaacaagaaagaagaagcaacccgcttctcgcc tcgttaacacgaacgttttcaggcaaaaaattcaaactttcgtcgcgt agcttacgcgattttgaatgtgcgggattgctgaaaagcagcccgttt ttttatggcctccgaacgaatgagttagcaggccgcagatttgaacag ctattttctatcttgttgtaacaaaattaagtggaggtggctcaccat tagcaaagacatgttggtaaacgatgggattcgtgcacgtgaagtaag attgatcgaccaagacggtgaacaattaggcgtgaagagtaaaatcga tgcgcttcaaattgctgaaaaggctaatcttgatctagtgcttgttgc tccaacagcgaaaccgccagtagctcgta<u>CTGCAG</u>.

The inl C gene codes for 296 amino acid protein and the entire gene for this protein is deleted. The DNA fragments, DNA-up and DNA-down are amplified by PCR and cloned sequentially in the plasmid, pNEB193 using restriction enzyme sites EcoRI/BamHI and BamH1/Pst1, respectively as indicated in FIG. 3. The DNA cassette up-down (EcoR1 and Pst1 fragment) is excised and further cloned in the temperature sensitive shuttle vector, pKSV7. After cloning, the plasmid, pKSV7/up-down is transformed in the strain Lm dal dat actA and the resulting colonies are tested for the presence of plasmid using colony PCR.

For homologous recombination, the bacteria is cultured repeatedly for 5 days under chloramphenicol (Cm) selection at 30° C., conditions permissive for plasmid replication and during which time random DNA crossover events occur. This incubation step allowed for the integration of the shuttle plasmid into the genome, thus initially transferring Cm resistance. Bacteria containing a chromosomally integrated plasmid copy are selected by growth under Cm selective pressure during a temperature shift to 42° C., conditions not permissive for plasmid replication. The colonies are verified for the first recombination using PCR and the growth temperature are again shifted to 30° C. to allow for a second DNA cross over occurring at homologous sites, thus excising unwanted plasmid sequences and leaving only the recombinant gene copy behind in the Lm chromosome. By employing an additional temperature shift to 42° C., the excised plasmid is prohibited from replicating, so that it is diluted out during expansion of the bacterial culture. Furthermore, subsequent replica plating is used for selecting the Cm sensitive bacteria. The Cm sensitive colonies are analyzed for the deletion of inl C gene using colony PCR.

Generation of an ActA Deletion Mutant

Figure 4:
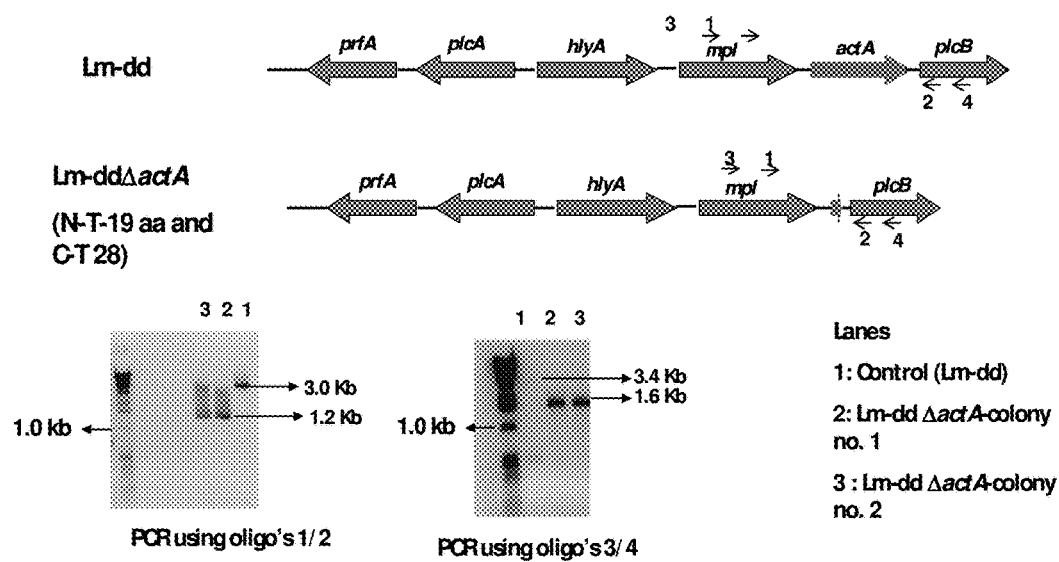
FIG. 4 shows a Schematic representation of the Lm-dd and Lm-ddD actA strains. The gel showing the size of PCR products using oligo's ½ and oligo's ¾ obtained using e chromosomal DNA of the strains, Lm-dd and Lm-ddΔactA as template.

The strain Lm dal dat (Lmdd) was attenuated by the irreversible deletion of the virulence factor, ActA. An in frame deletion of actA in the Lmdaldat (Lmdd) background was constructed to avoid any polar effects on the expression of downstream genes. The Lm dal dat ΔactA contains the first 19 amino acids at the N-terminal and 28 amino acid residues of the C-terminal with a deletion of 591 amino acids of ActA. The deletion of the gene into the chromosomal spot was verified using primers that anneal external to the actA deletion region. These are primers 3 (Adv 305-tgggatggc-caagaaattc) (SEQ ID NO: 39) and 4 (Adv304-ctaccatgtcttc-cgttgcttg) (SEQ ID NO: 40) as shown in the FIG. 4. The PCR analysis was performed on the chromosomal DNA isolated from Lmdd and Lm-ddΔactA. The sizes of the DNA fragments after amplification with two different set of primer pairs 1, 2 and 3, 4 in Lm-dd chromosomal DNA was expected to be 3.0 Kb and 3.4 Kb. However, for the Lm-ddΔactA the expected sizes of PCR using the primer pairs 1, 2 and 3, 4 was 1.2 Kb and 1.6 Kb. Thus, PCR analysis in FIG. 3 confirms that 1.8 kb region of actA was deleted in the strain, Lm-ddΔactA. DNA sequencing was also performed on PCR products to confirm the deletion of actA containing region in the strain, Lm-ddΔactA (FIG. 5).

(SEQ ID NO: 41)

gcgccaaatcattggttgattggtgaggatgtctgtgtgcgtgggtcg cgagatgggcgaataagaagcattaaagatcctgacaaatataatcaa gcggctcatatgaaagattacgaatcgcttccactcacagaggaaggc gactggggcggagttcattataatagtggtatcccgaataaagcagcc tataatactatcactaaacttggaaaagaaaaaacagaacagctttat tttcgcgccttaaagtactatttaacgaaaaaatcccagtttaccgat -continued
gcgaaaaaagcgcttcaacaagcagcgaaagatttatatggtgaagat gcttctaaaaaagttgctgaagcttgggaagcagttggggttaactga ttaacaaatgttagagaaaaattaattctccaagtgatattcttaaaa taattcatgaatattttttcttatattagctaattaagaagataacta actgctaatccaattttaacggaacaaattagtgaaaatgaaggccg aattttccttgttctaaaaaggttgtattagcgtatcacgaggaggga gtataag*tgggattaaacagatttatgcgtgcgatgatggtggttttc*

*attactgccaattgcattacgattaacccgac* gtcgac*ccatacgac*

*gttaattcttgcaatgttagctattggcgtgttctctttagggcgtt*

*tatcaaaattattcaattaagaaaaaataattaaaaacacagaacgaa*

*agaaaaagtgaggtgaatgatatgaaattcaaaaaggtggttctaggt*

*atgtgcttgatcgcaagtgttctagtctttccggtaacgataaaagca*

*aatgcctgttgtgatgaatacttacaaacacccgcagctccgcatgat*

*attgacagcaaattaccacataaacttagttggtccgcggataacccg*

*acaaatactgacgtaaatacgcactattggcttttttaaacaagcggaa*

*aaaatactagctaaagatgtaaatcatatgcgagctaatttaatgaat*

*gaacttaaaaaattcgataaacaaatagctcaaggaatatatgatgcg*

*gatcataaaaatccatattatgatactagtacatttttatctcattttt*

*tataatcctgatagagataatacttatttgccgggttttgctaatgcg*

*aaaataacaggagcaaagtatttcaatcaatcggtgactgattaccga*

*gaagggaa.*

Production of Inflammatory Cytokines:

Macrophages such as RAW 264.7 are infected with different *Listeria* backbones such as Lm dal dat, Lm dal dat actA, Lm dal dat actA α inlC and Lm dal dat A inlC and supernatant is harvested at different time points to quantify the level of various cytokines using different ELISA based kits. The cytokines that are quantified include IFN-γ, TNF-α and IL-6.

In Vivo Cytokine Production:

To measure the in vivo cytokine production and recruitment of neutrophils, C57BL/6 mice are injected intraperitoneally with different $10^8$ CFU of inlC mutant, *Listeria* control or an equivalent volume of saline. After 12 h mice are killed and peritoneal cavities are washed with 2 mL of PBS. The peritoneal washes are examined for bacterial load after plating on growth medium and analysis of proinflammatory cytokines such as MIP-1α, KC, MCP etc. Using flow cytometry the number of neutrophils and macrophages is determine after staining with markers such as Gr-1, CD11b and F4/80 and further these populations are quantified using CellQuest software.

Transwell Migration Assay:

This assay is done to determine if there is an increase in the migration of neutrophils following infection of bone marrow derived macrophages or dendritic cells with the inlC deletion strain. Bone marrow-derived macrophages or dendritic cells are isolated from mice such as C57BL/6 and are infected with the inlC deletion mutants or control *Listeria*. Using infected cells the transwell assay is set up using corning costar Transwell plates. The assay is initially standardize using 3, 5, or 8 micron pore transwell plates. To test neutrophil migration, plate the infected APCs in the bottom of the plate and the neutrophils in the top of the well in the chamber. At different time points the cells are counted to determine the number of neutrophils that have migrated to the bottom.

Therapeutic Efficacy of the Lm dal dat actA Δ inlC Mutant:

To determine the therapeutic efficacy of inlC mutant, human Prostate specific antigen (PSA) is used as tumor antigen as proof of concept. The backbone Lm dal dat actA inlC are transformed with the plasmid, pAdv142 that contains expression cassette for human PSA resulting in LmddAinlC142. The strain LmddAinlC142 is characterized for the expression and secretion of fusion protein, tLLO-PSA. Further the strain LmddAinlC142 are passaged twice in vivo in mice and the colonies obtained after two in vivo passages are examined for the expression and secretion of fusion protein, tLLO-PSA. The vaccine working stock are prepared from the colonies obtained after second in vivo passage and this are used for the assessment of therapeutic effects and immunogenicity.

Impact on Tumor Microenvironment:

The ability of LmddAinlC142, LmddA142 and other control strains to cause infiltration of immune cells in the tumor microenvironment are determined. In this study mice are inoculated with $1\times10^6$ TPSA23 tumor cells on day 0 and are vaccinated on day 7, 14 and 21 with $10^8$ CFU of LmddAinlC142, LmddA142 and other control strains. Tumors are harvested on day 28 and processed for further staining with different cell surface markers such as Gr-1, CD11b, CD3, CD4, CD8, CD25, Foxp3, NK1.1 and CD62L. Using these markers different cell populations that are examined include macrophages ($CD11b^+$), NK cells ($NK1.1^+$), neutrophils ($Gr-1^+$ $CD11b^+$), myeloid derived suppressor cells (MDSCs) ($Gr-1^+$ $CD11b^+$), regulatory T cells ($CD4^+$ $CD25^+$ $Foxp3^+$) and effector T cells ($CD8^+$ $CD3^+$ $CD62L^{low}$). Further effector T cells are characterized for their functional ability to produce effector cytokines such as IFN-γ, TNF-α and IL-2. The intratumoral regulatory T cells and MDSCs are tested for their ability to cause suppression of T cell proliferation.

*Listeria* Immunization and *S. mansoni* Infection

Female (6-8 weeks old) BALB/c mice were maintained as naïve (un-infected) or infected with *S. mansoni*. For infection, mice were injected i.p. with 50 cercariae. Eight weeks later, both infected and un-infected mice were immunized i.p. (100 μg/injection) with 0.1 LD50 Lm-gag, 0.2 LD50 Lm-gag, or 1 LD50 Lm-gag, or orally with 10 LD50 Lm-gag or 100 LD50 Lm-gag. Two weeks later, some groups of mice were boosted i.p. with 0.1 LD50 Lm-gag or 0.2 LD50 Lm-gag or orally with 10 LD50 Lm-gag or 100 LD50 Lm-gag in a similar manner. Lm-E7 was used as a negative control. Two weeks after the final immunization, the T-cell immune response was analyzed as described below. Infection was confirmed at the time of sacrifice by examining the mice for the presence of worms, liver eggs and hep ato splenomeg ally.

MDSC and Treg Function

Tumors were implanted in mice on the flank or a physiological site depending on the tumor model. After 7 days, mice were then vaccinated, the initial vaccination day depends on the tumor model being used. The mice were then administered a booster vaccine one week after the vaccine was given.

Mice were then sacrificed and tumors and spleen were harvested 1 week after the boost or, in the case of an aggressive tumor model, 3-4 days after the boost. Five days before harvesting the tumor, non-tumor bearing mice were vaccinated to use for responder T cells. Splenocytes were prepared using standard methodology.

Briefly, single cell suspensions of both the tumors and the spleens were prepared. Spleens were crushed manually and red blood cells were lysed. Tumors were minced and incubated with collagenase/DNase. Alternatively, the GENTLEMACS™ dissociator was used with the tumor dissociation kit.

MDSCs were purified from tumors and spleens using a Miltenyi kit and columns or the autoMACs separator. Cells were then counted.

Single cell suspension was prepared and the red blood cells were lysed. Responder T cells were then labeled with CFSE.

Cells were plated together at a 2:1 ratio of responder T cells (from all division cycle stages) to MDSCs at a density of $1\times10^5$ T cells per well in 96 well plates. Responder T cells were then stimulated with either the appropriate peptide (PSA OR CA9) or non-specifically with PMA/ionomycin. Cells were incubated in the dark for 2 days at 37° C. with 5% $CO_2$. Two days later, the cells were stained for FACS and analyzed on a FACS machine.

Analysis of T-Cell Responses

For cytokine analysis by ELISA, splenocytes were harvested and plated at 1.5 million cells per well in 48-well plates in the presence of media, SEA or conA (as a positive control). After incubation for 72 hours, supernatants were harvested and analyzed for cytokine level by ELISA (BD). For antigen-specific IFN-γ ELISpot, splenocytes were harvested and plated at 300K and 150K cells per well in IFN-γ ELISpot plates in the presence of media, specific CTL peptide, irrelevant peptide, specific helper peptide or conA (as a positive control). After incubation for 20 hours, ELISpots (BD) were performed and spots counted by the Immunospot analyzer (C.T.L.). Number of spots per million splenocytes were graphed.

Splenocytes were counted using a Coulter Counter, Z1. The frequency of IFN-γ producing CD8+ T cells after re-stimulation with gag-CTL, gag-helper, medium, an irrelevant antigen, and con A (positive control) was determined using a standard IFN-γ-based ELISPOT assay.

Briefly, IFN-γ was detected using the mAb R46-A2 at 5 mg/ml and polyclonal rabbit anti-IFN-γ used at an optimal dilution (kindly provided by Dr. Phillip Scott, University of Pennsylvania, Philadelphia, Pa.). The levels of IFN-γ were calculated by comparison with a standard curve using murine rIFN-γ (Life Technologies, Gaithersburg, Md.). Plates were developed using a peroxidase-conjugated goat anti-rabbit IgG Ab (IFN-γ). Plates were then read at 405 nm. The lower limit of detection for the assays was 30 pg/ml.

Results

Figure 1B:
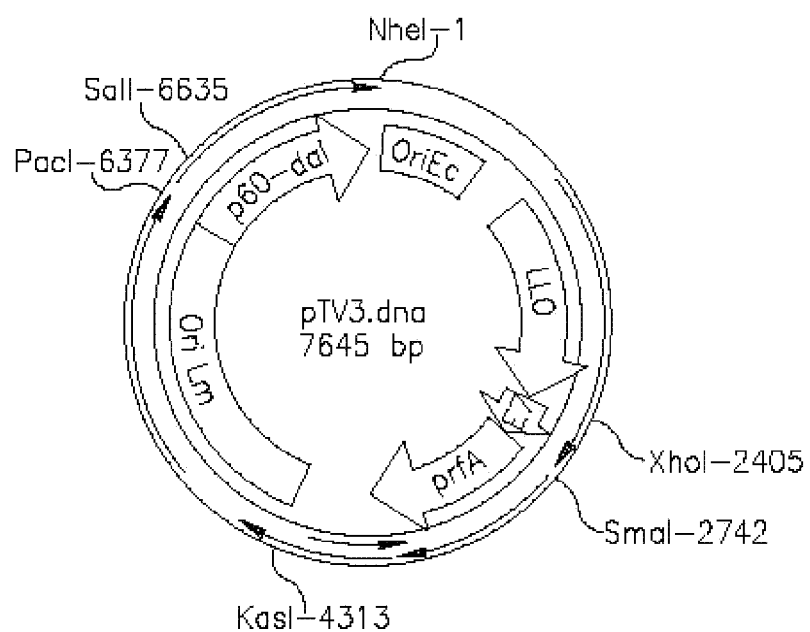

Example 1: A Plasmid Containing an Amino Acid Metabolism Enzyme Instead of an Antibiotic Resistance Gene is Retained in E. Coli and Lm Both In Vitro and In Vivo An auxotroph complementation system based on D-alanine racemase was utilized to mediate plasmid retention in Lm without the use of an antibiotic resistance gene. E. coli strain MB2159 is an alr (−)/dadX (−) deficient mutant that is not able to synthesize D-alanine racemase. Listeria strain Lm dal(−)/dat(−) (Lmdd) similarly is not able to synthesize D-alanine racemase due to partial deletions of the dal and the dat genes. Plasmid pGG55, which is based on E. coli-Listeria shuttle vector pAM401, was modified by removing both CAT genes and replacing them with a p60-dal expression cassette under control of the Listeria p60 promoter to generate pTV3 (FIG. 1). DNA was purified from several colonies.

Example 2: Plasmids Containing a Metabolic Enzyme do not Increase the Virulence of Bacteria As virulence is linked to LLO function, the hemolytic lysis activity between Lmdd-TV3 and Lm-LLOE7 was compared. This assay tests LLO function by lysis of red blood cells and can be performed with culture supernatant, purified LLO or bacterial cells. Lmdd-TV3 displayed higher hemolytic lysis activity than Lm-LLOE7.

In vivo virulence was also measured by determining $LD_{50}$ values, a more direct, and therefore accurate, means of measuring virulence. The $LD_{50}$ of Lmdd-TV3 ($0.75\times10^9$) was very close to that of Lm-LLOE7 ($1\times10^9$), showing that plasmids containing a metabolic enzyme do not increase the virulence of bacteria.

Figure 6:
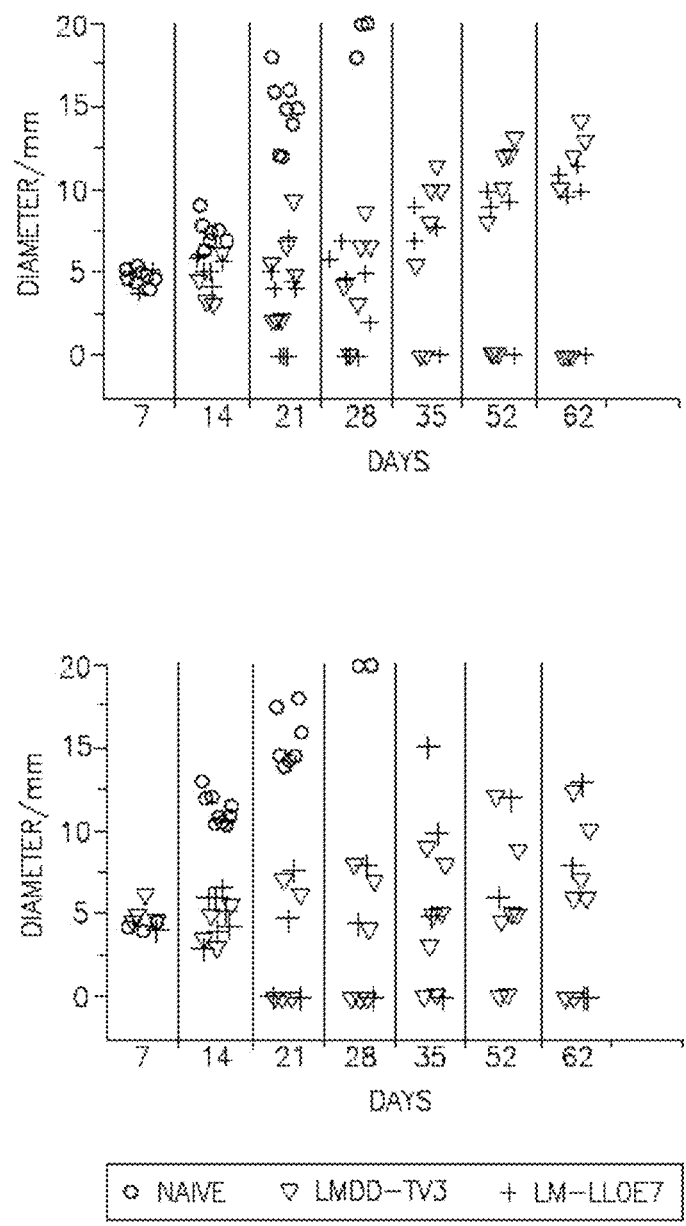
FIG. 6 depicts tumor regression in response to administration of Lm vaccine strains (A). Circles represent naive mice, inverted triangles represent mice administered Lmdd-TV3, and crosses represent mice administered Lm-LLOE7.

Example 3: Induction of Anti-Tumor Immunity by Plasmids Containing a Metabolic Enzyme Efficacy of the metabolic enzyme-containing plasmid as a cancer vaccine was determined in a tumor regression model. The TC-1 cell line model, which is well characterized for HPV vaccine development and which allowed for a controlled comparison of the regression of established tumors of similar size after immunization with Lmdd-TV3 or Lm-LLOE7, was used. In two separate experiments, immunization of mice with Lmdd-TV3 and Lm-LLOE7 resulted in similar tumor regression (FIG. 6) with no statistically significant difference (p<0.05) between vaccinated groups. All immunized mice were still alive after 63 days, whereas non-immunized mice had to be sacrificed when their tumors reached 20 mm diameter. Cured mice remained tumor-free until the termination of the experiment.

Thus, metabolic enzyme-containing plasmids are efficacious as a therapeutic cancer vaccine. Because immune responses required for a therapeutic cancer vaccine are stronger than those required for a prophylactic cancer vaccine, these results demonstrate utility as well for a prophylactic cancer vaccine.

Example 4: inlC-Deletion Mutant Generate Significantly High Levels of the Chemokines and Cytokines inlC deletion mutant generates significantly high levels of the chemokines such as MIP-1α, KC (mouse homolog of IL-8), MCP resulting in infiltration of neutrophils and leukocytes towards the site of infection. Thus when different Listeria strains are administered intraperitoneally, the inlC mutant demonstrate an increase production of these cytokines and chemokines, which attract neutrophils and macrophages in the peritoneal fluid obtained 12 h after injection. Further, inlC deletion mutant generate significantly high levels of the inflammatory cytokines when compared to control strains.

Example 5: inlC-Deletion Mutants Induce Neutrophil Migration

The macrophages infected with inlC deletion mutant show significant increase in the migration of neutrophils at different time points when compared to other control strains.

The results of this experiment strongly support the ability of this strain to attract immune cells such as neutrophils during infection.

Example 6: inlC-Deletion Mutants Effect a Therapeutic Anti-Tumor Response

The results of anti-tumor studies using both LmddA142 and LmddAinlC142 are very comparable to each other and therapeutic regression of tumors is observed. Further, two doses of LmddAinlC142 are comparable to three doses of the strain LmddA142 because of its ability to generate high levels of innate responses and increased secretion of proinflammatory cytokines.

Figure 7:
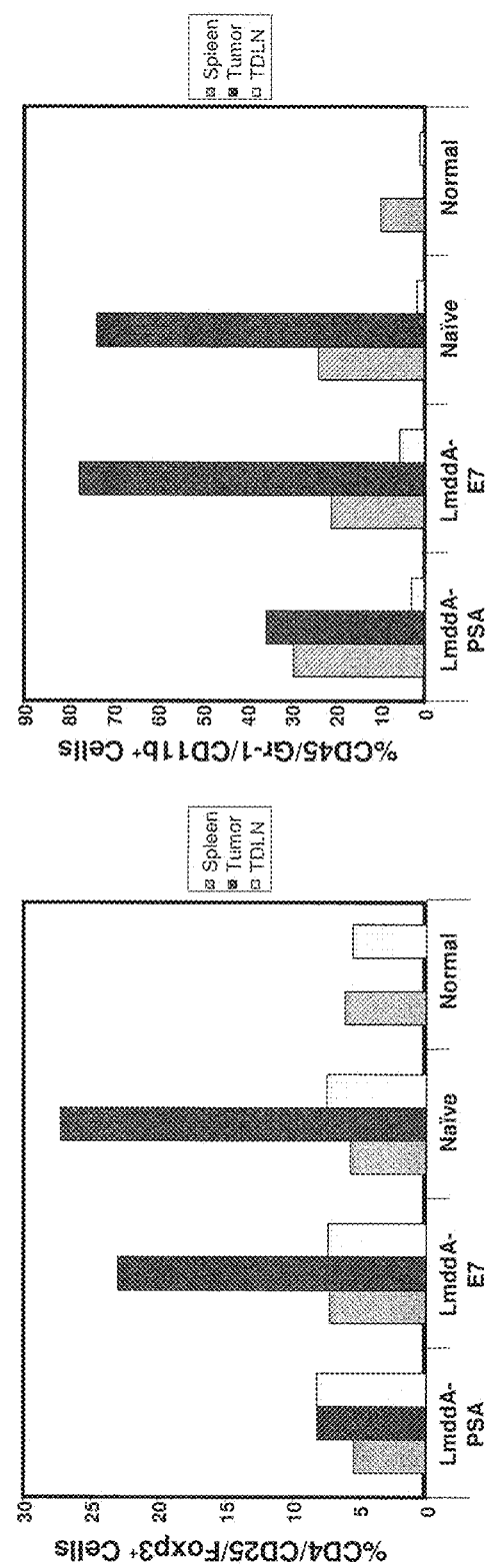
FIG. 7 shows a decrease in MDSCs and Tregs in tumors. The number of MDSCs (right-hand panel) and Tregs (left-hand panel) following Lm vaccination (LmddAPSA and LmddAE7).

At day 0 tumors were implanted in mice. At day 7 mice were vaccinated with Lmdda-E7 or LmddA-PSA. At day 14 tumors were harvested and MDSCs and Treg percentages and numbers were measured for vaccinated and naïve groups. It was found that there is a decrease in the percentages of both MDSC and Tregs in the tumors of Listeria-treated mice, whereas the same effect is not observed in the spleens or the draining lymph nodes (TLDN) (FIG. 7).

Isolated splenocytes and tumor-infiltrating lymphocytes (TILs) extracted from tumor bearing mice in the above experiment were pooled and stained for CD3, and CD8 to elucidate the effect of immunization with Lm-LLO-E7, Lm-LLO-PSA and Lm-LLO-CA9, Lm-LLO-Her2 (FIG. 8-20) on the presence of MDSCs and Tregs (both splenic and tumoral MDSCs and Tregs) in the tumor. Each column represents the % of T cell population at a particular cell division stage and is subgrouped under a particular treatment group (naïve, peptide-CA9 or PSA-treated, no MDSC/Treg, and no MDSC+PMA/ionomycin) (see FIGS. 8-20).

Analysis of Cells in the Blood of Tumor-Bearing Mice

Blood from tumor-bearing mice was analyzed for the percentages of Tregs and MDSCs present. There is a decrease in both MDSC and Tregs in the blood of mice after Lm vaccination.

Example 7: Suppressor Cell Function after Listeria Vaccine Treatment

At day 0 tumors were implanted in mice. At day 7 mice were vaccinated with Lmdda-E7 or LmddA-PSA. At day 14 tumors were harvested and MDSCs and Treg percentages and numbers were measured for vaccinated and naïve groups. It was found that there is a decrease in the percentages of both MDSC and Tregs in the tumors of Listeria-treated mice, whereas the same effect is not observed in the spleens or the draining lymph nodes (TLDN) (FIG. 7).

Isolated splenocytes and tumor-infiltrating lymphocytes (TILs) extracted from tumor bearing mice in the above experiment were pooled and stained for CD3, and CD8 to elucidate the effect of immunization with Lm-LLO-E7, Lm-LLO-PSA and Lm-LLO-CA9, Lm-LLO-Her2 (FIG. 8-20) on the presence of MDSCs and Tregs (both splenic and tumoral MDSCs and Tregs) in the tumor. Each column represents the % of T cell population at a particular cell division stage and is subgrouped under a particular treatment group (naïve, peptide-CA9 or PSA-treated, no MDSC/Treg, and no MDSC+PMA/ionomycin) (see FIGS. 8-20).

Analysis of Cells in the Blood of Tumor-Bearing Mice

Blood from tumor-bearing mice was analyzed for the percentages of Tregs and MDSCs present. There is a decrease in both MDSC and Tregs in the blood of mice after Lm vaccination.

Figure 10:
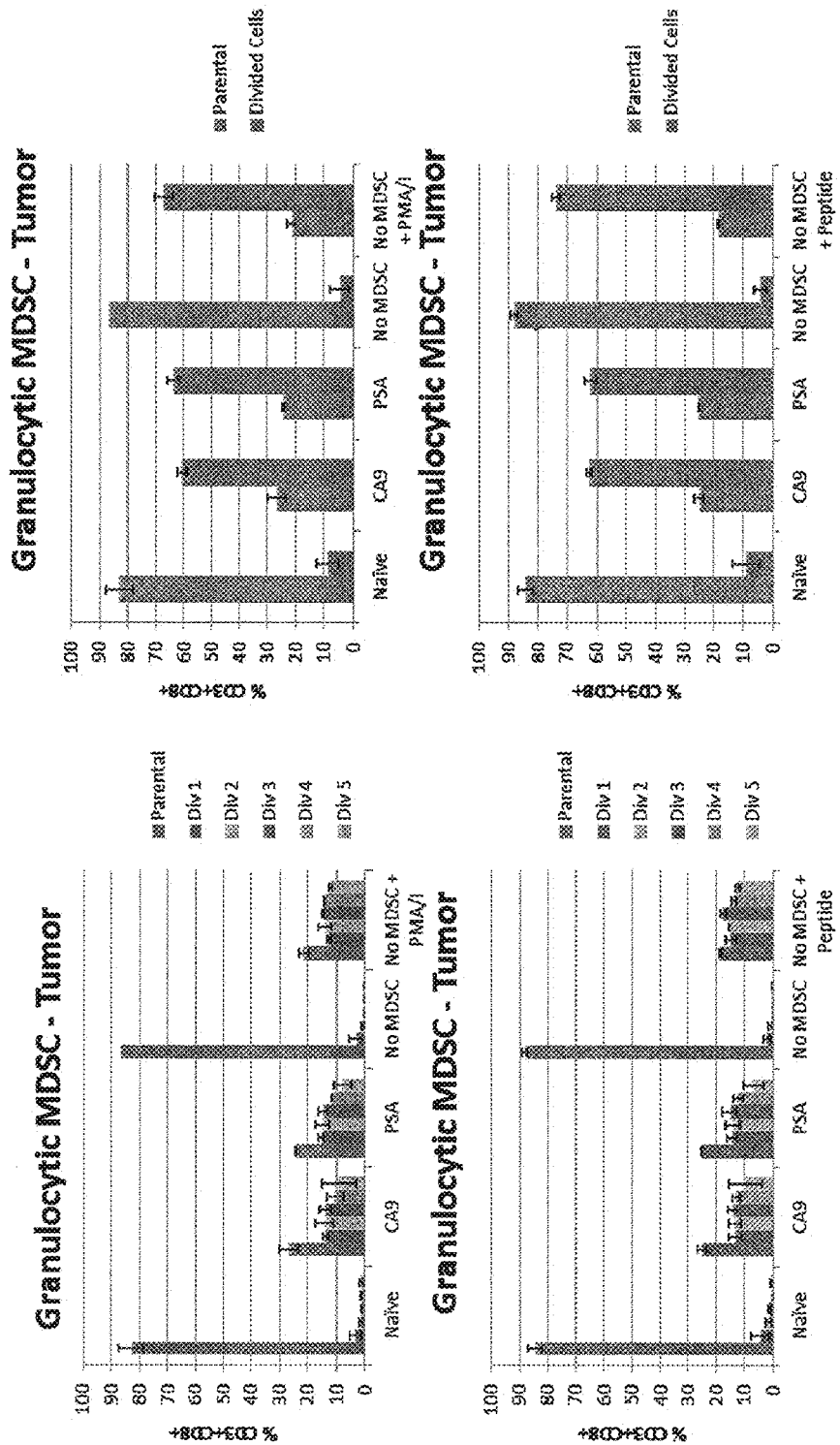
FIG. 10 shows suppressor assay data demonstrating that granulocytic MDSCs from tumors have a reduced ability to suppress T cells after *Listeria* vaccination. This change in the suppressive ability of the MDSCs is not antigen specific as the same decrease in suppression is seen with PSA-antigen specific T cells and also with non-specifically stimulated T cells. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.

Example 8: MDSCs from TPSA23 Tumors but not Spleens are Less Suppressive after Listeria Vaccination Suppressor assays were carried out using monocytic and granulocytic MDSCs isolated from TPSA23 tumors with non-specifically activated naïve murine cells, and specifically activated cells (PSA, CA9, PMA/ionomycyn). Results demonstrated that the MDSCs isolated from tumors from the Lm vaccinated groups have a diminished capacity to suppress the division of activated T cells as compared to MDSC from the tumors of naïve mice. (see Lm-LLO-PSA and Lm-LLO-treated Groups in FIGS. 8 & 10, right-hand panel in figures represents pooled cell division data from left-hand panel). In addition, T responder cells from untreated mice where no MDSCs were present and where the cells were unstimulated/activated, remained in their parental (resting) state (FIGS. 8 & 10), whereas T cells stimulated with PMA or ionomycin were observed to replicate (FIGS. 8 & 10). Further, it was observed that both, the Gr+Ly6G+ and the $Gr_{dim}$Ly6G-MDSCs are less suppressive after treatment with Listeria vaccines. This applies to their decreased abilities to suppress both the division of activated PSA-specific T cells and non-specific (PMA/Ionomycin stimulated) T cells.

Moreover, suppressor assays carried out using MDSCs isolated from TPSA23 tumors with non-specifically activated naïve murine cells demonstrated that the MDSCs isolated from tumors from the Lm vaccinated groups have a diminished capacity to suppress the division of activated T cells as compared to MDSC from the tumors of naïve mice (see FIGS. 8 & 10).

Figure 9:
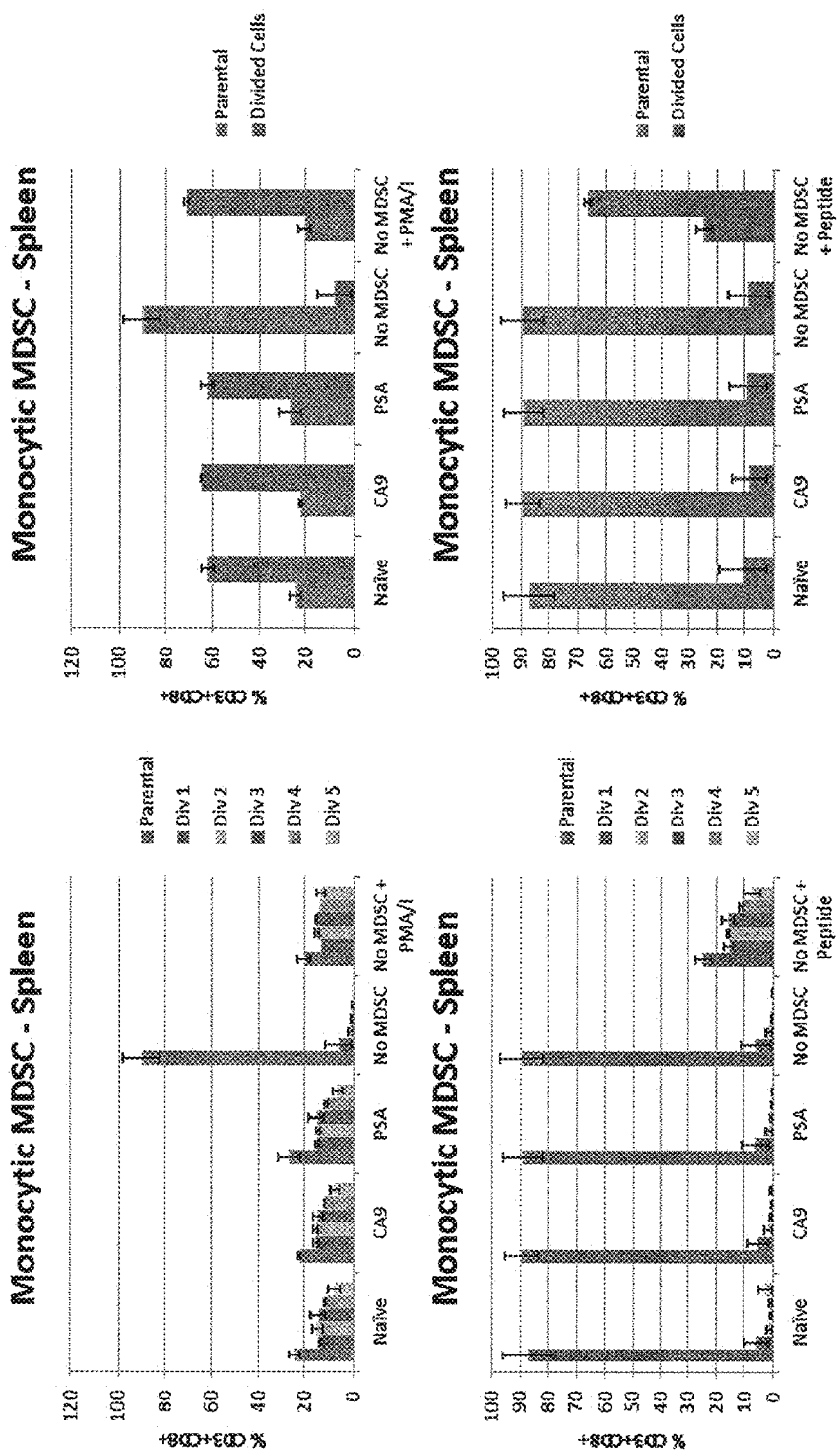
FIG. 9 shows suppressor assay data demonstrating that *Listeria* has no effect on splenic monocytic MDSCs and they are only suppressive in an antigen-specific manner. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.
Figure 11:
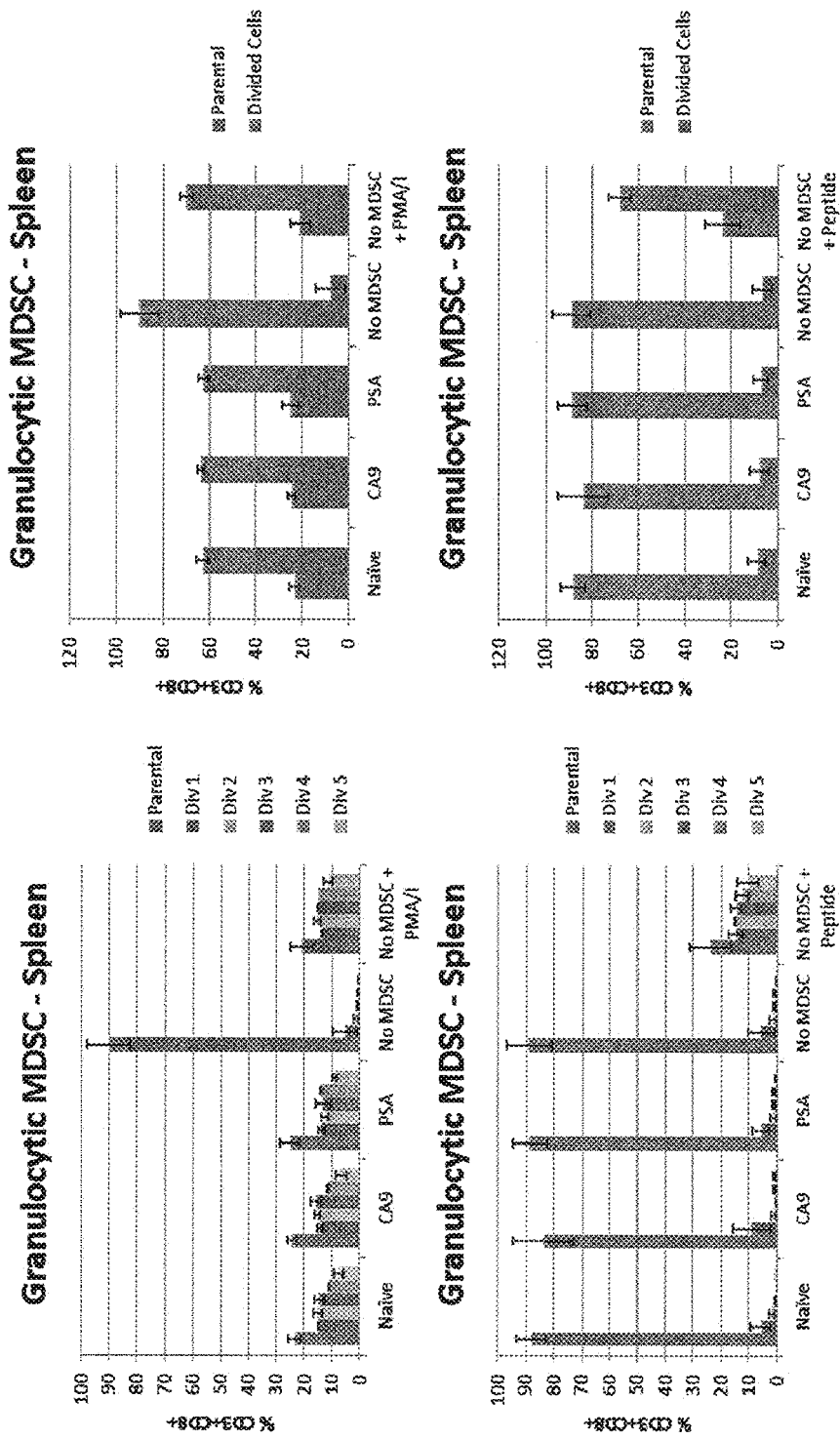
FIG. 11 shows suppressor assay data demonstrating that *Listeria* has no effect on splenic granulocytic MDSCs and they are only suppressive in an antigen-specific manner. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.
Figure 12:
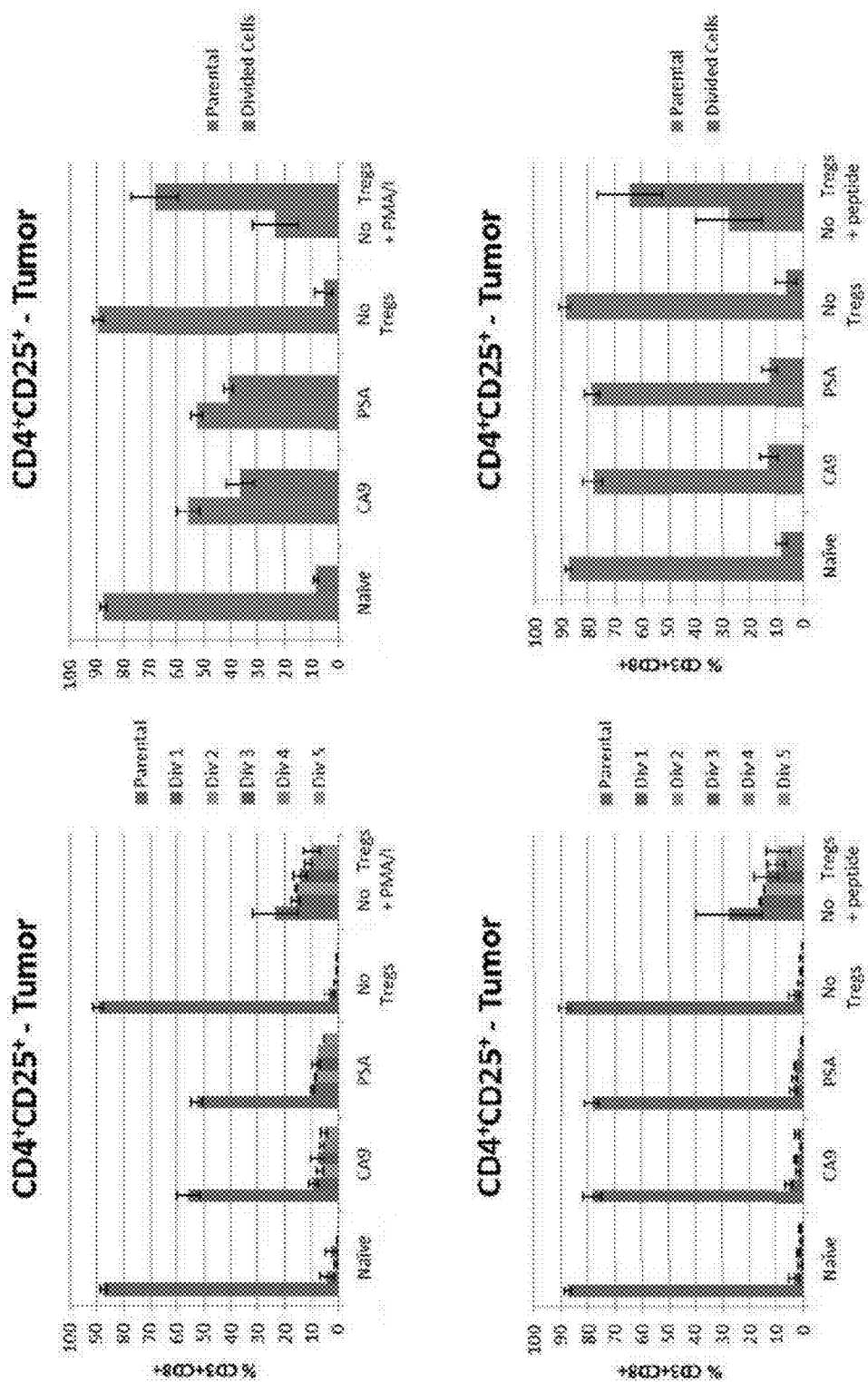
FIG. 12 shows suppressor assay data demonstrating that Tregs from tumors are still suppressive. There is a slight decrease in the suppressive ability of Tregs in a non-antigen specific manner, in this tumor model. The No Treg group shows the lack of division of the responder T cells when they are left unstimulated and the last group shows the division of stimulated cells with no Tregs added to suppress division. Left-hand panels show individual cell division cycles for each group. Right-hand panels show pooled division cycles.

In addition, the observations discussed immediately above relating to FIGS. 8 and 10 were not observed when using splenic MDSCs. In the latter, splenocytes/T cells from the naïve group, the Listeria-treated group (PSA, CA9), and the PMA/ionomycin stimulated group (positive control) all demonstrated the same level of replication (FIGS. 9 & 11). Hence, these results show that Listeria-mediated inhibition of suppressor cells in tumors worked in an antigen-specific and non-specific manner, whereas Listeria has no effect on splenic granulocytic MDSCs as they are only suppressive in an antigen-specific manner.

Figure 13:
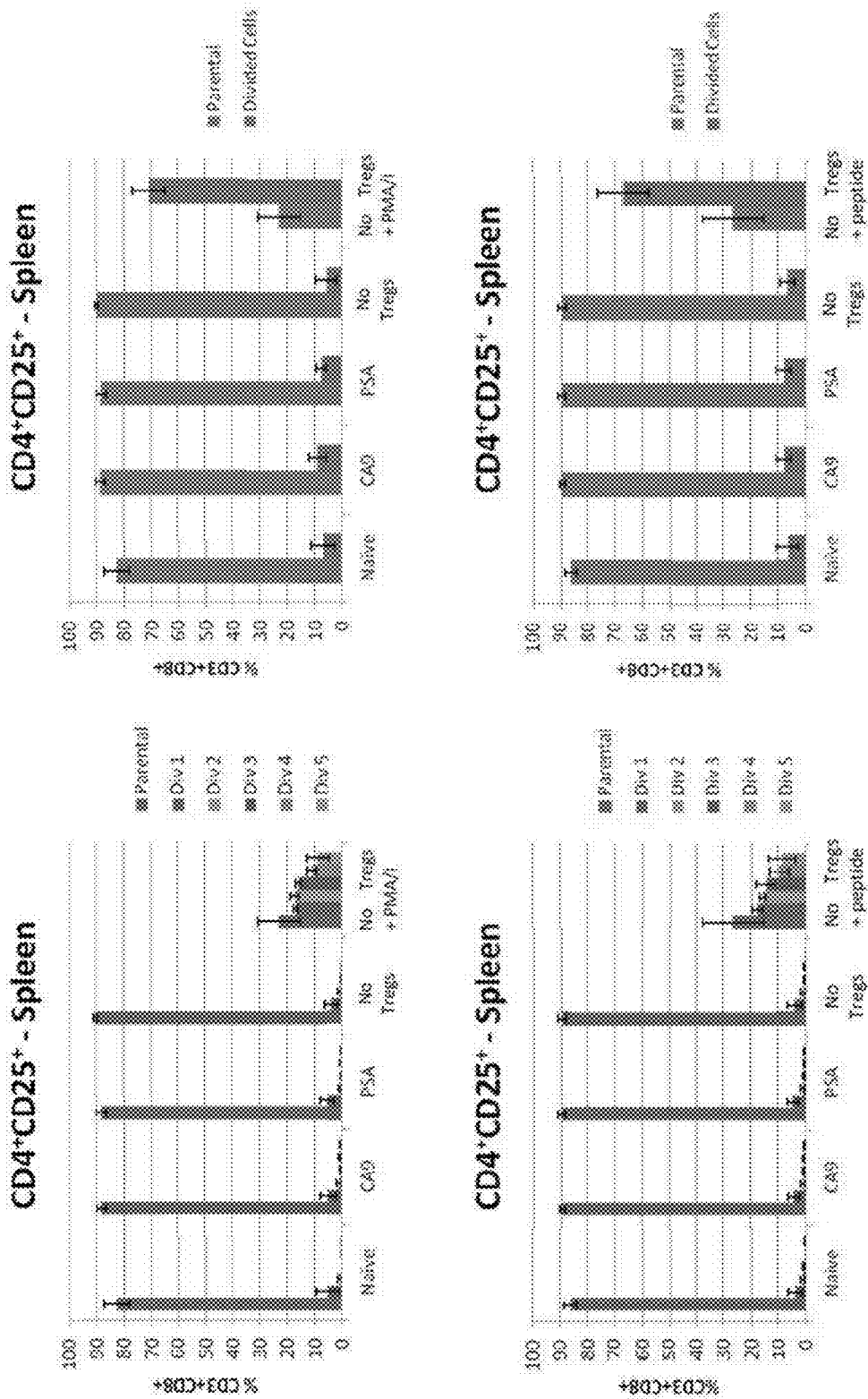
FIG. 13 shows suppressor assay data demonstrating that splenic Tregs are still suppressive. The No Treg group shows the lack of division of the responder T cells when they are left unstimulated and the last group shows the division of stimulated cells with no Tregs added to suppress division. Left-hand panels show individual cell division cycles for each group. Right-hand panels show pooled division cycles.

Example 9: Tumor T Regulatory Cells' Reduced Suppression but not Those from Spleens Suppressor assays were carried out using Tregs isolated from TPSA23 tumors after Listeria treatment. It was observed that after treatment with Listeria there is a reduction of the suppressive ability of Tregs from tumors (FIG. 12), however, it was found that splenic Tregs are still suppressive (FIG. 13).

Figure 14:
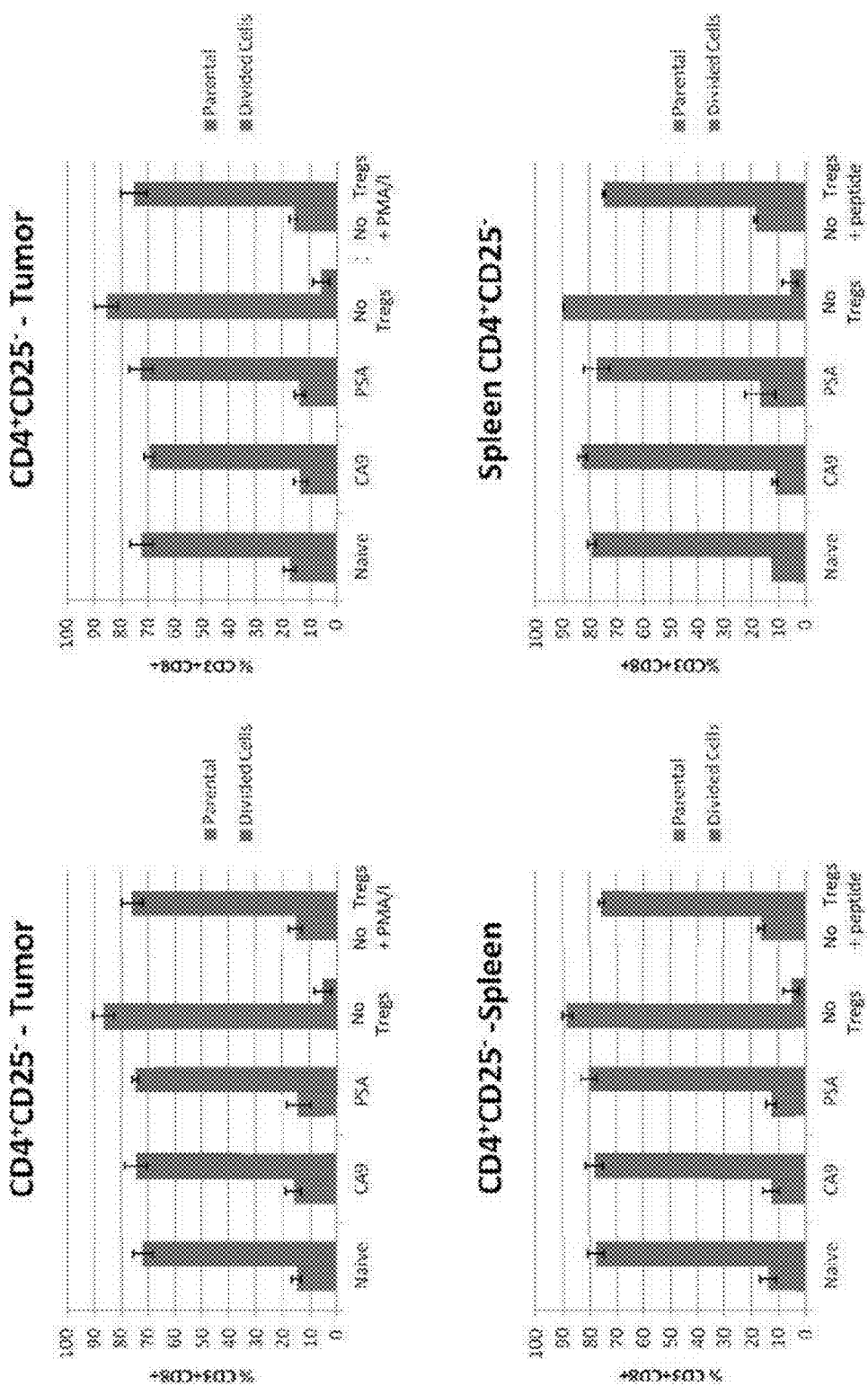
FIG. 14 shows suppressor assay data demonstrating that conventional CD4+ T cells have no effect on cell division regardless if whether they are found in the tumors or spleens of mice. Left-hand and Right-hand panels show pooled division cycles.
Figure 15:
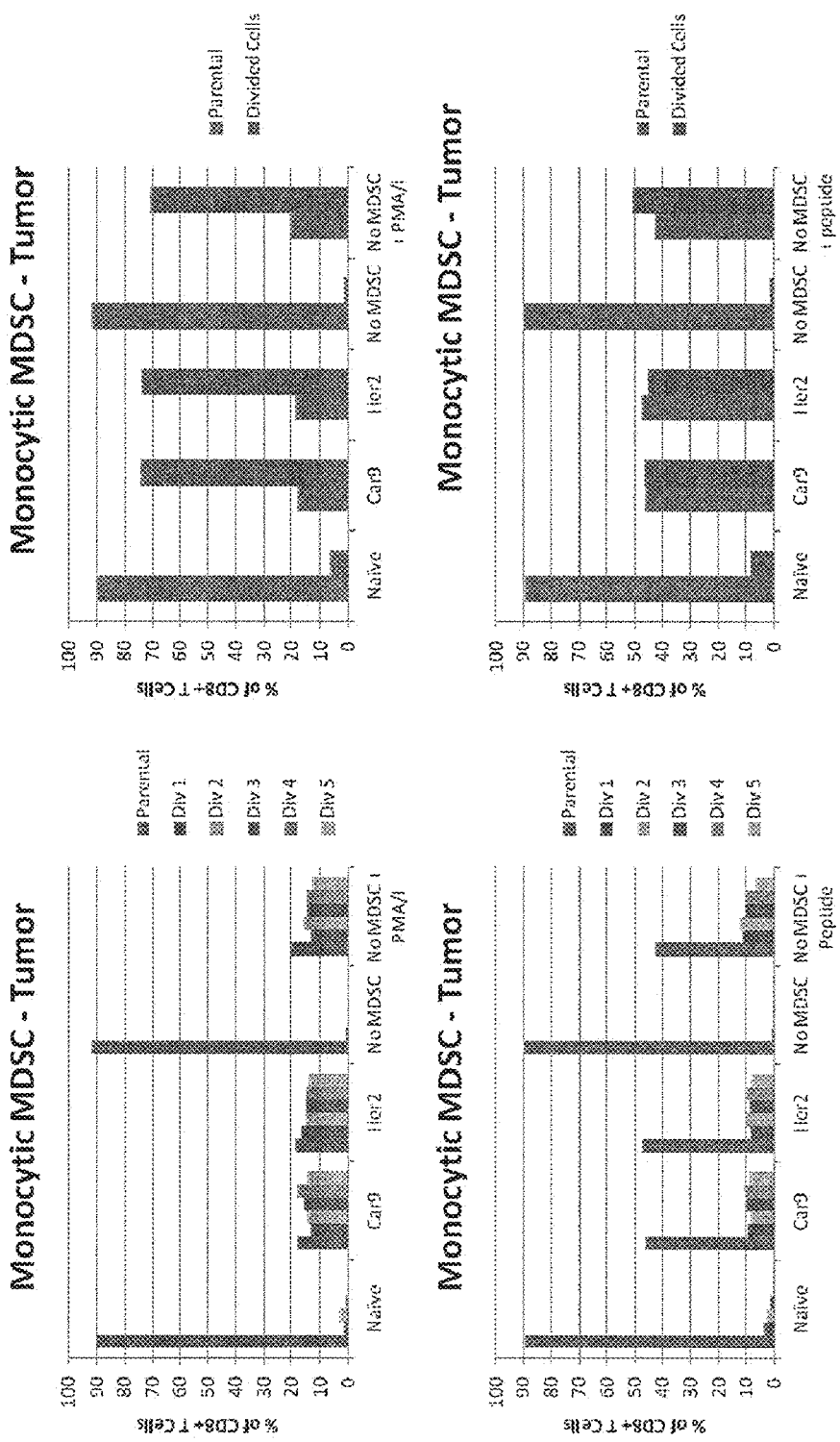
FIG. 15 shows suppressor assay data demonstrating that monocytic MDSCs from 4T1 tumors have decreased suppressive ability after *Listeria* vaccination. This change in the suppressive ability of the MDSCs is not antigen specific as the same decrease in suppression is seen with Her2/neu-antigen specific T cells and also with non-specifically stimulated T cells. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.
Figure 16:
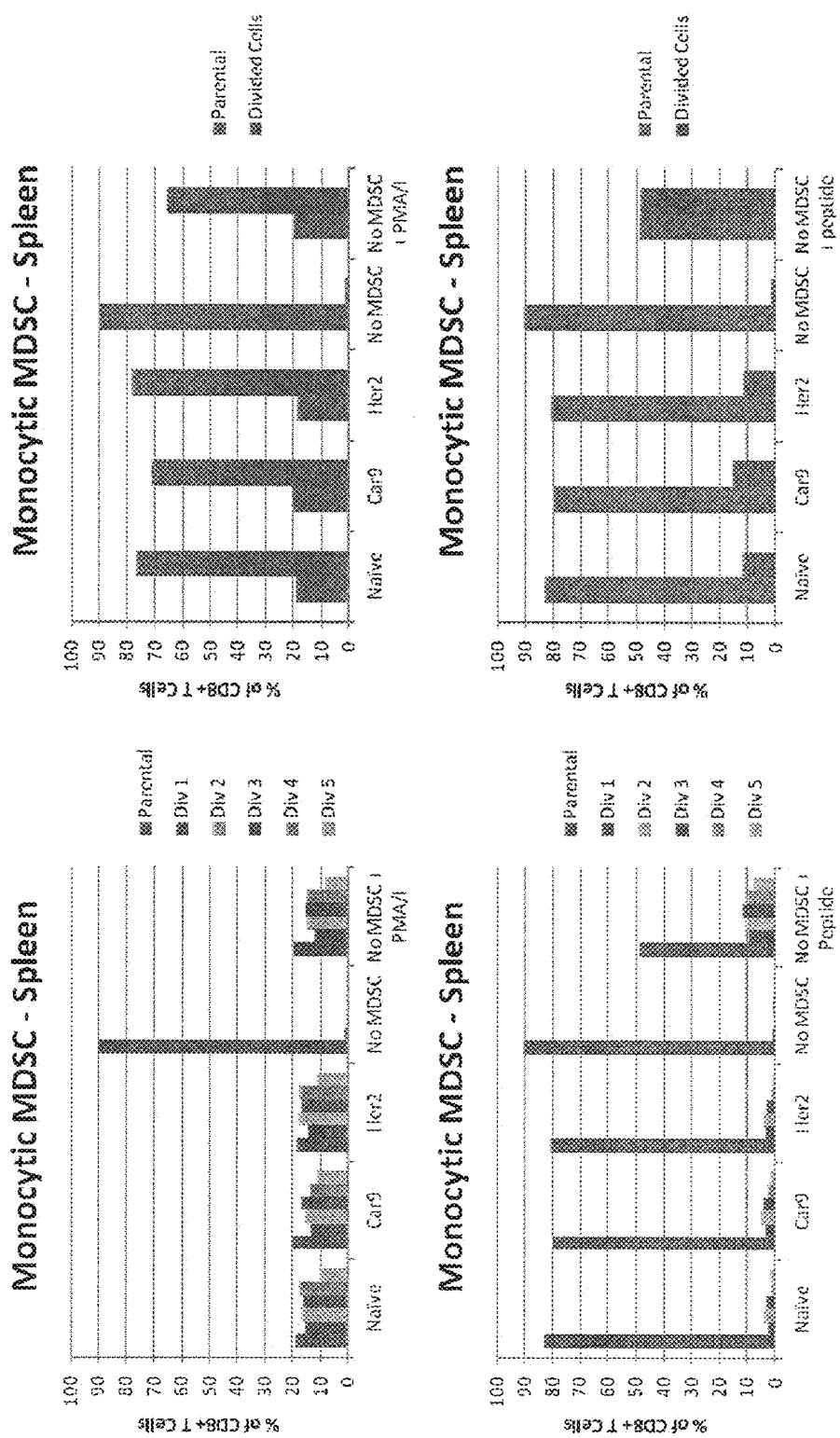
FIG. 16 shows suppressor assay data demonstrating that there is no *Listeria*-specific effect on splenic monocytic MDSCs. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.
Figure 17:
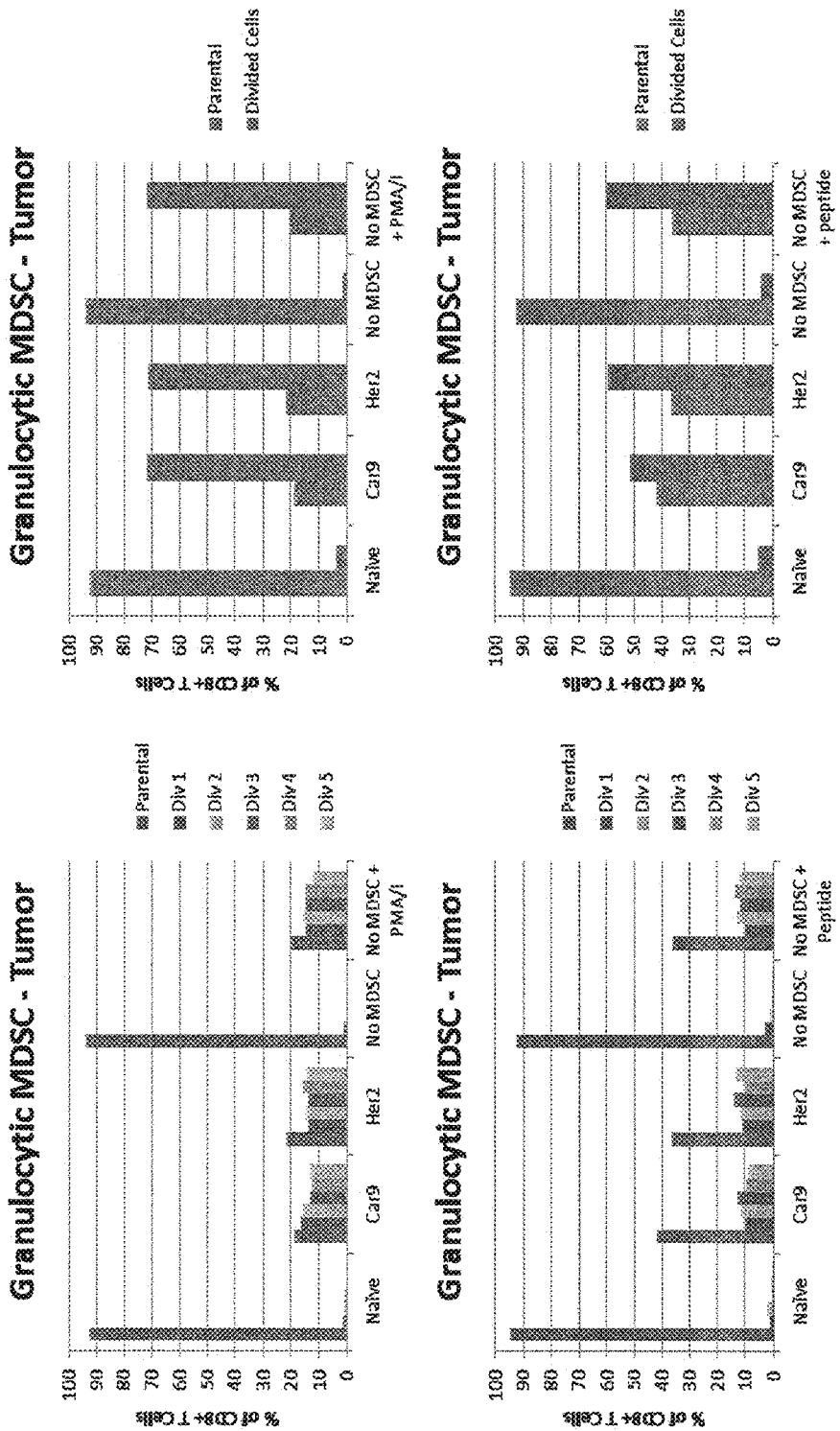
FIG. 17 shows suppressor assay data demonstrating that granulocytic MDSCs from 4T1 tumors have decreased suppressive ability after *Listeria* vaccination. This change in the suppressive ability of the MDSCs is not antigen specific as the same decrease in suppression is seen with Her2/neu-antigen specific T cells and also with non-specifically stimulated T cells. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.
Figure 18:
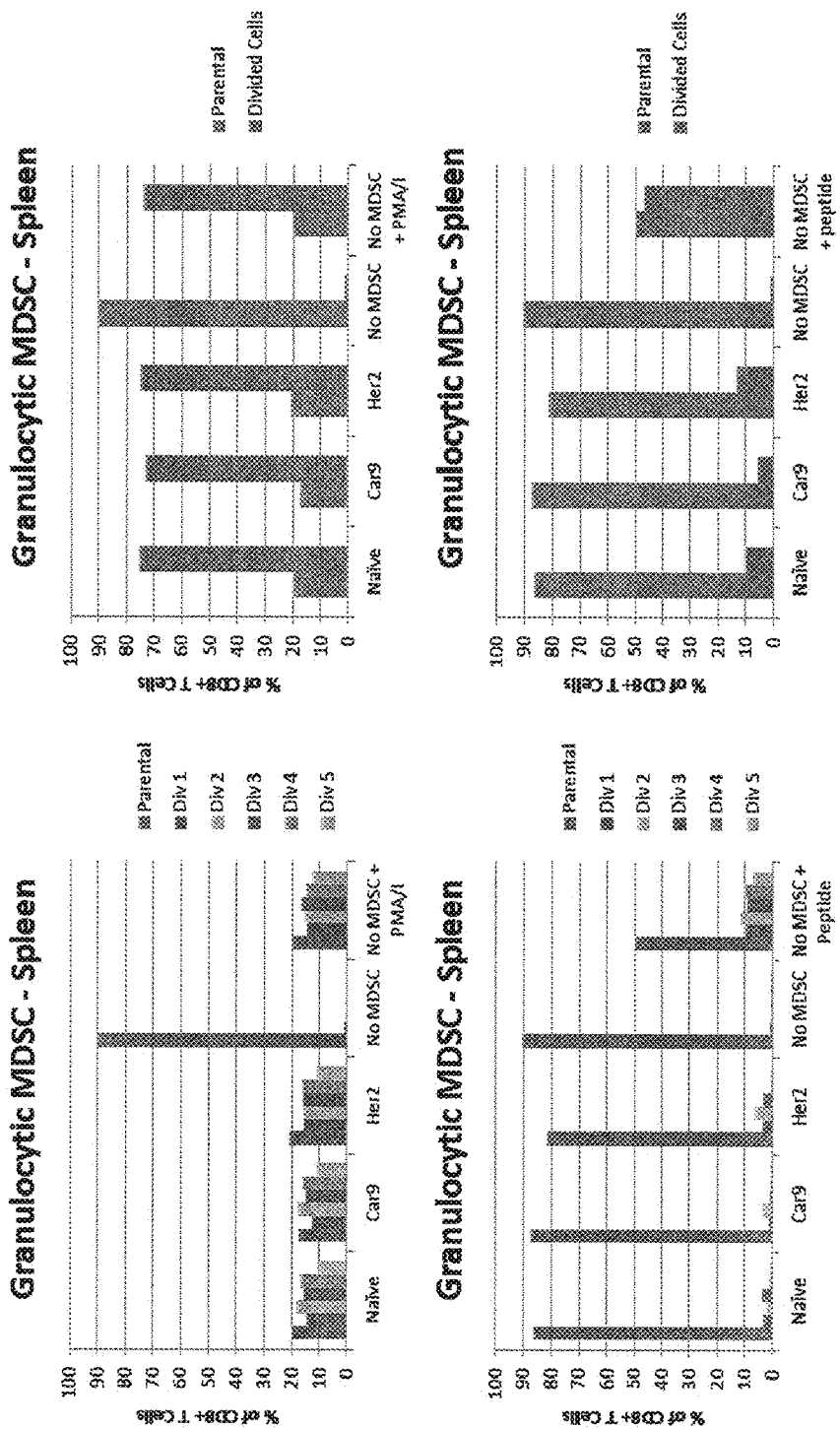
FIG. 18 shows suppressor assay data demonstrating that there is no *Listeria*-specific effect on splenic granulocytic MDSCs. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.
Figure 19:
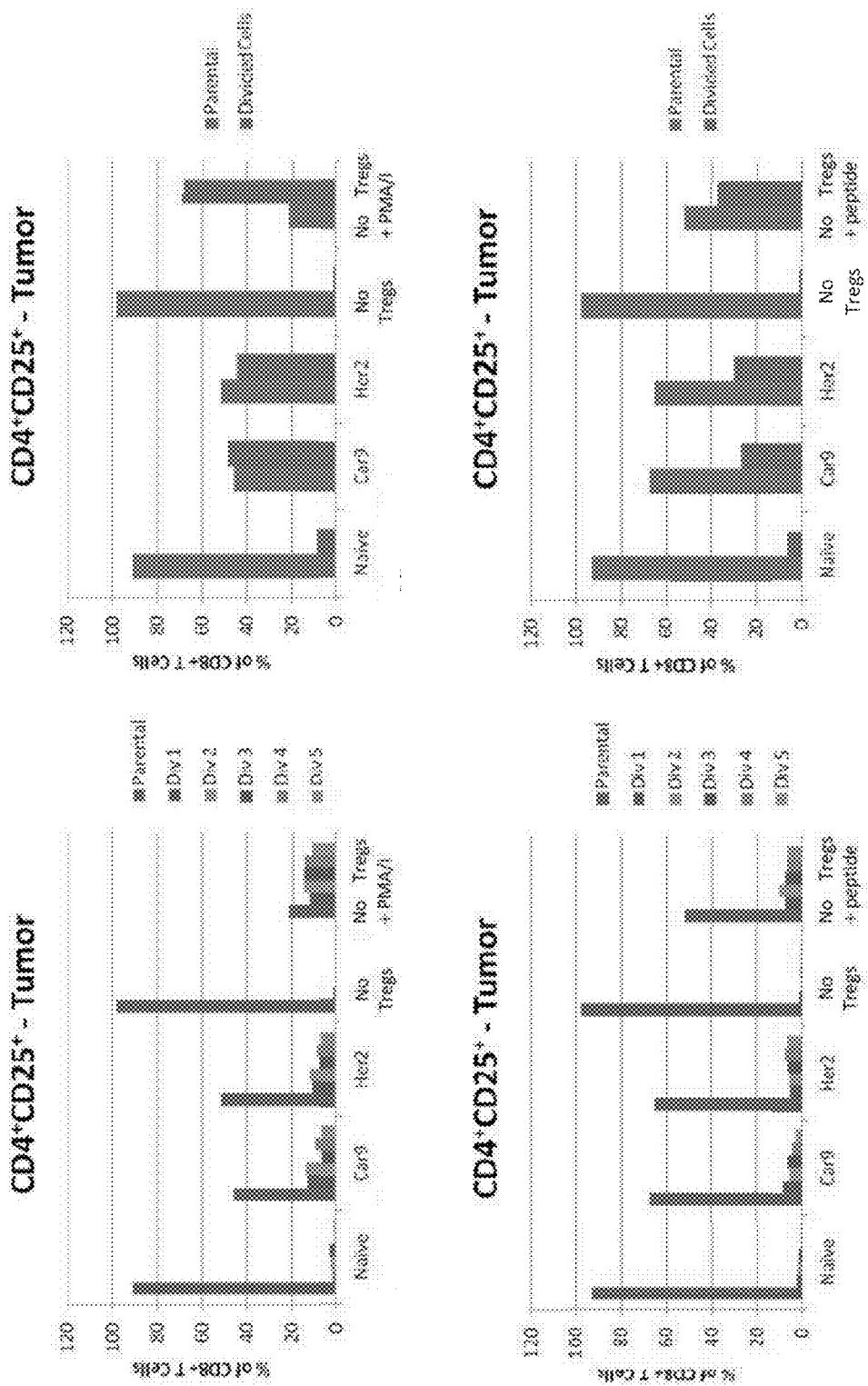
FIG. 19 shows suppressor assay data demonstrating that decrease in the suppressive ability of Tregs from 4T1 tumors after *Listeria* vaccination. This decrease is not antigen specific, as the change in Treg suppressive ability is seen with both Her2/neu-specific and non-specific responder T cells. Left-hand panels show individual cell division cycles for each group. Right-hand panels show pooled division cycles.

As a control conventional CD4+ T cells were used in place of MDSCs or Tregs and were found not to have an effect on cell division (FIG. 14).

Figure 20:
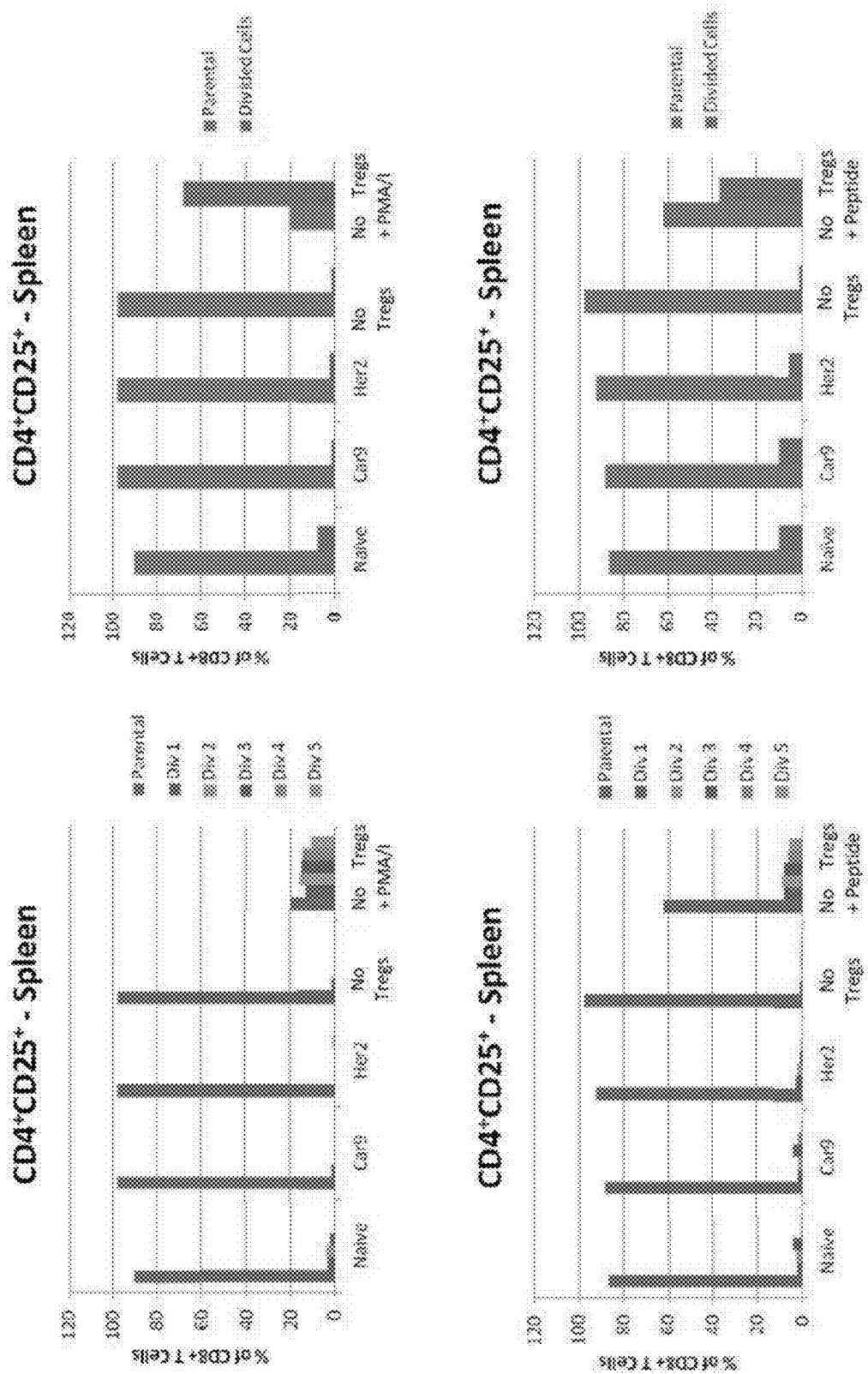
FIG. 20 shows suppressor assay data demonstrating that there is no *Listeria*-specific effect on splenic Tregs. The responder T cells are all capable of dividing, regardless of the whether or not they are antigen specific. Left-hand panels show individual cell division cycles for each group. Right-hand panels show pooled division cycles.

Example 10: MDSCs and Tregs from 4T1 Tumors but not Spleens are Less Suppressive After Listeria Vaccination As in the above, the same experiments were carried out using 4T1 tumors and the same observations were made, namely, that MDSCs are less suppressive after Listeria vaccination (FIGS. 15 & 17), that Listeria has no specific effect on splenic monocytic MDSCs (FIGS. 16 & 18), that there is a decrease in the suppressive ability of Tregs from 4T1 tumors after *Listeria* vaccination (FIG. 19), and that *Listeria* has no effect on the suppressive ability of splenic Tregs (FIG. 20).

Finally, it was observed that *Listeria* has no effect on the suppressive ability of splenic Tregs The preceding examples are presented in order to more fully illustrate the embodiments of the invention. They should in no way be construed, however, as limiting the broad scope of the invention.

Figure 21:
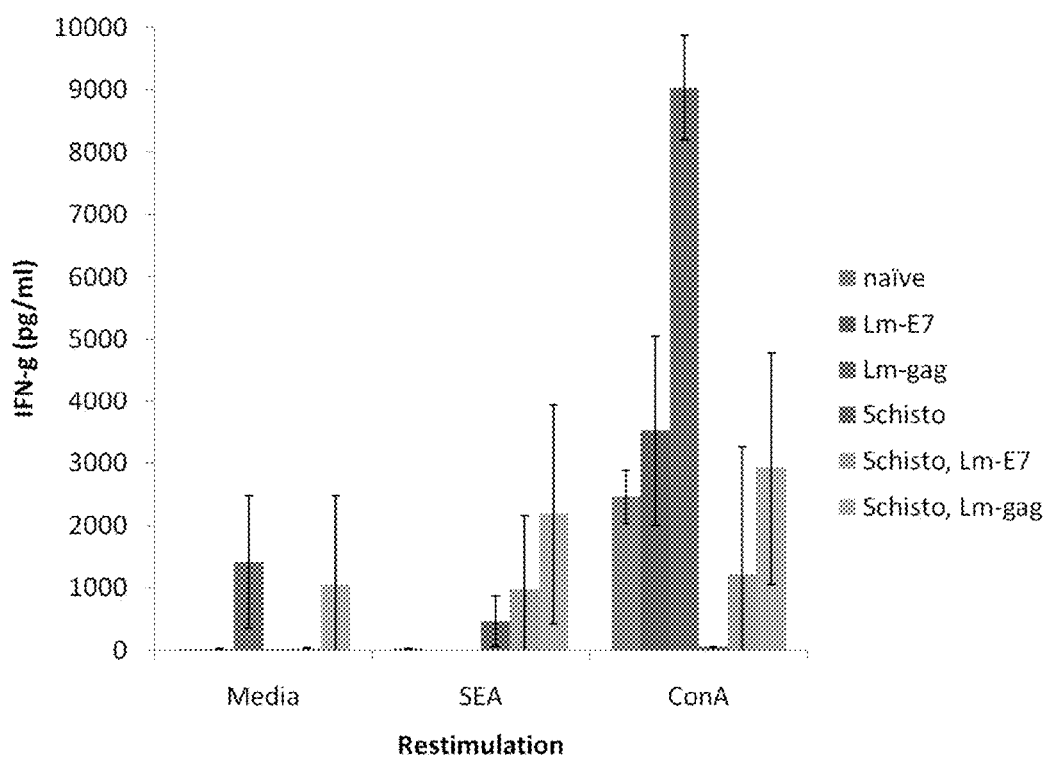
FIG. 21 shows IFN-γ production is reduced in *S. mansoni* infected mice.
Figure 22:
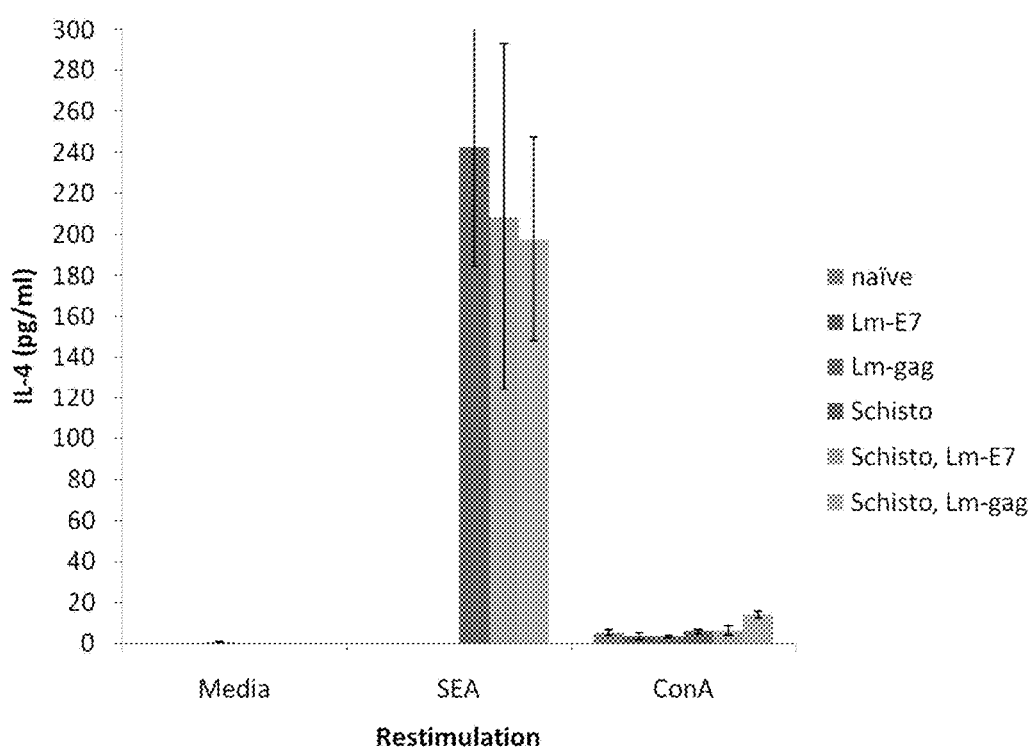
FIG. 22 shows IL-4 levels are increased in mice with chronic schistosomiasis.
Figure 23:
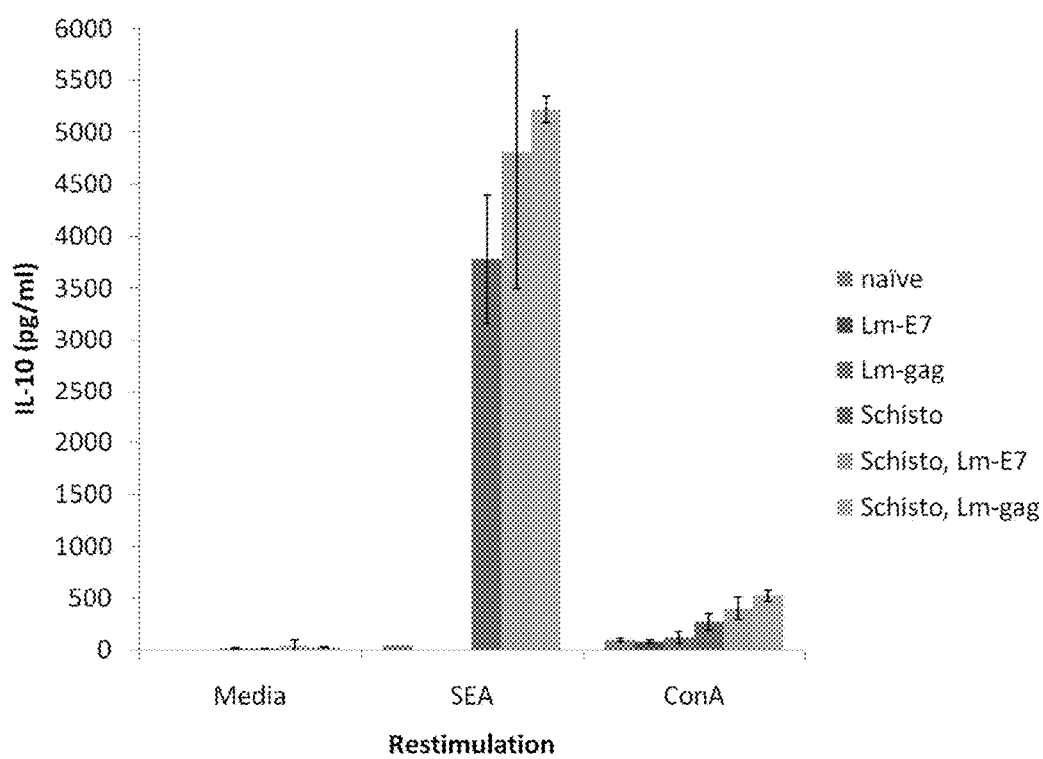
FIG. 23 shows IL-10 production is increased in mice infected with *S. mansoni*.
Figure 24:
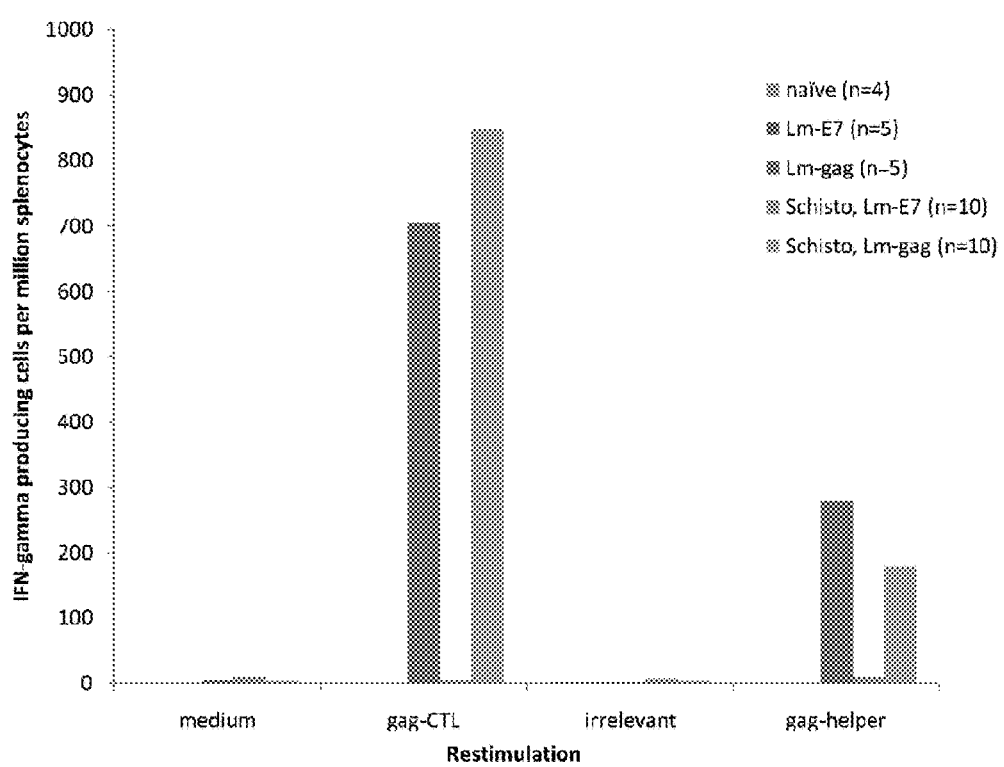
FIG. 24 shows Schistosome infection does not alter the antigen-specific vaccine responses toward immunodominant CTL and helper epitopes.

Example 11: *Listeria* Vectors are Capable of Driving a Th1 T-Cell Immune Response Despite Helminth Infection-Mediated Suppression of Th1 T-Cell Immune Response Despite systemic biasing toward Th2, as evidenced by a reduced IFN-γ response (FIG. 21) and an increase in IL-4 and IL-10 production (FIGS. 22 and 23, respectively), antigen-specific production of IFN-γ remains unchanged (FIG. 24), indicating this vaccine can produce a functional cell-mediated immune response in the presence of a Th2 environment. This observation suggests that *Listeria* vector vaccines are capable of driving vaccine-specific immune responses in helminth infected populations. Further, *Listeria* vectors should be considered in the development of new generation HIV-1, malaria or TB vaccines to be administered to populations in sub-Saharan Africa where helminth infection is highly prevalent.

The preceding examples are presented in order to more fully illustrate the embodiments of the invention. They should in no way be construed, however, as limiting the broad scope of the invention.

What is claimed is:

1. A method of reconstituting an immune response in a subject in an antigen-independent manner, the method comprising administering a live attenuated recombinant *Listeria* strain to said subject, wherein said *Listeria* strain comprises a mutation or a deletion of a genomic internalin C (inlC) gene and ActA gene, and wherein said administration reconstitutes said immune response in the subject in an antigen-independent manner.

2. The method of claim 1, wherein said *Listeria* strain comprises a nucleic acid molecule, wherein said nucleic acid molecule comprises a first open reading frame encoding a non-hemolytic LLO protein or immunogenic fragment thereof, an N-terminal ActA fragment or a truncated ActA, or a PEST amino acid sequence selected from the group consisting of SEQ ID NO: 8-19.

3. The method of claim 1, wherein said *Listeria* over expresses and secretes said non-hemolytic LLO protein or immunogenic fragment thereof, said N-terminal ActA fragment or a truncated ActA, or said PEST amino acid sequence selected from the group consisting of SEQ ID NO: 8-19.

4. The method of claim 1, wherein said recombinant *Listeria* further comprises a mutation or a deletion of a genomic PlcA gene, PrfA gene or a PlcB gene.

5. The method of claim 2, wherein said nucleic acid molecule further comprises a second open reading frame encoding a metabolic enzyme, wherein said metabolic enzyme complements an endogenous gene that is lacking in the chromosome of said recombinant *Listeria* strain.

6. The method of claim 5, wherein said metabolic enzyme encoded by said second open reading frame is an alanine racemase enzyme or a D-amino acid transferase enzyme.

7. The method of claim 2, wherein said nucleic acid molecule is integrated into the *Listeria* genome.

8. The method of claim 2, wherein said nucleic acid molecule is in a plasmid that is stably maintained in said recombinant *Listeria* strain in the absence of antibiotic selection.

9. The method of claim 1, wherein said subject is an adult human, a child or a non-human mammal.

10. The method of claim 1, wherein the *Listeria* strain is used alone or is combined with an additional adjuvant.

11. The method of claim 10, wherein said additional adjuvant is a non-nucleic acid adjuvant including aluminum adjuvant, Freund's adjuvant, MPL, emulsion, GM-CSF, QS21, SBAS2, CpG-containing oligonucleotide, a nucleotide molecule encoding an immune-stimulating cytokine, comprises a bacterial mitogen, or a bacterial toxin.

12. The method of claim 1, wherein said method allows the treatment of said disease.

13. The method of claim 12, wherein said disease is a tumor or a cancer, or an infectious disease.

14. The method of claim 13, wherein said method increases the ratio of CD8+/T regulatory cells in said tumor.

* * * * *

SEQUENCE LISTING

```
<160> NUMBER OF SEQ ID NOS: 41

<210> SEQ ID NO 1
<211> LENGTH: 1329
<212> TYPE: DNA
<213> ORGANISM: Listeria monocytogenes

<400> SEQUENCE: 1
atgaaaaaaa taatgctagt ttttattaca cttatattag ttagtctacc aattgcgcaa      60
caaactgaag caaaggatgc atctgcattc aataaagaaa attcaatttc atccatggca     120
ccaccagcat ctccgcctgc aagtcctaag acgccaatcg aaaagaaaca cgcggatgaa     180
atcgataagt atatacaagg attggattac aataaaaaca atgtattagt ataccacgga     240
gatgcagtga caaatgtgcc gccaagaaaa ggttacaaag atggaaatga atatattgtt     300
gtggagaaaa agaagaaatc catcaatcaa aataatgcag acattcaagt tgtgaatgca     360
atttcgagcc taacctatcc aggtgctctc gtaaaagcga attcggaatt agtagaaaat     420
caaccagatg ttctccctgt aaaacgtgat tcattaacac tcagcattga tttgccaggt     480
atgactaatc aagacaataa aatagttgta aaaaatgcca ctaaatcaaa cgttaacaac     540
gcagtaaata cattagtgga aagatggaat gaaaaatatg ctcaagctta tccaaatgta     600
agtgcaaaaa ttgattatga tgacgaaatg gcttacagtg aatcacaatt aattgcgaaa     660
tttggtacag catttaaagc tgtaaataat agcttgaatg taaacttcgg cgcaatcagt     720
gaagggaaaa tgcaagaaga agtcattagt tttaaacaaa tttactataa cgtgaatgtt     780
aatgaaccta caagaccttc cagattttc ggcaaagctg ttactaaaga gcagttgcaa     840
gcgcttggag tgaatgcaga aaatcctcct gcatatatct caagtgtggc gtatggccgt     900
caagtttatt tgaaattatc aactaattcc catagtacta aagtaaaagc tgcttttgat     960
gctgccgtaa gcggaaaatc tgtctcaggt gatgtagaac taacaaatat catcaaaaat    1020
tcttccttca aagccgtaat ttacggaggt tccgcaaaag atgaagttca aatcatcgac    1080
ggcaacctcg gagacttacg cgatattttg aaaaaaggcg ctacttttaa tcgagaaaca    1140
ccaggagttc ccattgctta tacaacaaac ttcctaaaag acaatgaatt agctgttatt    1200
aaaaacaact cagaatatat tgaaacaact tcaaaagctt atacagatgg aaaaattaac    1260
atcgatcact ctggaggata cgttgctcaa ttcaacattt cttgggatga agtaaattat    1320
gatctcgag                                                            1329

<210> SEQ ID NO 2
```

```
<211> LENGTH: 442
<212> TYPE: PRT
<213> ORGANISM: Listeria monocytogenes

<400> SEQUENCE: 2

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
```

```
                385                 390                 395                 400
Lys Asn Ser Glu Tyr Ile Glu Thr Thr Ser Lys Ala Tyr Thr Asp
                    405                 410                 415

Gly Lys Ile Asn Ile Asp His Ser Gly Gly Tyr Val Ala Gln Phe Asn
                420                 425                 430

Ile Ser Trp Asp Glu Val Asn Tyr Asp Leu
            435                 440

<210> SEQ ID NO 3
<211> LENGTH: 390
<212> TYPE: PRT
<213> ORGANISM: Artificial Sequence
<220> FEATURE:
<223> OTHER INFORMATION: truncated ActA

<400> SEQUENCE: 3

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
                20                  25                  30

Asn Thr Asp Glu Trp Glu Glu Glu Lys Thr Glu Glu Gln Pro Ser Glu
            35                  40                  45

Val Asn Thr Gly Pro Arg Tyr Glu Thr Ala Arg Glu Val Ser Ser Arg
        50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Asn Ser Glu Gln Thr Glu Asn Ala Ala Ile Asn Glu
                100                 105                 110

Glu Ala Ser Gly Ala Asp Arg Pro Ala Ile Gln Val Glu Arg Arg His
            115                 120                 125

Pro Gly Leu Pro Ser Asp Ser Ala Ala Glu Ile Lys Lys Arg Arg Lys
        130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
                180                 185                 190

Ser Ser Pro Gln Pro Leu Lys Ala Asn Gln Gln Pro Phe Phe Pro Lys
            195                 200                 205

Val Phe Lys Lys Ile Lys Asp Ala Gly Lys Trp Val Arg Asp Lys Ile
        210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Ser Glu Glu Val Asn Ala
                245                 250                 255

Ser Asp Phe Pro Pro Pro Thr Asp Glu Glu Leu Arg Leu Ala Leu
                260                 265                 270

Pro Glu Thr Pro Met Leu Leu Gly Phe Asn Ala Pro Ala Thr Ser Glu
            275                 280                 285

Pro Ser Ser Phe Glu Phe Pro Pro Pro Thr Asp Glu Glu Leu Arg
        290                 295                 300

Leu Ala Leu Pro Glu Thr Pro Met Leu Leu Gly Phe Asn Ala Pro Ala
```

305           310           315           320
Thr Ser Glu Pro Ser Ser Phe Glu Phe Pro Pro Pro Thr Glu Asp
                325              330              335

Glu Leu Glu Ile Ile Arg Glu Thr Ala Ser Ser Leu Asp Ser Ser Phe
            340              345              350

Thr Arg Gly Asp Leu Ala Ser Leu Arg Asn Ala Ile Asn Arg His Ser
            355              360              365

Gln Asn Phe Ser Asp Phe Pro Pro Ile Pro Thr Glu Glu Leu Asn
    370              375              380

Gly Arg Gly Gly Arg Pro
385              390

<210> SEQ ID NO 4
<211> LENGTH: 1151
<212> TYPE: PRT
<213> ORGANISM: Artificial Sequence
<220> FEATURE:
<223> OTHER INFORMATION: truncated ActA

<400> SEQUENCE: 4

Ala Thr Gly Cys Gly Thr Gly Cys Gly Ala Thr Gly Ala Thr Gly Gly
1               5                   10                  15

Thr Gly Gly Thr Thr Thr Thr Cys Ala Thr Ala Cys Thr Gly Cys
                20                  25                  30

Cys Ala Ala Thr Thr Gly Cys Ala Thr Thr Ala Cys Gly Ala Thr Thr
            35                  40                  45

Ala Ala Cys Cys Cys Cys Gly Ala Cys Ala Thr Ala Ala Thr Ala Thr
        50                  55                  60

Thr Thr Gly Cys Ala Gly Cys Gly Ala Cys Ala Gly Ala Thr Ala Gly
65                  70                  75                  80

Cys Gly Ala Ala Gly Ala Thr Thr Cys Thr Ala Gly Thr Cys Thr Ala
                85                  90                  95

Ala Ala Cys Ala Cys Ala Gly Ala Thr Gly Ala Ala Thr Gly Gly
            100                 105                 110

Ala Ala Gly Ala Ala Gly Ala Ala Ala Ala Cys Ala Gly Ala
        115                 120                 125

Ala Gly Ala Gly Cys Ala Ala Cys Cys Ala Ala Gly Cys Gly Ala Gly
    130                 135                 140

Gly Thr Ala Ala Ala Thr Ala Cys Gly Gly Gly Ala Cys Cys Ala Ala
145                 150                 155                 160

Gly Ala Thr Ala Cys Gly Ala Ala Cys Thr Gly Cys Ala Cys Gly
                165                 170                 175

Thr Gly Ala Ala Gly Thr Ala Ala Gly Thr Thr Cys Ala Cys Gly Thr
            180                 185                 190

Gly Ala Thr Ala Thr Ala Ala Gly Ala Ala Cys Thr Ala Gly
        195                 200                 205

Ala Ala Ala Ala Thr Cys Gly Ala Ala Thr Ala Ala Ala Gly Thr
    210                 215                 220

Gly Ala Gly Ala Ala Ala Thr Ala Cys Gly Ala Ala Cys Ala Ala Ala
225                 230                 235                 240

Gly Cys Ala Gly Ala Cys Cys Thr Ala Ala Thr Ala Gly Cys Ala Ala
                245                 250                 255

Thr Gly Thr Thr Gly Ala Ala Ala Gly Ala Ala Ala Ala Gly Cys
            260                 265                 270

Ala Gly Ala Ala Ala Ala Ala Gly Gly Thr Cys Cys Ala Ala Ala Thr

```
                275                 280                 285
Ala Thr Cys Ala Ala Thr Ala Ala Thr Ala Ala Cys Ala Ala Cys Ala
290                 295                 300
Gly Thr Gly Ala Ala Cys Ala Ala Cys Thr Gly Ala Gly Ala Ala
305                 310                 315                 320
Thr Gly Cys Gly Gly Cys Thr Ala Thr Ala Ala Thr Gly Ala Ala
                325                 330                 335
Gly Ala Gly Gly Cys Thr Thr Cys Ala Gly Ala Gly Cys Cys Gly
            340                 345                 350
Ala Cys Cys Gly Ala Cys Cys Ala Gly Cys Thr Ala Thr Cys Ala
        355                 360                 365
Ala Gly Thr Gly Gly Ala Gly Cys Gly Thr Cys Gly Thr Cys Ala Thr
        370                 375                 380
Cys Cys Ala Gly Gly Ala Thr Thr Gly Cys Cys Ala Thr Cys Gly Gly
385                 390                 395                 400
Ala Thr Ala Gly Cys Gly Cys Ala Gly Cys Gly Gly Ala Ala Ala Thr
                405                 410                 415
Thr Ala Ala Ala Ala Ala Ala Ala Gly Ala Ala Gly Gly Ala Ala Ala
                420                 425                 430
Gly Cys Cys Ala Thr Ala Gly Cys Ala Thr Cys Ala Thr Cys Gly Gly
        435                 440                 445
Ala Thr Ala Gly Thr Gly Ala Gly Cys Thr Thr Gly Ala Ala Ala Gly
        450                 455                 460
Cys Cys Thr Thr Ala Cys Thr Thr Ala Thr Cys Cys Gly Gly Ala Thr
465                 470                 475                 480
Ala Ala Ala Cys Cys Ala Ala Cys Ala Ala Ala Gly Thr Ala Ala
                485                 490                 495
Ala Thr Ala Ala Gly Ala Ala Ala Ala Ala Gly Thr Gly Gly Cys
            500                 505                 510
Gly Ala Ala Ala Gly Ala Gly Thr Cys Ala Gly Thr Thr Gly Cys Gly
        515                 520                 525
Gly Ala Thr Gly Cys Thr Thr Cys Thr Gly Ala Ala Ala Gly Thr Gly
        530                 535                 540
Ala Cys Thr Thr Ala Gly Ala Thr Thr Cys Thr Ala Gly Cys Ala Thr
545                 550                 555                 560
Gly Cys Ala Gly Thr Cys Ala Gly Cys Ala Gly Ala Thr Gly Ala Gly
                565                 570                 575
Thr Cys Thr Thr Cys Ala Cys Cys Ala Cys Ala Ala Cys Cys Thr Thr
            580                 585                 590
Thr Ala Ala Ala Ala Gly Cys Ala Ala Ala Cys Cys Ala Ala Cys Ala
                595                 600                 605
Ala Cys Cys Ala Thr Thr Thr Thr Cys Cys Cys Thr Ala Ala Ala
        610                 615                 620
Gly Thr Ala Thr Thr Ala Ala Ala Ala Ala Ala Thr Ala Ala
625                 630                 635                 640
Ala Ala Gly Ala Thr Gly Cys Gly Gly Gly Gly Ala Ala Ala Thr Gly
                645                 650                 655
Gly Gly Thr Ala Cys Gly Thr Gly Ala Thr Ala Ala Ala Thr Cys
            660                 665                 670
Gly Ala Cys Gly Ala Ala Ala Ala Thr Cys Cys Thr Gly Ala Ala Gly
        675                 680                 685
Thr Ala Ala Ala Gly Ala Ala Ala Gly Cys Gly Ala Thr Thr Gly Thr
        690                 695                 700
```

```
Thr Gly Ala Thr Ala Ala Ala Ala Gly Thr Gly Cys Ala Gly Gly Gly
705                 710                 715                 720

Thr Thr Ala Ala Thr Thr Gly Ala Cys Cys Ala Ala Thr Thr Ala Thr
                725                 730                 735

Thr Ala Ala Cys Cys Ala Ala Ala Ala Ala Gly Ala Ala Ala Ala Gly
            740                 745                 750

Thr Gly Ala Ala Gly Ala Gly Gly Thr Ala Ala Ala Thr Gly Cys Thr
        755                 760                 765

Thr Cys Gly Gly Ala Cys Thr Thr Cys Cys Cys Gly Cys Cys Ala Cys
    770                 775                 780

Cys Ala Cys Cys Thr Ala Cys Gly Gly Ala Thr Gly Ala Ala Gly Ala
785                 790                 795                 800

Gly Thr Thr Ala Ala Gly Ala Cys Thr Thr Gly Cys Thr Thr Thr Gly
                805                 810                 815

Cys Cys Ala Gly Ala Gly Ala Cys Ala Cys Cys Ala Ala Thr Gly Cys
            820                 825                 830

Thr Thr Cys Thr Thr Gly Gly Thr Thr Thr Thr Ala Ala Thr Gly Cys
        835                 840                 845

Thr Cys Cys Thr Gly Cys Thr Ala Cys Ala Thr Cys Ala Gly Ala Ala
    850                 855                 860

Cys Cys Gly Ala Gly Cys Thr Cys Ala Thr Thr Cys Gly Ala Ala Thr
865                 870                 875                 880

Thr Thr Cys Cys Ala Cys Cys Ala Cys Cys Ala Cys Cys Thr Ala Cys
                885                 890                 895

Gly Gly Ala Thr Gly Ala Ala Gly Ala Gly Thr Thr Ala Ala Gly Ala
            900                 905                 910

Cys Thr Thr Gly Cys Thr Thr Thr Gly Cys Cys Ala Gly Ala Gly Ala
        915                 920                 925

Cys Gly Cys Cys Ala Ala Thr Gly Cys Thr Thr Cys Thr Thr Gly Gly
    930                 935                 940

Thr Thr Thr Thr Ala Ala Thr Gly Cys Thr Cys Cys Thr Gly Cys Thr
945                 950                 955                 960

Ala Cys Ala Thr Cys Gly Gly Ala Ala Cys Cys Gly Ala Gly Cys Thr
                965                 970                 975

Cys Gly Thr Thr Cys Gly Ala Ala Thr Thr Thr Cys Cys Ala Cys Cys
            980                 985                 990

Gly Cys Cys Thr Cys Cys Ala Ala  Cys Ala Gly Ala Ala  Gly Ala Thr
        995                 1000                1005

Gly Ala  Ala Cys Thr Ala Gly  Ala Ala Ala Thr Cys  Ala Thr Cys
    1010                 1015                 1020

Cys Gly  Gly Gly Ala Ala Ala  Cys Ala Gly Cys Ala  Thr Cys Cys
    1025                 1030                 1035

Thr Cys  Gly Cys Thr Ala Gly  Ala Thr Thr Cys Thr  Ala Gly Thr
    1040                 1045                 1050

Thr Thr  Thr Ala Cys Ala Ala  Gly Ala Gly Gly Gly  Gly Ala Thr
    1055                 1060                 1065

Thr Thr  Ala Gly Cys Thr Ala  Gly Thr Thr Thr Gly  Ala Gly Ala
    1070                 1075                 1080

Ala Ala  Thr Gly Cys Thr Ala  Thr Thr Ala Ala Thr  Cys Gly Cys
    1085                 1090                 1095

Cys Ala  Thr Ala Gly Thr Cys  Ala Ala Ala Ala Thr  Thr Thr Cys
    1100                 1105                 1110
```

```
Thr Cys Thr Gly Ala Thr Thr Thr Cys Cys Cys Ala Cys Cys Ala
    1115                1120                1125

Ala Thr Cys Cys Cys Ala Ala Cys Ala Gly Ala Ala Gly Ala Ala
    1130                1135                1140

Gly Ala Gly Thr Thr Gly Ala Ala
    1145                1150

<210> SEQ ID NO 5
<211> LENGTH: 669
<212> TYPE: DNA
<213> ORGANISM: Artificial Sequence
<220> FEATURE:
<223> OTHER INFORMATION: truncated ActA

<400> SEQUENCE: 5
tttatcacgt acccatttcc ccgcatcttt tattttttta aatactttag ggaaaaatgg      60
tttttgattt gcttttaaag gttgtggtgt agactcgtct gctgactgca tgctagaatc     120
taagtcactt tcagaagcat ccacaactga ctctttcgcc acttttctct tatttgcttt     180
tgttggttta tctggataag taaggctttc aagctcacta tccgacgacg ctatggcttt     240
tcttcttttt ttaatttccg ctgcgctatc cgatgacaga cctggatgac gacgctccac     300
ttgcagagtt ggtcggtcga ctcctgaagc ctcttcattt atagccacat tcctgtttg     360 ctcaccgttg ttattattgt tattcggacc tttctctgct tttgctttca acattgctat     420
taggtctgct ttgttcgtat ttttcacttt attcgatttt tctagttcct caatatcacg     480
tgaacttact tcacgtgcag tttcgtatct tggtcccgta tttacctcgc ttggctgctc     540
ttctgttttt tcttcttccc attcatctgt gtttagactg gaatcttcgc tatctgtcgc     600
tgcaaatatt atgtcggggt taatcgtaat gcagttggca gtaatgaaaa ctaccatcat     660
cgcacgcat                                                             669

<210> SEQ ID NO 6
<211> LENGTH: 390
<212> TYPE: PRT
<213> ORGANISM: Artificial Sequence
<220> FEATURE:
<223> OTHER INFORMATION: truncated ActA

<400> SEQUENCE: 6

Met Arg Ala Met Met Val Val Phe Ile Thr Ala Asn Cys Ile Thr Ile
1                   5                   10                  15

Asn Pro Asp Ile Ile Phe Ala Ala Thr Asp Ser Glu Asp Ser Ser Leu
                20                  25                  30

Asn Thr Asp Glu Trp Glu Glu Glu Lys Thr Glu Glu Gln Pro Ser Glu
            35                  40                  45

Val Asn Thr Gly Pro Arg Tyr Glu Thr Ala Arg Glu Val Ser Ser Arg
        50                  55                  60

Asp Ile Lys Glu Leu Glu Lys Ser Asn Lys Val Arg Asn Thr Asn Lys
    65                  70                  75                  80

Ala Asp Leu Ile Ala Met Leu Lys Glu Lys Ala Glu Lys Gly Pro Asn
                85                  90                  95

Ile Asn Asn Asn Asn Ser Glu Gln Thr Glu Asn Ala Ala Ile Asn Glu
                100                 105                 110

Glu Ala Ser Gly Ala Asp Arg Pro Ala Ile Gln Val Glu Arg Arg His
            115                 120                 125

Pro Gly Leu Pro Ser Asp Ser Ala Ala Glu Ile Lys Lys Arg Arg Lys
        130                 135                 140
```

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
            165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
        275                 280                 285

Pro Ser Ser Phe Glu Phe Pro Pro Pro Thr Asp Glu Glu Leu Arg
290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
        340                 345                 350

Thr Arg Gly Asp Leu Ala Ser Leu Arg Asn Ala Ile Asn Arg His Ser
            355                 360                 365

Gln Asn Phe Ser Asp Phe Pro Pro Ile Pro Thr Glu Glu Leu Asn
        370                 375                 380

Gly Arg Gly Gly Arg Pro
385                 390

<210> SEQ ID NO 7
<211> LENGTH: 1170
<212> TYPE: DNA
<213> ORGANISM: Artificial Sequence
<220> FEATURE:
<223> OTHER INFORMATION: truncated ActA

<400> SEQUENCE: 7
atgcgtgcga tgatggtggt tttcattact gccaattgca ttacgattaa ccccgacata      60
atatttgcag cgacagatag cgaagattct agtctaaaca cagatgaatg ggaagaagaa     120
aaaacagaag agcaaccaag cgaggtaaat acgggaccaa gatacgaaac tgcacgtgaa     180
gtaagttcac gtgatattaa agaactagaa aaatcgaata aagtgagaaa tacgaacaaa     240
gcagacctaa tagcaatgtt gaaagaaaaa gcagaaaaag gtccaaatat caataataac     300
aacagtgaac aaactgagaa tgcggctata aatgaagagg cttcaggagc cgaccgacca     360
gctatacaag tggagcgtcg tcatccagga ttgccatcgg atagcgcagc ggaaattaaa     420 aaagaagga agccatagc atcatcggat agtgagcttg aaagccttac ttatccggat     480
aaaccaacaa agtaaataa gaaaaaagtg gcgaaagagt cagttgcgga tgcttctgaa     540
agtgacttag attctagcat gcagtcagca gatgagtctt caccacaacc tttaaaagca     600

-continued

```
aaccaacaac cattttttccc taaagtattt aaaaaaataa aagatgcggg gaaatgggta    660
cgtgataaaa tcgacgaaaa tcctgaagta aagaaagcga ttgttgataa aagtgcaggg    720
ttaattgacc aattattaac caaaaagaaa agtgaagagg taaatgcttc ggacttcccg    780
ccaccaccta cggatgaaga gttaagactt gctttgccag agacaccaat gcttcttggt    840
tttaatgctc ctgctacatc agaaccgagc tcattcgaat ttccaccacc acctacggat    900
gaagagttaa gacttgcttt gccagagacg ccaatgcttc ttggttttaa tgctcctgct    960
acatcggaac cgagctcgtt cgaatttcca ccgcctccaa cagaagatga actagaaatc   1020
atccgggaaa cagcatcctc gctagattct agttttacaa gagggatttt agctagtttg   1080
agaaatgcta ttaatcgcca tagtcaaaat ttctctgatt tcccaccaat cccaacagaa   1140
gaagagttga acgggagagg cggtagacca                                    1170
```

<210> SEQ ID NO 8
<211> LENGTH: 32
<212> TYPE: PRT
<213> ORGANISM: Listeria monocytogenes

<400> SEQUENCE: 8

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 9
<211> LENGTH: 19
<212> TYPE: PRT
<213> ORGANISM: Listeria monocytogenes

<400> SEQUENCE: 9

Lys Glu Asn Ser Ile Ser Ser Met Ala Pro Pro Ala Ser Pro Pro Ala
1               5                   10                  15

Ser Pro Lys

<210> SEQ ID NO 10
<211> LENGTH: 14
<212> TYPE: PRT
<213> ORGANISM: Listeria monocytogenes

<400> SEQUENCE: 10

Lys Thr Glu Glu Gln Pro Ser Glu Val Asn Thr Gly Pro Arg
1               5                   10

<210> SEQ ID NO 11
<211> LENGTH: 28
<212> TYPE: PRT
<213> ORGANISM: Listeria monocytogenes

<400> SEQUENCE: 11

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 12
<211> LENGTH: 20
<212> TYPE: PRT
<213> ORGANISM: Listeria monocytogenes

<400> SEQUENCE: 12

```
Lys Asn Glu Glu Val Asn Ala Ser Asp Phe Pro Pro Pro Thr Asp
1               5                   10                  15

Glu Glu Leu Arg
            20

<210> SEQ ID NO 13
<211> LENGTH: 33
<212> TYPE: PRT
<213> ORGANISM: Listeria monocytogenes

<400> SEQUENCE: 13

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

<210> SEQ ID NO 14
<211> LENGTH: 28
<212> TYPE: PRT
<213> ORGANISM: Listeria monocytogenes

<400> SEQUENCE: 14

Lys Glu Ser Val Val Asp Ala Ser Glu Ser Asp Leu Asp Ser Ser Met
1               5                   10                  15

Gln Ser Ala Asp Glu Ser Thr Pro Gln Pro Leu Lys
            20                  25

<210> SEQ ID NO 15
<211> LENGTH: 20
<212> TYPE: PRT
<213> ORGANISM: Listeria monocytogenes

<400> SEQUENCE: 15

Lys Ser Glu Glu Val Asn Ala Ser Asp Phe Pro Pro Pro Pro Thr Asp
1               5                   10                  15

Glu Glu Leu Arg
            20

<210> SEQ ID NO 16
<211> LENGTH: 33
<212> TYPE: PRT
<213> ORGANISM: Listeria monocytogenes

<400> SEQUENCE: 16

Arg Gly Gly Arg Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

<210> SEQ ID NO 17
<211> LENGTH: 19
<212> TYPE: PRT
<213> ORGANISM: Listeria seeligeri

<400> SEQUENCE: 17

Arg Ser Glu Val Thr Ile Ser Pro Ala Glu Thr Pro Glu Ser Pro Pro
1               5                   10                  15

Ala Thr Pro
```

<210> SEQ ID NO 18
<211> LENGTH: 17
<212> TYPE: PRT
<213> ORGANISM: Streptococcus pyogenes

<400> SEQUENCE: 18

Lys Gln Asn Thr Ala Ser Thr Glu Thr Thr Thr Thr Asn Glu Gln Pro
1               5                   10                  15
Lys

<210> SEQ ID NO 19
<211> LENGTH: 17
<212> TYPE: PRT
<213> ORGANISM: Streptococcus equisimilis

<400> SEQUENCE: 19

Lys Gln Asn Thr Ala Asn Thr Glu Thr Thr Thr Thr Asn Glu Gln Pro
1               5                   10                  15
Lys

<210> SEQ ID NO 20
<211> LENGTH: 21
<212> TYPE: DNA
<213> ORGANISM: Artificial Sequence
<220> FEATURE:
<223> OTHER INFORMATION: dal gene forward primer

<400> SEQUENCE: 20
ccatggtgac aggctggcat c                                          21

<210> SEQ ID NO 21
<211> LENGTH: 27
<212> TYPE: DNA
<213> ORGANISM: Artificial Sequence
<220> FEATURE:
<223> OTHER INFORMATION: dal gene reverse primer

<400> SEQUENCE: 21
gctagcctaa tggatgtatt ttctagg                                    27

<210> SEQ ID NO 22
<211> LENGTH: 27
<212> TYPE: DNA
<213> ORGANISM: Artificial Sequence
<220> FEATURE:
<223> OTHER INFORMATION: minimal p60 promoter sequence forward primer

<400> SEQUENCE: 22
ttaattaaca aatagttggt atagtcc                                    27

<210> SEQ ID NO 23
<211> LENGTH: 36
<212> TYPE: DNA
<213> ORGANISM: Artificial Sequence
<220> FEATURE:
<223> OTHER INFORMATION: minimal p60 promoter sequence forward primer

<400> SEQUENCE: 23
gacgatgcca gcctgtcacc atggaaaact cctctc                          36

<210> SEQ ID NO 24
<211> LENGTH: 156
<212> TYPE: DNA

<213> ORGANISM: Artificial Sequence
<220> FEATURE:
<223> OTHER INFORMATION: truncated p60 promoter

<400> SEQUENCE: 24
caaatagttg gtatagtcct ctttagcctt tggagtatta tctcatcatt tgtttttag      60 gtgaaaactg ggtaaactta gtattatcaa tataaaatta attctcaaat acttaattac    120
gtactgggat ttctgaaaa aagagaggag ttttcc                               156

<210> SEQ ID NO 25
<211> LENGTH: 25
<212> TYPE: DNA
<213> ORGANISM: Artificial Sequence
<220> FEATURE:
<223> OTHER INFORMATION: oriRep forward primer

<400> SEQUENCE: 25
ggcgccacta actcaacgct agtag                                           25

<210> SEQ ID NO 26
<211> LENGTH: 27
<212> TYPE: DNA
<213> ORGANISM: Artificial Sequence
<220> FEATURE:
<223> OTHER INFORMATION: oriRep reverse primer

<400> SEQUENCE: 26
gctagccagc aaagaaaaac aaacacg                                         27

<210> SEQ ID NO 27
<211> LENGTH: 38
<212> TYPE: DNA
<213> ORGANISM: Artificial Sequence
<220> FEATURE:
<223> OTHER INFORMATION: oriRep forward primer

<400> SEQUENCE: 27
gtcgacggtc accggcgcca ctaactcaac gctagtag                             38

<210> SEQ ID NO 28
<211> LENGTH: 35
<212> TYPE: DNA
<213> ORGANISM: Artificial Sequence
<220> FEATURE:
<223> OTHER INFORMATION: oriRep reverse primer

<400> SEQUENCE: 28
ttaattaagc tagccagcaa agaaaaacaa acacg                                35

<210> SEQ ID NO 29
<211> LENGTH: 29
<212> TYPE: DNA
<213> ORGANISM: Artificial Sequence
<220> FEATURE:
<223> OTHER INFORMATION: F primer for amplifying LLO-E7 gene

<400> SEQUENCE: 29
atgaaaaaaa taatgctagt ttttattac                                       29

<210> SEQ ID NO 30
<211> LENGTH: 48
<212> TYPE: DNA
<213> ORGANISM: Artificial Sequence
<220> FEATURE:
<223> OTHER INFORMATION: R primer for amplifying LLO-E7 gene

<400> SEQUENCE: 30
gcggccgctt aatgatgatg atgatgatgt ggtttctgag aacagatg        48

<210> SEQ ID NO 31
<211> LENGTH: 22
<212> TYPE: DNA
<213> ORGANISM: Artificial Sequence
<220> FEATURE:
<223> OTHER INFORMATION: Taqman primer-probe sets

<400> SEQUENCE: 31
gcaagtgtga ctctacgctt cg        22

<210> SEQ ID NO 32
<211> LENGTH: 21
<212> TYPE: DNA
<213> ORGANISM: Artificial Sequence
<220> FEATURE:
<223> OTHER INFORMATION: Taqman primer-probe sets

<400> SEQUENCE: 32
tgcccattaa caggtcttcc a        21

<210> SEQ ID NO 33
<211> LENGTH: 32
<212> TYPE: DNA
<213> ORGANISM: Artificial Sequence
<220> FEATURE:
<223> OTHER INFORMATION: Taqman primer-probe sets

<400> SEQUENCE: 33
tgcgtacaaa gcacacacgt agacattcgt ac        32

<210> SEQ ID NO 34
<211> LENGTH: 24
<212> TYPE: DNA
<213> ORGANISM: Artificial Sequence
<220> FEATURE:
<223> OTHER INFORMATION: Taqman primer-probe sets

<400> SEQUENCE: 34
tgacatcgtt tgtgtttgag ctag        24

<210> SEQ ID NO 35
<211> LENGTH: 23
<212> TYPE: DNA
<213> ORGANISM: Artificial Sequence
<220> FEATURE:
<223> OTHER INFORMATION: Taqman primer-probe sets

<400> SEQUENCE: 35
gcagcgctct ctataccagg tac        23

<210> SEQ ID NO 36
<211> LENGTH: 38
<212> TYPE: DNA
<213> ORGANISM: Artificial Sequence
<220> FEATURE:
<223> OTHER INFORMATION: Taqman primer-probe sets

<400> SEQUENCE: 36
ttaatgtcca tgttatgtct ccgttatagc tcatcgta        38

<210> SEQ ID NO 37

<211> LENGTH: 2015
<212> TYPE: DNA
<213> ORGANISM: Artificial Sequence
<220> FEATURE:
<223> OTHER INFORMATION: DNA fragment that are present upstream and downstream of inl C region

<400> SEQUENCE: 37

```
atggcgcggg atggtatact atacaagcgt atggttcaaa agatacttt gaattaagaa      60
gtacaataaa gttaacttca ttagacaaaa agaaaaaaca aggaagaata gtacatagtt     120
ataaatactt ggagagtgag gtgtaatatg ggggcagctg attttggggg tttcatatat     180
gtagtttcaa gattagccat tgttgcggca gtagtttact tcttatactt attgagaaaa     240
attgcaaata aatagaaaaa aagccttgtc aaacgaggct tttttatgc aaaaaatacg     300
acgaatgaag ccatgtgaga caatttggaa tagcagacaa caaggaaggt agaacatgtt     360
ttgaaaaatt tactgatttt cgattattat taacgcttgt taatttaaac atctcttatt     420
tttgctaaca tataagtata caaagggaca taaaaaggtt aacagcgttt gttaaatagg     480
aagtatatga aaatcctctt ttgtgtttct aaatttattt ttaaggagtg gagaatgttg     540
aaaaaaaata attggttaca aaatgcagta atagcaatgc tagtgttaat tgtaggtctg     600
tgcattaata tgggttctgg aacaaaagta caagctgaga gtattcaacg accaacgcct     660
attaaccaag ttttccaga tcccggccta gcgaatgcag tgaaacaaaa tttagggaag     720
caaagtgtta cagaccttgt atcacaaaag gaactatctg gagtacaaaa tttcaatgga     780
gataatagca acattcaatc tcttgcggga atgcaatttt tcactaattt aaaagaactt     840
catctatccc ataatcaaat aagtgacctt agtcctttaa aggatctaac taagttagaa     900
gagctatctg tgaatagaaa cagactgaaa aatttaaacg gaattccaag tgcttgttta     960
tctcgcttgt ttttagataa caacgaactc agagatactg actcgcttat tcatttgaaa    1020
aatctagaaa tcttatctat tcgtaataat aagttaaaaa gtattgtgat gcttggtttt    1080
ttatcaaaac tagaggtatt agatttgcat ggtaatgaaa taacaaatac aggtggacta    1140
actagattga agaaagttaa ctggatagat ttaactggtc agaaatgtgt gaatgaacca    1200
gtaaaatacc aaccagaatt gtatataaca aatactgtca aagacccaga tggaagatgg    1260
atatctccat attacatcag taatggtggg agttatgtag atggttgtgt cctgtgggaa    1320
ttgccagttt atacagatga agtaagctat aagtttagcg aatatataaa cgttggggag    1380
actgaggcta tatttgatgg aacagttaca caacctatca agaattagga cttgtgcaca    1440
cctgtatact ttgagctctc gtataatcac gagagctttt taaatatgta agtcttaatt    1500
atctcttgac aaaaagaacg tttattcgta taaggttacc aagagatgaa gaaactattt    1560
tatttacaat tcaccttgac accaaaaact ccatatgata tagtaaataa ggttattaaa    1620
caagaaagaa gaagcaaccc gcttctcgcc tcgttaacac gaacgttttc aggcaaaaaa    1680
ttcaaacttt cgtcgcgtag cttacgcgat tttgaatgtg cgggattgct gaaaagcagc    1740
ccgtttttt atggcctccg aacgaatgag ttagcaggcc gcagatttga acagctattt    1800
tctatcttgt tgtaacaaaa ttaagtggag gtggctcacc attagcaaag acatgttggt    1860
aaacgatggg attcgtgcac gtgaagtaag attgatcgac caagacggtg aacaattagg    1920
cgtgaagagt aaaatcgatg cgcttcaaat tgctgaaaag gctaatcttg atctagtgct    1980
tgttgctcca acagcgaaac cgccagtagc tcgta                                2015
```

<210> SEQ ID NO 38

-continued

```
<211> LENGTH: 1140
<212> TYPE: DNA
<213> ORGANISM: Artificial Sequence
<220> FEATURE:
<223> OTHER INFORMATION: DNA fragment that are present upstream and
      downstream of inl C region

<400> SEQUENCE: 38
gaattcatgg cgcgggatgg tatactatac aagcgtatgg ttcaaaaaga tactttgaat      60
taagaagtac aataaagtta acttcattag acaaaaagaa aaaacaagga agaatagtac     120
atagttataa atacttggag agtgaggtgt aatatggggg cagctgattt ttggggtttc     180
atatatgtag tttcaagatt agccattgtt gcggcagtag tttacttctt atacttattg     240
agaaaaattg caaataaata gaaaaaaagc cttgtcaaac gaggcttttt ttatgcaaaa     300
aatacgacga atgaagccat gtgagacaat ttggaatagc agacaacaag gaaggtagaa     360
catgttttga aaaatttact gattttcgat tattattaac gcttgttaat ttaaacatct     420
cttattttg ctaacatata agtatacaaa gggacataaa aaggttaaca gcgtttgtta      480
aataggaagt atatgaaaat cctcttttgt gtttctaaat ttatttttaa ggagtggaga     540
ggatccggac ttgtgcacac ctgtatactt tgagctctcg tataatcacg agagcttttt     600
aaatatgtaa gtcttaatta tctcttgaca aaaagaacgt ttattcgtat aaggttacca     660
agagatgaag aaactatttt atttacaatt caccttgaca ccaaaaactc catatgatat     720
agtaaataag gttattaaac aagaaagaag aagcaacccg cttctcgcct cgttaacacg     780
aacgttttca ggcaaaaaat tcaaactttc gtcgcgtagc ttacgcgatt ttgaatgtgc     840
gggattgctg aaaagcagcc cgttttttta tggcctccga acgaatgagt tagcaggccg     900
cagatttgaa cagctatttt ctatcttgtt gtaacaaaat taagtggagg tggctcacca     960
ttagcaaaga catgttggta aacgatggga ttcgtgcacg tgaagtaaga ttgatcgacc    1020
aagacggtga acaattaggc gtgaagagta aaatcgatgc gcttcaaatt gctgaaaagg    1080
ctaatcttga tctagtgctt gttgctccaa cagcgaaacc gccagtagct cgtactgcag    1140

<210> SEQ ID NO 39
<211> LENGTH: 19
<212> TYPE: DNA
<213> ORGANISM: Artificial Sequence
<220> FEATURE:
<223> OTHER INFORMATION: primer to verify deletion of ActA

<400> SEQUENCE: 39
tgggatggcc aagaaattc                                                   19

<210> SEQ ID NO 40
<211> LENGTH: 22
<212> TYPE: DNA
<213> ORGANISM: Artificial Sequence
<220> FEATURE:
<223> OTHER INFORMATION: primer to verify deletion of ActA

<400> SEQUENCE: 40
ctaccatgtc ttccgttgct tg                                               22

<210> SEQ ID NO 41
<211> LENGTH: 1256
<212> TYPE: DNA
<213> ORGANISM: Listeria monocytogenes

<400> SEQUENCE: 41
```

```
-continued gcgccaaatc attggttgat tggtgaggat gtctgtgtgc gtgggtcgcg agatgggcga       60
ataagaagca ttaaagatcc tgacaaatat aatcaagcgg ctcatatgaa agattacgaa      120
tcgcttccac tcacagagga aggcgactgg ggcggagttc attataatag tggtatcccg      180
aataaagcag cctataatac tatcactaaa cttggaaaag aaaaaacaga acagctttat      240
tttcgcgcct taaagtacta tttaacgaaa aaatcccagt ttaccgatgc gaaaaaagcg      300
cttcaacaag cagcgaaaga tttatatggt gaagatgctt ctaaaaaagt tgctgaagct      360
tgggaagcag ttggggttaa ctgattaaca aatgttagag aaaaattaat tctccaagtg      420
atattcttaa aataattcat gaatattttt tcttatatta gctaattaag aagataacta      480
actgctaatc caatttttaa cggaacaaat tagtgaaaat gaaggccgaa ttttccttgt      540
tctaaaaagg ttgtattagc gtatcacgag gagggagtat aagtgggatt aaacagattt      600
atgcgtgcga tgatggtggt tttcattact gccaattgca ttacgattaa ccccgacgtc      660
gacccatacg acgttaattc ttgcaatgtt agctattggc gtgttctctt taggggcgtt      720
tatcaaaatt attcaattaa gaaaaaataa ttaaaaacac agaacgaaag aaaaagtgag      780
gtgaatgata tgaaattcaa aaaggtggtt ctaggtatgt gcttgatcgc aagtgttcta      840
gtctttccgg taacgataaa agcaaatgcc tgttgtgatg aatacttaca aacacccgca      900
gctccgcatg atattgacag caaattacca cataaactta gttggtccgc ggataacccg      960
acaaatactg acgtaaatac gcactattgg cttttttaaac aagcggaaaa aatactagct     1020
aaagatgtaa atcatatgcg agctaattta atgaatgaac ttaaaaaatt cgataaacaa     1080
atagctcaag gaatatatga tgcggatcat aaaaatccat attatgatac tagtacattt     1140
ttatctcatt tttataatcc tgatagagat aatacttatt tgccgggttt tgctaatgcg     1200
aaaataacag gagcaaagta tttcaatcaa tcggtgactg attaccgaga agggaa        1256
```